United States Patent
Kuhn et al.

(10) Patent No.: US 12,281,138 B2
(45) Date of Patent: Apr. 22, 2025

(54) 5'-CAP-TRINUCLEOTIDE- OR HIGHER OLIGONUCLEOTIDE COMPOUNDS AND THEIR USE IN STABILIZING RNA, EXPRESSING PROTEINS IN THERAPY

(71) Applicant: BioNTech RNA Pharmaceuticals GmbH, Mainz (DE)

(72) Inventors: Andreas Kuhn, Mainz (DE); Hiromi Muramatsu, Mainz (DE); Katalin Kariko, Mainz (DE); Stephanie Fesser, Mainz (DE); Ugur Sahin, Mainz (DE)

(73) Assignee: BioNTech RNA Pharmaceuticals GmbH, Mainz (DE)

( * ) Notice: Subject to any disclaimer, the term of this patent is extended or adjusted under 35 U.S.C. 154(b) by 781 days.

(21) Appl. No.: 16/980,300

(22) PCT Filed: Mar. 14, 2019

(86) PCT No.: PCT/EP2019/056502
§ 371 (c)(1),
(2) Date: Sep. 11, 2020

(87) PCT Pub. No.: WO2019/175356
PCT Pub. Date: Sep. 19, 2019

(65) Prior Publication Data
US 2021/0363172 A1    Nov. 25, 2021

(30) Foreign Application Priority Data
Mar. 15, 2018 (WO) .................. PCT/EP2018/056595

(51) Int. Cl.
*C07H 21/02* (2006.01)
*A61K 31/7125* (2006.01)
*A61K 48/00* (2006.01)

(52) U.S. Cl.
CPC .......... *C07H 21/02* (2013.01); *A61K 31/7125* (2013.01); *A61K 48/005* (2013.01)

(58) Field of Classification Search
CPC .............................. C07H 21/02; A61K 48/005
See application file for complete search history.

(56) References Cited

U.S. PATENT DOCUMENTS

2012/0195917 A1*  8/2012  Sahin ............... A61P 43/00
                                                      435/375
2015/0110858 A1*  4/2015  DeRosa ............. A61P 3/00
                                                      514/44 R

FOREIGN PATENT DOCUMENTS

| JP | 2013501014 A | 1/2013 |
| WO | 2008157688 A2 | 12/2008 |
| WO | 2011015347 A1 | 2/2011 |
| WO | 2017053297 A1 | 3/2017 |
| WO | WO 2017/066797 A1 | 4/2017 |
| WO | WO-2017066793 A1 * | 4/2017 ............ C07H 19/20 |
| WO | WO 2019/175356 A1 | 9/2019 |

OTHER PUBLICATIONS

Hyde et al , Innate immune restriction and antagonism of viral RNA lacking 2'-O methylation, Virology, 2015, 479-480, pp. 66-74 (Year: 2015).*
Genes and Genomes: A Changing Perspective. M. Singer and P. Berg, Mill Valley: University Science Books, 1991, p. 52.
Alberts, B. (2015) Molecular Biology of the Cell. 6th Edition, Garland Science, Taylor and Francis Group, New York.—References—Scientific Research Publishing.
Rosano et al., Frontiers in Microbiology, 5(172): 1-17 (2014).
Banjeree, Microbiological Review, 44(2): 175-205 (1980).
Belanger et al., J Biol Chem 285(43), 33037-33044, 2010.
Henry et al. Clinical use of erythropoietin. Current Opinion in Hematology, 1995, 2(2): 118-124.
Sonksen et al. Insulin: understanding its action in health and disease. British Journal of Anaesthesia, 2000, 85(1): 69-79.
Abbas et al., *PNAS*, 114(11): E2106-E2115 (2017).
Ishikawa et al., *Nucleic Acids Symposium Series*, 53(1): 129-130 (2009).
Kowalska et al., *RNA*, 14(6): 1119-1131 (2008).
Kuhn et al., *Gene Therapy*, 17: 961-971 (2010).
Strenkowska et al., *New J. Chem.*, 34(5): 993-1007 (2010).
Strenkowska et al., *Nucleic Acids Research*, 44(20): 9578-9590 (2016).
Su et al., *RNA*, 17(5): 978-988 (2011).
European Patent Office, International Search Report in International Application No. PCT/EP2019/056502 (Jul. 25, 2019).
Grudzien-Nogalska et al., RNA, 13, 1745-1755, 2007.

\* cited by examiner

*Primary Examiner* — Ekaterina Poliakova-Georgantas
(74) *Attorney, Agent, or Firm* — Neal, Gerber & Eisenberg LLP

(57) ABSTRACT

The present invention relates to 5'-cap compounds, in particular the stabilization of RNA by such 5'-cap compounds, and provides compositions, such as pharmaceutical compositions, and cells comprising an RNA which is modified with such a 5'-cap compound, as well as methods for producing a peptide or protein of interest using the compositions or cells according to the present invention. Furthermore, the present invention provides the RNA, compositions, or cells for use in therapy, in particular for use in a method of treating a disease or disorder by protein replacement therapy, genome engineering, genetic reprogramming, and immunotherapy; a method for increasing the stability of RNA in cells; a method for increasing the expression of RNA in cells; and a method for providing an RNA with a 5'-cap structure.

69 Claims, 5 Drawing Sheets

A

B

5'-CAP-TRINUCLEOTIDE- OR HIGHER OLIGONUCLEOTIDE COMPOUNDS AND THEIR USE IN STABILIZING RNA, EXPRESSING PROTEINS IN THERAPY

CROSS-REFERENCE TO RELATED APPLICATIONS

This application is a National Stage Entry of International Application Number PCT/EP2019/056502, which was filed on Mar. 14, 2019 and claimed priority to International Application Number PCT/EP2018/056595, which was filed on Mar. 15, 2018. The contents of each of the aforementioned applications are incorporated herein by reference in their entireties.

TECHNICAL FIELD OF THE INVENTION

The present invention relates to 5'-cap compounds, in particular trinucleotides or higher homologues, wherein the 5'-cap compounds contain at least one phosphorothioate, phosphoroselenoate and/or boranophosphate moiety in the phosphate bridge between the first and second nucleotide, and wherein the second nucleotide is blocked at its 2'-position. In particular, the present invention relates to stabilization of RNA by such 5'-cap compounds, in particular in the context of using RNA for expressing a peptide or protein of interest, such as in the context of vaccination, and provides compositions, such as pharmaceutical compositions, and cells comprising an RNA which is modified with such a 5'-cap compound, as well as methods for producing a peptide or protein of interest using the compositions or cells according to the present invention. Furthermore, the present invention provides the RNA, compositions, or cells for use in therapy, in particular for use in a method of treating a disease or disorder by protein replacement therapy, genome engineering, genetic reprogramming, or immunotherapy; a method for increasing the stability of RNA in cells; a method for increasing the expression of RNA in cells; and a method for providing an RNA with a 5'-cap structure.

BACKGROUND OF THE INVENTION

The concept of nucleic acid-encoded therapeutics was conceived in 1990 when Wolff et al. (Science, 247: 1465-1468) showed that direct intramuscular injection of in vitro transcribed (IVT) mRNA or plasmid DNA (pDNA) into the skeletal muscle of mice led to the expression of the encoded proteins in the injected muscle. This finding was a major incentive in the field to further investigate the applicability of nucleic acids in therapy, in particular immunotherapy. At first, DNA based vaccines against infectious pathogens have been studied (Cox et al., 1993, J. Virol. 67: 5664-5667; Davis et al., 1993, Hum. Mol. Genet. 2: 1847-1851; Ulmer et al., 1993, Science 259: 1745-1749; Wang et al., 1993, Proc. Natl. Acad. Sci. U.S.A. 90: 4156-4160). Furthermore, the applicability of nucleic acids in gene therapy against tumors and for induction of a specific anti-tumor immunity has been studied (Conry et al., 1994, Cancer Res. 54: 1164-1168; Conry et al., 1995, Gene Ther. 2: 59-65; Spooner et al., 1995, Gene Ther. 2: 173-180; Wang et al., 1995, Hum. Gene Ther. 6: 407-418).

Nucleic acid based therapy exhibits a number of advantages. For example, the manufacture of nucleic acid based therapeutics is straight forward, relatively inexpensive, and DNA based therapeutics are stable for long-term storage. However, in particular, DNA based therapeutics exhibit a variety of potential safety risks such as induction of anti-DNA antibodies (Gilkeson et al., 1995, J. Clin. Invest. 95: 1398-1402) and potential integration of the transgene into the host genome. This may lead to the inactivation of cellular genes, an uncontrollable long term expression of the transgene, or oncogenesis, and thus, is generally not applicable for tumor-associated antigens with oncogenic potential such as erb-B2 (Bargmann et al., 1986, Nature 319: 226-230) and p53 (Greenblatt et al., 1994, Cancer Res. 54: 4855-4878).

The use of RNA provides an attractive alternative to circumvent the potential risks of DNA based therapeutics. Some of the advantages of RNA based therapy are the transient expression and the non-transforming character. Furthermore, RNA does not have to be transported into the nucleus for the transgene to be expressed, and moreover, cannot be integrated into the host genome.

Two different strategies have been pursued for therapy with IVT RNA, which have both been successfully tested in various animal models. Either the RNA is directly injected into the patient by different routes (Hoerr et al., 2000, Eur. J. Immunol. 30: 1-7) or dendritic cells are transfected with IVT RNA using conventional transfection methods in vitro and then the transfected dendritic cells are administered to the patient (Heiser et al., 2000, J. Immunol. 164: 5508-5514). It has been shown that immunization with RNA transfected dendritic cells induces antigen-specific cytotoxic T-lymphocytes (CTL) in vitro and in vivo (Su et al., 2003, Cancer Res. 63: 2127-2133; Heiser et al., 2002, J. Clin. Invest. 109: 409-417). Furthermore, it has been shown that direct injection of naked RNA into the lymph nodes of laboratory animals (intranodal injection) leads to uptake of said RNA primarily by immature dendritic cells, probably by a process called macropinocytosis (cf. DE 10 2008 061 522.6). It is assumed that the RNA is translated and the expressed protein is presented on the MHC molecules on the surface of the antigen presenting cells to elicit an immune response.

A major disadvantage of RNA based therapy is the instability of the RNA in vivo. Degradation of long-chain RNA from the 5'-end is induced in the cell by the so called "decapping" enzyme Dcp2 which cleaves $m^7GDP$ from the RNA chain. Thus, it is assumed that the cleavage occurs between the alpha- and beta-phosphate groups of the RNA-cap.

Eukaryotic messenger RNAs (mRNAs) carry a specific structure at the 5'-end, the so-called cap structure. This consists of a $N^7$-methylated guanosine moiety, which is added to the first transcribed nucleotide of an RNA, commonly a guanosine, via a 5'-5' triphosphate bridge. Accordingly, this structure is often referred to as $m^7GpppG$. The $m^7GpppG$ structure is among others required for translation of the mRNA into the encoded protein.

Cellular mRNAs in higher eukaryotes are further modified at the 5'-end by methylation at the 2'-O position of the first nucleotide after the $m^7Gppp$ moiety. This structure is called cap1 (vs. cap0 for the non-methylated form). While this modification was described more than 40 years ago, its function has remained elusive until recently. Only in 2010 it was first reported that 2'-O methylation of the cap avoids recognition by proteins recognizing the cap0 structure, such as IFIT proteins, especially IFIT1. Binding of IFIT1 to cap0 mRNAs impairs binding of the cap-binding translation initiation eIF4E, which results in decreased translation efficiency.

Synthetic mRNAs are commonly produced by in vitro transcription from a suitable DNA template (e.g., linearized plasmid DNA) using a phage RNA polymerase (mostly T7 or SP6 RNA polymerase). Capped mRNAs can be obtained by in vitro transcription by adding an excess of a cap dinucleotide, e.g., m⁷GpppG, to the reaction. However, it was reported that the cap dinucleotide m⁷GpppG can be incorporated during in vitro transcription in two orientations, from which only one is functional. Therefore, anti-reverse cap analogs (ARCAs) have been developed that cannot be integrated in the reverse orientation due to modifications at either the 2'- or 3'-position of the m⁷guanosine. Consequently, it was demonstrated in rabbit reticulocyte lysate and in dendritic cells that ARCA-capped mRNAs exhibit superior translation efficiency compared to m⁷GpppG-capped RNAs.

In the past decade, ARCAs were further modified in an attempt to stabilize the mRNA against decapping enzymes and to enhance translation efficiency by increasing the affinity for eIF4E. Modifications include various substitutions at the bridging and non-bridging oxygen in the phosphate bridge, extended phosphate groups, and guanosine modifications. The task is complicated by the fact that cap analogs being inert against the decapping enzyme Dcp1-Dcp2 are not always good substrates for the initiation factor and as a result only poorly translated. However, usage of phosphorothioate modified cap analogs at the β-phosphate (beta-S-ARCA or β-S-ARCA) resulted in mRNAs with both increased translation efficiency and elongated half-life in e.g., dendritic cells as compared to ARCA or m⁷GpppG. β-S-ARCA is synthesized as a mixture of two diastereomers, referred to as D1 and D2, based on their elution pattern in HPLC, due to the introduction of a stereogenic P center by the sulfur modification. Interestingly, it was shown that the diastereomers have different biological properties, in particular with respect to the resistance against enzymatic cleavage (such as Dcp2 cleavage) and/or binding to eIF4E. While m⁷GpppG was generally employed in the past, ARCA capped mRNAs are more and more entering preclinical and now also clinical studies.

As modification of the 2'-O position in a cap dinucleotide inhibits incorporation by the phage RNA polymerase (as advantageously used in ARCAs), only cap0 structures can be co-transcriptionally added in vitro using a cap dinucleotide. Capping of in vitro transcribed RNA can also be reached post-transcriptionally using the corresponding enzymes, e.g., from vaccinia virus. Here, a cap1 structure can be obtained. However, the synthesis process then consists of two steps, transcription followed by capping, making it more laborious. Furthermore, the very 5' sequence of the RNAs has a strong influence on the capping efficiency by the enzymes. Also, the method is limited to unmodified caps due to the specificity of the enzymes. Thus, none of the beneficial modifications as described above (e.g., phosphorothioate substitutions) can be incorporated in this manner.

In summary, RNA is especially well-suited for clinical applications. However, the use of RNA in therapy is primarily limited by the short half-life of RNA, in particular in the cytoplasm, and/or the recognition of the RNA by proteins recognizing the cap0 structure, such as IFIT proteins, in particular IFIT1 (thereby impairing the binding of the RNA to eIF4E) both of which result in low and/or insufficient protein expression. Thus, for RNA therapy it is of particular importance to increase RNA stability and/or RNA expression in cells. Thus, it is the object of the present invention to provide RNA which is particularly suited for RNA therapy, i.e., to provide means to particularly stabilize RNA and/or increase RNA expression in cells. This technical problem is solved according to the present invention by the subject-matter of the claims.

SUMMARY OF THE INVENTION

In a first aspect, the present invention provides a 5'-cap compound having the 5'-cap structure according to formula (I):

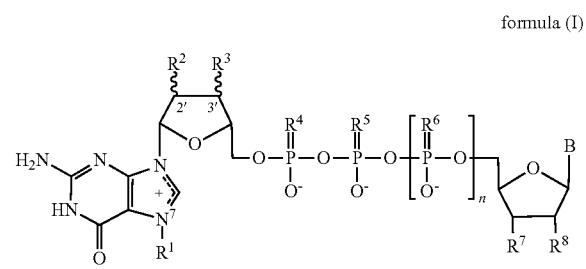

formula (I)

wherein R¹ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl;

R² and R³ are independently selected from the group consisting of H, halo, OH, and optionally substituted alkoxy, or R² and R³ together form O—X—O, wherein X is selected from the group consisting of optionally substituted $CH_2$, optionally substituted $CH_2CH_2$, optionally substituted $CH_2CH_2CH_2$, optionally substituted $CH_2CH(CH_3)$, and optionally substituted $C(CH_3)_2$, or R² is combined with the hydrogen atom at position 4' of the ring to which R² is attached to form —O—CH₂— or —CH₂—O—;

R⁴ and R⁶ are independently selected from the group consisting of O, S, Se, and BH₃;

R⁵ is selected from the group consisting of S, Se, and BH₃;

R⁷ is a mononucleotide or an oligonucleotide having 2 to 9 bases;

R⁸ is H, halo, or optionally substituted alkoxy;

n is 1, 2, or 3; and

B is a purine or pyrimidine base moiety.

In a second aspect, the present invention provides a composition or kit comprising a 5'-cap compound of the first aspect. Such a kit or composition may be used to provide an RNA with a 5'-cap structure of the present invention.

In a third aspect, the present invention provides an RNA which is modified with a 5'-cap compound of the first aspect.

In a fourth aspect, the present invention provides a composition or cell comprising an RNA of the third aspect.

In a particularly preferred embodiment of the third and fourth aspects of the present invention, the RNA further comprises a nucleotide sequence encoding a peptide or protein of interest.

In a fifth aspect, the present invention provides a method for producing a peptide or protein of interest comprising the step of using the RNA of the particularly preferred embodiment of the third aspect or the composition or cell of the particularly preferred embodiment of the fourth aspect.

In a sixth aspect, the present invention provides a method for expressing a peptide or protein of interest in an individual comprising the step of administering to said individual the RNA of the particularly preferred embodiment of the third aspect or the composition or cell of the particularly preferred embodiment of the fourth aspect.

In a seventh aspect, the present invention provides the RNA of the particularly preferred embodiment of the third aspect or the composition or cell of the particularly preferred embodiment of the fourth aspect for use in therapy.

In an eighth aspect, the present invention provides a method of treating a disease or disorder in a subject comprising the step of administering to said subject the RNA of the particularly preferred embodiment of the third aspect or the composition or cell of the particularly preferred embodiment of the fourth aspect. The treatment of the disease or disorder is preferably selected from the group consisting of protein replacement therapy, genome engineering, genetic reprogramming, and immunotherapy.

In a ninth aspect, the present invention provides the RNA of the particularly preferred embodiment of the third aspect or the composition or cell of the particularly preferred embodiment of the fourth aspect for use in a method of treating a disease or disorder in a subject. The treatment of the disease or disorder is preferably selected from the group consisting of protein replacement therapy, genome engineering, genetic reprogramming, and immunotherapy.

In a tenth aspect, the present invention provides a method of increasing the stability of an RNA in cells (such as immature antigen presenting cells) and/or for increasing the expression of an RNA in cells (such as immature antigen presenting cells), said method comprising providing said RNA with the structure according to formula (I) as defined in the first aspect; and transferring said RNA modified with the structure according to formula (I) into the cells.

In an eleventh aspect, the present invention provides a method for providing an RNA with a 5'-cap structure, said method comprising performing a transcription reaction using a template nucleic acid in the presence of a 5'-cap compound of the first aspect.

In further aspects, the present invention provides the following:
- a method for eliciting an immune response in an individual comprising the step of administering to said individual the RNA of the preferred embodiment of the third aspect or the composition (preferably in the form of a vaccine composition) or cell (preferably an immature antigen presenting cell) of the preferred embodiment of the fourth aspect; in one embodiment the method is for eliciting an immune response against a virus, such as against influenza virus (A, B, or C), cytomegalovirus (CMV), or respiratory syncytial virus (RSV);
- a method of increasing a portion of MHC molecules which present an antigen of interest on the surface of an antigen presenting cell, said method comprising providing an RNA comprising a nucleotide sequence encoding a peptide or protein comprising said antigen of interest or an antigen peptide thereof, said RNA being modified with the structure according to formula (I) as defined in the first aspect; and transferring said RNA modified with the structure according to formula (I) into an immature antigen presenting cell; in one embodiment, the antigen of interest is an antigen of a virus (such as influenza virus (A, B, or C), CMV, or RSV) or an antigen peptide thereof;
- a method for stimulating and/or activating immune effector cells, said method comprising providing an RNA comprising a nucleotide sequence encoding a peptide or protein comprising an antigen of interest or an antigen peptide thereof, said RNA being modified with the structure according to formula (I) as defined in the first aspect; transferring said RNA modified with the structure according to formula (I) into immature antigen presenting cells; and contacting the antigen presenting cells with the immune effector cells; in one embodiment, the antigen of interest is an antigen of a virus (such as influenza virus (A, B, or C), CMV, or RSV) or an antigen peptide thereof;
- a method for inducing an immune response in an individual, said method comprising providing an RNA comprising a nucleotide sequence encoding a peptide or protein comprising an antigen of interest or an antigen peptide thereof, said RNA being modified with the structure according to formula (I) as defined in the first aspect; and administering said RNA modified with the structure according to formula (I) to said individual; in one embodiment, the antigen of interest is an antigen of a virus (such as influenza virus (A, B, or C), CMV, or RSV) or an antigen peptide thereof; and
- a method for inducing an immune response in an individual, said method comprising providing an RNA comprising a nucleotide sequence encoding a peptide or protein comprising an antigen of interest or an antigen peptide thereof, said RNA being modified with the structure according to formula (I) as defined in the first aspect; transferring said RNA modified with the structure according to formula (I) into immature antigen presenting cells; and administering the antigen presenting cells to said individual; in one embodiment, the antigen of interest is an antigen of a virus (such as influenza virus (A, B, or C), CMV, or RSV) or an antigen peptide thereof.

Further aspects as well as advantages and novel features of the present invention will become apparent from the following detailed description optionally in conjunction with the accompanying drawings.

BRIEF DESCRIPTION OF THE DRAWINGS

FIG. 4 shows the luciferase signal 6 hours (A), 24 hours (B) or 48 hours (C) after administration.

FIG. 5 shows EPO levels in plasma of mice 6 hours, 24 hours, 48 hours or 72 hours after injection.

DETAILED DESCRIPTION OF THE PRESENT INVENTION

Figure 1:
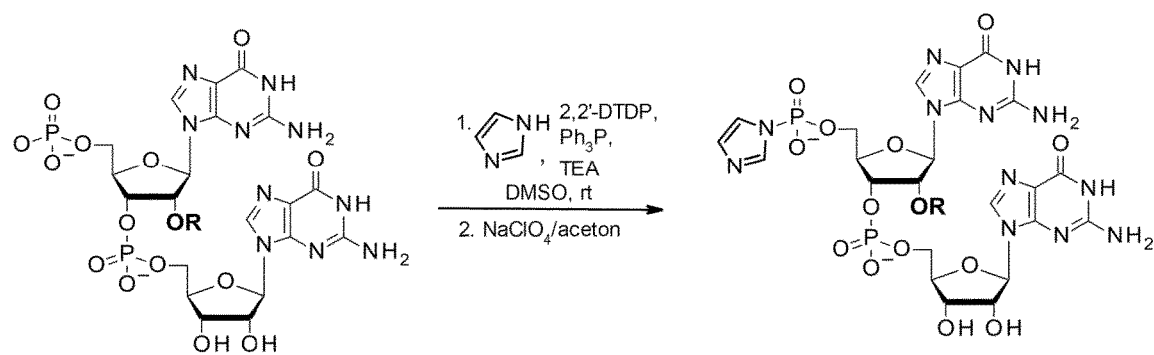
FIG. 1: Synthesis of a P-imidazolide precursor (Im-pm$^{2'}$-$^O$GpG) for synthesis of an exemplary 5'-cap compound of the present invention, m$_2^{7,2'-O}$Gpp$_S$pm$^{2'-O}$GpG (in the following "Compound 1"; OR=OCH$_3$).

Although the present invention is further described in more detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described in more detail. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise. For example, if in a preferred embodiment $R^1$ is methyl and in another preferred embodiment $R^5$ is S, then in a preferred embodiment, $R^1$ is methyl and $R^5$ is S. Likewise, if in a preferred embodiment $R^7$ is *pm$^{2'-O}$GpN and in another preferred embodiment $R^8$ is OCH$_3$, then in a preferred embodiment, $R^7$ is *pm$^{2'-O}$GpN and $R^8$ is OCH$_3$.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, and recombinant DNA techniques which are explained in the literature in the field (cf., e.g., Molecular Cloning: A Laboratory Manual, 2$^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The term "consisting essentially of" means excluding other members, integers or steps of any essential significance. The term "comprising" encompasses the term "consisting essentially of" which, in turn, encompasses the term "consisting of". Thus, at each occurrence in the present application, the term "comprising" may be replaced with the term "consisting essentially of" or "consisting of". Likewise, at each occurrence in the present application, the term "consisting essentially of" may be replaced with the term "consisting of".

The terms "a", "an" and "the" and similar references used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by the context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

According to the invention, the term "nucleic acid" comprises deoxyribonucleic acid (DNA), ribonucleic acid (RNA), combinations thereof, and modified forms thereof. The term comprises genomic DNA, cDNA, mRNA, recombinantly produced and chemically synthesized molecules. According to the invention, a nucleic acid may be present as a single-stranded or double-stranded and linear or covalently circularly closed molecule. A nucleic acid can, according to the invention, be isolated. The term "isolated nucleic acid" means, according to the invention, that the nucleic acid (i) was amplified in vitro, for example via polymerase chain reaction (PCR) for DNA or in vitro transcription (using e.g. an RNA polymerase) for RNA, (ii) was produced recombinantly by cloning, (iii) was purified, for example, by cleavage and separation by gel electrophoresis, or (iv) was synthesized, for example, by chemical synthesis.

In the context of the present invention, the term "DNA" relates to a molecule which comprises deoxyribonucleotide residues and preferably is entirely or substantially composed of deoxyribonucleotide residues. "Deoxyribonucleotide" relates to a nucleotide which lacks a hydroxyl group at the 2'-position of a β-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogs or analogs of naturally occurring DNA.

In the context of the present invention, the term "RNA" relates to a molecule which comprises ribonucleotide residues and preferably is entirely or substantially composed of ribonucleotide residues. "Ribonucleotide" relates to a nucleotide with a hydroxyl group at the 2'-position of a β-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of an RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered/modified nucleotides can be referred to as analogs of naturally occurring nucleotides, and the corresponding RNAs containing such altered/modified nucleotides (i.e., altered/modified RNAs) can be referred to as analogs of naturally occurring RNAs. A molecule is "substantially composed of ribonucleotide residues" if the content of ribonucleotide residues in the molecule is at least 40% (such as at least 45%, at least 50%, at least 55%, at least 60%, at least 65%, at least 70%, at least 75%, at least 80%, at least 85%, at least 90%, at least 95%, at least 96%, at least 97%, at least 98%, at least 99%), based on the total number of nucleotide residues in the molecule. The total number of nucleotide residues in a molecule is the sum of all nucleotide residues (irrespective of whether the nucleotide residues are standard (i.e., naturally occurring) nucleotide residues or analogs thereof). In the context of the present invention, the RNA, preferably the mRNA, is modified with a 5'-cap compound of the present invention and preferably contains one or more further modifications to further stabilize the RNA, as described below.

According to the invention, RNA has a length of at least 20, preferably at least 50, in particular at least 100 nucleotides, such as 100 to 15,000, more preferably 50 to 10,000, more preferably 100 to 5,000, in particular 200 to 1,000 nucleotides. RNA (in particular mRNA) which encodes a peptide or protein preferably has a length of at least 50, more preferably at least 150, in particular at least 200 nucleotides, such as 100 to 15,000, more preferably 50 to 10,000, more preferably 100 to 5,000, in particular 200 to 1,000 nucleotides.

According to the invention, "RNA" includes mRNA, tRNA, rRNA, snRNAs, ssRNA, dsRNAs, and inhibitory RNA, and is preferably mRNA.

According to the invention, "dsRNA" means double-stranded RNA and is RNA with two partially or completely complementary strands.

According to the present invention, the term "mRNA" means "messenger-RNA" and relates to a "transcript" which may be generated by using a DNA template and may encode a peptide or protein. Typically, an mRNA comprises a 5'-UTR, a peptide/protein coding region, and a 3'-UTR. In the context of the present invention, mRNA is preferably generated by in vitro transcription (IVT) from a DNA template. As set forth above, the in vitro transcription methodology is known to the skilled person, and a variety of in vitro transcription kits is commercially available.

mRNA is single-stranded but may contain self-complementary sequences that allow parts of the mRNA to fold and pair with itself to form double helices.

mRNA only possesses limited half-life in cells and in vitro. Thus, according to the invention, the stability and/or translation efficiency of RNA may be modified as required. For example, mRNA may be stabilized and/or its translation increased by one or more modifications having a stabilizing effect and/or increasing translation efficiency of mRNA. Such modifications are described, for example, in WO 2007/036366 the entire disclosure of which is incorporated herein by reference. In order to increase expression of the mRNA according to the present invention, it may be modified within the coding region, i.e., the sequence encoding the expressed peptide or protein, preferably without altering the sequence of the expressed peptide or protein, e.g., to increase the GC-content to increase mRNA stability and to perform a codon optimization and, thus, enhance translation in cells.

RNA can be isolated from cells, can be made from a DNA template, or can be chemically synthesized using methods known in the art. In preferred embodiments, RNA is synthesized in vitro from a DNA template. In one particularly preferred embodiment, RNA, in particular mRNA, is generated by in vitro transcription from a DNA template. The in vitro transcription methodology is known to the skilled person; cf., e.g., Molecular Cloning: A Laboratory Manual, $2^{nd}$ Edition, J. Sambrook et al. eds., Cold Spring Harbor Laboratory Press, Cold Spring Harbor 1989. Furthermore, a variety of in vitro transcription kits is commercially available, e.g., from Thermo Fisher Scientific (such as TranscriptAid™ T7 kit, MEGAscript® T7 kit, MAXIscript®), New England BioLabs Inc. (such as HiScribe™ T7 kit, HiScribe™ T7 ARCA mRNA kit), Promega (such as RiboMAX™, HeLaScribe®, Riboprobe® systems), Jena Bioscience (such as SP6 or T7 transcription kits), and Epicentre (such as AmpliScribe™). In one particularly preferred embodiment, RNA is in vitro transcribed RNA (IVT RNA). For providing modified RNA, correspondingly modified nucleotides, such as modified naturally occurring nucleotides, non-naturally occurring nucleotides and/or modified non-naturally occurring nucleotides, can be incorporated during synthesis (preferably in vitro transcription), or modifications can be effected in and/or added to the RNA after transcription.

RNA according to the present invention is at least modified with a 5'-cap compound of the present invention.

In a preferred embodiment, RNA according to the present invention comprises a nucleic acid sequence encoding a peptide or protein, preferably a pharmaceutically active peptide or protein, and is capable of expressing said peptide or protein, in particular if transferred into a cell or subject. Thus, the RNA according to the present invention preferably contains a coding region (open reading frame (ORF)) encoding a peptide or protein, preferably encoding a pharmaceutically active peptide or protein. In this respect, an "open reading frame" or "ORF" is a continuous stretch of codons beginning with a start codon and ending with a stop codon.

According to the invention, the term "pharmaceutically active peptide or protein" means a peptide or protein that can be used in the treatment of an individual where the expression of a peptide or protein would be of benefit, e.g., in ameliorating the symptoms of a disease or disorder. Preferably, a pharmaceutically active peptide or protein has curative or palliative properties and may be administered to ameliorate, relieve, alleviate, reverse, delay onset of or lessen the severity of one or more symptoms of a disease or disorder. Preferably, a pharmaceutically active peptide or protein has a positive or advantageous effect on the condition or disease state of an individual when administered to the individual in a therapeutically effective amount. A pharmaceutically active peptide or protein may have prophylactic properties and may be used to delay the onset of a disease or disorder or to lessen the severity of such disease or disorder. The term "pharmaceutically active peptide or protein" includes entire proteins or polypeptides, and can also refer to pharmaceutically active fragments thereof. It can also include pharmaceutically active analogs of a peptide or protein.

Specific examples of pharmaceutically active peptides and proteins include, but are not limited to, cytokines, adhesion molecules (in particular integrins), immunoglobulins (e.g., antibodies), immunologically active compounds (e.g., antigens), hormones, growth factors, protease inhibitors (e.g., alpha 1-antitrypsin), enzymes (e.g., herpes simplex virus type 1 thymidine kinase (HSV1-TK), hexosaminidase, phenylalanine hydroxylase, pseudocholinesterase, pancreatic enzymes, and lactase), receptors (e.g., growth factor receptors), apoptosis regulators, transcription factors, tumor suppressor proteins, structural proteins, reprogramming factors, genomic engineering proteins, and blood proteins.

According to the invention, the term "cytokines" relates to proteins which have a molecular weight of about 5 to 20 kDa and which participate in cell signaling (e.g., paracrine, endocrine, and/or autocrine signaling). In particular, when released, cytokines exert an effect on the behavior of cells around the place of their release. Examples of cytokines include lymphokines, interleukins, chemokines, interferons, and tumor necrosis factors (TNFs). According to the present application, cytokines do not include hormones or growth factors. Cytokines differ from hormones in that (i) they usually act at much more variable concentrations than hormones and (ii) generally are made by a broad range of cells (nearly all nucleated cells can produce cytokines). Interferons are usually characterized by antiviral, antiproliferative and immunomodulatory activities. Interferons are proteins that alter and regulate the transcription of genes within a cell by binding to interferon receptors on the regulated cell's surface, thereby preventing viral replication within the cells. The interferons can be grouped into two types. IFN-gamma is the sole type II interferon; all others are type I interferons. Type I and type II interferons differ in gene structure (type II interferon genes have three exons; type I, one), chromosome location (in humans, type II is located on chromosome-12; the type I interferon genes are linked and on chromosome-9), and the types of tissues where they are produced (type I interferons are synthesized ubiquitously, type II by lymphocytes). Type I interferons competitively inhibit each other binding to cellular receptors, while type II interferon has a distinct receptor. According to the invention, the term "interferon" or "IFN" preferably relates to type I interferons, in particular interferon alfa and interferon beta. Particular examples of cytokines include erythropoietin (EPO), colony stimulating factor (CSF), granulocyte colony stimulating factor (G-CSF), granulocyte-macrophage colony stimulating factor (GM-CSF), tumor necrosis factor (TNF), bone morphogenetic protein (BMP), interferon alfa (IFNα), interferon beta (IFNβ), interferon gamma (INFγ), interleukin 2 (IL-2), interleukin 4 (IL-4), interleukin 10 (IL-10), and interleukin 11 (IL-11), According to the invention, the term "hormones" relates to a class of signaling molecules produced by glands, wherein signaling usually includes the following steps: (i) synthesis of a hormone in a particular tissue; (ii) storage and secretion; (iii) transport of the hormone to its target; (iv) binding of the hormone by a receptor; (v) relay and amplification of the signal; and (vi) breakdown of the hormone. Hormones differ from cytokines in that (1) hormones usually act in less variable concentrations and (2) generally are made by specific kinds of cells. Particular examples of hormones include insulin, vasopressin, prolactin, adrenocorticotropic hormone (ACTH), thyroid hormone, growth hormones (such as human grown hormone or bovine somatotropin), oxytocin, atrial-natriuretic peptide (ANP), glucagon, somatostatin, cholecystokinin, gastrin, leptins, catecholamines, gonadotrophines, trophic hormones, and dopamine. In one embodiment, a "hormone" is a peptide or protein hormone, such as insulin, vasopressin, prolactin, adrenocorticotropic hormone (ACTH), thyroid hormone, growth hormones (such as human grown hormone or bovine somatotropin), oxytocin, atrial-natriuretic peptide (ANP), glucagon, somatostatin, cholecystokinin, gastrin, and leptins.

According to the invention, the term "adhesion molecules" relates to proteins which are located on the surface of a cell and which are involved in binding of the cell with other cells or with the extracellular matrix (ECM). Adhesion molecules are typically transmembrane receptors and can be classified as calcium-independent (e.g., integrins, immunoglobulin superfamily, lymphocyte homing receptors) and calcium-dependent (cadherins and selectins). Particular examples of adhesion molecules are integrins, lymphocyte homing receptors, selectins (e.g., P-selectin), and addressins.

Integrins are also involved in signal transduction. In particular, upon ligand binding, integrins modulate cell signaling pathways, e.g., pathways of transmembrane protein kinases such as receptor tyrosine kinases (RTK). Such regulation can lead to cellular growth, division, survival, or differentiation or to apoptosis. Particular examples of integrins include: $\alpha_1\beta_1$, $\alpha_2\beta_1$, $\alpha_3\beta_1$, $\alpha_4\beta_1$, $\alpha_5\beta_1$, $\alpha_6\beta_1$, $\alpha_7\beta_1$, $\alpha_L\beta_2$, $\alpha_M\beta_2$, $\alpha_{IIb}\beta_3$, $\alpha_V\beta_3$, $\alpha_V\beta_3$, $\alpha_V\beta_5$, $\alpha_V\beta_6$, $\alpha_V\beta_8$, and $\alpha_6\beta_4$.

According to the invention, the term "immunoglobulins" or "immunoglobulin superfamily" refers to molecules which are involved in the recognition, binding, and/or adhesion processes of cells. Molecules belonging to this superfamily share the feature that they contain a region known as immunoglobulin domain or fold. Members of the immunoglobulin superfamily include antibodies (e.g., IgA, IgD, IgE, IgG, and IgM), T cell receptors (TCRs), major histocompatibility complex (MHC) molecules, co-receptors (e.g., CD4, CD8, CD19), antigen receptor accessory molecules (e.g., CD-3γ, CD3-δ, CD-3ε, CD79a, CD79b), co-stimulatory or inhibitory molecules (e.g., CD28, CD80, CD86), and other (e.g., CD147, CD90, CD7).

According to the invention, the term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also down-regulate other aspects of the immune response, for example shifting the immune response away from a TH2 immune response, which is useful for treating a wide range of TH2 mediated diseases. Immunologically active compounds can be useful as vaccine adjuvants. Particular examples of immunologically active compounds include interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, selectins, homing receptors, and antigens, in particular tumor-associated antigens, pathogen-associated antigens (such as bacterial, parasitic, or viral antigens (such as one or more (e.g., 1, 2, 3, 4, 5, 6, 7, 8, 9, or 10) antigens of influenza virus (A, B, or C), CMV or RSV)), allergens, and autoantigens.

According to the invention, the term "autoantigen" or "self-antigen" refers to an antigen which originates from within the body of a subject (i.e., the autoantigen can also be called "autologous antigen") and which produces an abnormally vigorous immune response against this normal part of the body. Such vigorous immune reactions against autoantigens may be the cause of "autoimmune diseases".

According to the invention, the term "allergen" refers to a kind of antigen which originates from outside the body of a subject (i.e., the allergen can also be called "heterologous antigen") and which produces an abnormally vigorous immune response in which the immune system of the subject fights off a perceived threat that would otherwise be harmless to the subject. "Allergies" are the diseases caused by such vigorous immune reactions against allergens. An allergen usually is an antigen which is able to stimulate a type-I hypersensitivity reaction in atopic individuals through immunoglobulin E (IgE) responses. Particular examples of allergens include allergens derived from peanut proteins (e.g., Ara h 2.02), ovalbumin, grass pollen proteins (e.g., Phl p 5), and proteins of dust mites (e.g., Der p 2).

According to the invention, the term "growth factors" refers to molecules which are able to stimulate cellular growth, proliferation, healing, and/or cellular differentiation. Typically, growth factors act as signaling molecules between cells. The term "growth factors" include particular cytokines and hormones which bind to specific receptors on the surface of their target cells. Examples of growth factors include bone morphogenetic proteins (BMPs), fibroblast growth factors (FGFs), vascular endothelial growth factors (VEGFs), such as VEGFA, epidermal growth factor (EGF), insulin-like growth factor, ephrins, macrophage colony-stimulating factor, granulocyte colony-stimulating factor, granulocyte macrophage colony-stimulating factor, neuregulins, neurotrophins (e.g., brain-derived neurotrophic factor (BDNF), nerve growth factor (NGF)), placental growth factor (PGF), platelet-derived growth factor (PDGF), renalase (RNLS) (anti-apoptotic survival factor), T-cell growth factor (TCGF), thrombopoietin (TPO), transforming growth factors (transforming growth factor alpha (TGF-α), transforming growth factor beta (TGF-β)), and tumor necrosis factor-alpha (TNF-α). In one embodiment, a "growth factor" is a peptide or protein growth factor.

According to the invention, the term "enzymes" refers to macromolecular biological catalysts which accelerate chemical reactions. Like any catalyst, enzymes are not consumed in the reaction they catalyze and do not alter the equilibrium of said reaction. Unlike many other catalysts, enzymes are much more specific. In one embodiment, an enzyme is essential for homeostasis of a subject, e.g., any malfunction (in particular, decreased activity which may be caused by any of mutation, deletion or decreased production) of the enzyme results in a disease. Examples of enzymes include enzymes of the biosynthesis or degradation of cholesterol, steroidogenic enzymes, kinases, nucleases, phosphodiesterases, methylases, de-methylases, dehydrogenases, cellulases, proteases, lipases, phospholipases, aromatases, cytochromes, adenylate or guanylate cyclases, and neuramidases, such as tissue plasminogen activator, streptokinase, herpes simplex virus type 1 thymidine kinase (HSV1-TK), hexosaminidase, phenylalanine hydroxylase, pseudocholinesterase, pancreatic enzymes (e.g., amylase, lipase, and protease or mixtures thereof (such as pancrelipase)), and lactase.

According to the invention, the term "receptors" refers to protein molecules which receive signals (in particular chemical signals called ligands) from outside a cell. The binding of a signal (e.g., ligand) to a receptor causes some kind of response of the cell, e.g., the intracellular activation of a kinase. Receptors include transmembrane receptors (such as ion channel-linked (ionotropic) receptors, G protein-linked (metabotropic) receptors, and enzyme-linked receptors) and intracellular receptors (such as cytoplasmic receptors and nuclear receptors). Particular examples of receptors include steroid hormone receptors, growth factor receptors, and peptide receptors (i.e., receptors whose ligands are peptides), such as P-selectin glycoprotein ligand-1 (PSGL-1). The term "growth factor receptors" refers to receptors which bind to growth factors. Growth factor receptors are the first step of the signaling cascade for cell differentiation and proliferation. Growth factor receptors may use the JAK/STAT, MAP kinase, and PI3 kinase pathways.

According to the invention, the term "protease inhibitors" refers to molecules, in particular peptides or proteins, which inhibit the function of proteases. Protease inhibitors can be classified by the protease which is inhibited (e.g., aspartic protease inhibitors, cysteine protease inhibitors, metalloprotease inhibitors, serine protease inhibitors, threonine protease inhibitors, trypsin inhibitors) or by their mechanism of action (e.g., suicide inhibitors, such as serpins). Particular examples of protease inhibitors include serpins, such as alpha 1-antitrypsin, aprotinin, and bestatin.

According to the invention, the term "apoptosis regulators" refers to molecules, in particular peptides or proteins, which modulate apoptosis, i.e., which either activate or inhibit apoptosis. Apoptosis regulators can be grouped into two broad classes: those which modulate mitochondrial function and those which regulate caspases. The first class includes proteins (e.g., BCL-2, BCL-xL) which act to preserve mitochondrial integrity by preventing loss of mitochondrial membrane potential and/or release of proapoptotic proteins such as cytochrome C into the cytosol. Also to this first class belong proapoptotic proteins (e.g., BAX, BAK, BIM) which promote release of cytochrome C. The second class includes proteins such as the inhibitors of apoptosis proteins (e.g., XIAP) or FLIP which block the activation of caspases. Particular examples of apoptosis regulators are BAX, BCL-2, BCL-xL, BAK, BIM, XIAP, and FLIP, in particular BAX.

According to the invention, the term "transcription factors" relates to proteins which regulate the rate of transcription of genetic information from DNA to messenger RNA, in particular by binding to a specific DNA sequence. Transcription factors may regulate cell division, cell growth, and cell death throughout life; cell migration and organization during embryonic development; and/or in response to signals from outside the cell, such as a hormone. Transcription factors contain at least one DNA-binding domain which binds to a specific DNA sequence, usually adjacent to the genes which are regulated by the transcription factors. Particular examples of transcription factors include hepatocyte nuclear factors, MECP2, insulin promoter factor 1, FOXP2, FOXP3, the STAT protein family, p53, the HOX protein family, and the SOX proteins, such as SOX2.

According to the invention, the term "tumor suppressor proteins" relates to molecules, in particular peptides or proteins, which protect a cell from one step on the path to cancer. Tumor-suppressor proteins (usually encoded by corresponding tumor-suppressor genes) exhibit a weakening or repressive effect on the regulation of the cell cycle and/or promote apoptosis. Their functions may be one or more of the following: repression of genes essential for the continuing of the cell cycle; coupling the cell cycle to DNA damage (as long as damaged DNA is present in a cell, no cell division should take place); initiation of apoptosis, if the damaged DNA cannot be repaired; metastasis suppression (e.g., preventing tumor cells from dispersing, blocking loss of contact inhibition, and inhibiting metastasis); and DNA repair. Particular examples of tumor-suppressor proteins include p53, phosphatase and tensin homolog (PTEN), SWI/SNF (SWItch/Sucrose Non-Fermentable), von Hippel-Lindau tumor suppressor (pVHL), adenomatous polyposis coli (APC), CD95, suppression of tumorigenicity 5 (ST5), suppression of tumorigenicity 5 (ST5), suppression of tumorigenicity 14 (ST14), and Yippee-like 3 (YPEL3).

According to the invention, the term "structural proteins" refers to proteins which confer stiffness and rigidity to otherwise-fluid biological components. Structural proteins are mostly fibrous (such as collagen and elastin) but may also be globular (such as actin and tubulin). Usually, globular proteins are soluble as monomers, but polymerize to form long, fibers which, for example, may make up the cytoskeleton. Other structural proteins are motor proteins (such as myosin, kinesin, and dynein) which are capable of generating mechanical forces, and surfactant proteins. Particular examples of structural proteins include collagen, fibroin, fibrinogen, surfactant protein A, surfactant protein B, surfactant protein C, surfactant protein D, elastin, tubulin, actin, and myosin.

According to the invention, the term "reprogramming factors" or "reprogramming transcription factors" relates to molecules, in particular peptides or proteins, which, when expressed in somatic cells optionally together with further agents such as further reprogramming factors, lead to reprogramming or de-differentiation of said somatic cells to cells having stem cell characteristics, in particular pluripotency. Particular examples of reprogramming factors include OCT4, SOX2, c-MYC, KLF4, LIN28, and NANOG.

According to the invention, the term "genomic engineering proteins" relates to proteins which are able to insert, delete or replace DNA in the genome of a subject. Particular examples of genomic engineering proteins include meganucleases, zinc finger nucleases (ZFNs), transcription activator-like effector nucleases (TALENs), and clustered regularly spaced short palindromic repeat-CRISPR-associated protein 9 (CRISPR-Cas9).

According to the invention, the term "blood proteins" relates to peptides or proteins which are present in blood plasma of a subject, in particular blood plasma of a healthy subject. Blood proteins have diverse functions such as transport (e.g., albumin, transferrin), enzymatic activity (e.g., thrombin or ceruloplasmin), blood clotting (e.g., fibrinogen), defense against pathogens (e.g., complement components and immunoglobulins), protease inhibitors (e.g., alpha 1-antitrypsin), etc. Particular examples of blood proteins include thrombin, serum albumin, Factor VII, Factor VIII, insulin, Factor IX, Factor X, tissue plasminogen activator, protein C, von Willebrand factor, antithrombin III, glucocerebrosidase, erythropoietin, granulocyte colony stimulating factor (G-CSF), modified Factor VIII, and anticoagulants.

According to the invention, the term "protein replacement therapy" relates to a medical treatment which supplements or replaces a peptide or protein which has a decreased activity in a patient compared to a healthy subject. The decreased activity (including zero activity which may be the case when the peptide or protein is absent in the patient) may be the result of (i) a decreased expression of the peptide or protein (i.e., the peptide or protein is fully functional but the amount thereof is decreased) or (ii) the presence of one or more mutations in the amino acid sequence of the expressed peptide or protein (i.e., the peptide or protein is not fully functional). For example, this decreased activity of the peptide or protein may be the result of a gene encoding the peptide or protein but containing one or more mutations in such a manner that (i) the expression of said gene is decreased or silenced thereby resulting in a decreased amount of the peptide or protein (which may still be fully functional) and/or (ii) the amino acid sequence of the peptide or protein encoded by said gene contains one or more mutations thereby resulting in a non-fully functional (or non-functional) peptide or protein. Diseases or disorders caused by a decreased activity of a peptide or protein in a patient may be treated by replacing or supplementing the peptide or protein (protein replacement therapy), e.g., by administering to a patient having such a disease or disorder an RNA (in particular an RNA of the present invention) comprising a nucleotide sequence encoding the peptide or protein. The nucleotide sequence encoding the peptide or protein may be autologous or heterologous to the patient. However, if the decreased activity of the peptide or protein in a patient is due to one or more mutations (i.e., resulting in a non-fully functional (or non-functional) peptide or protein), it is preferred that the nucleotide sequence encoding the peptide or protein is heterologous to the patient, in particular is obtained from a healthy subject (of the same species) expressing the peptide or protein in its native (i.e., unmutated) form. For example, such protein replacement therapy may comprise the step of administering to a patient (i) an RNA (in particular an RNA of the present invention) comprising a nucleotide sequence encoding said peptide or protein (wherein said nucleotide sequence preferably is heterologous and may be obtained from a healthy subject) or (ii) a composition, e.g., a pharmaceutical composition, comprising such RNA, or alternatively, the steps of (a) transferring an RNA (in particular an RNA of the present invention) comprising a nucleotide sequence encoding said peptide or protein (wherein said nucleotide sequence preferably is heterologous and may be obtained from a healthy subject) into a cell (wherein said cell may be autologous to the patient) and (b) administering said transfected cell to the patient. In alternative (i), the RNA is preferably taken up into cells (e.g., antigen-presenting cells, such as monocytes, macrophages, or dendritic cells, or other cells), and a translation product of the nucleotide sequence encoding a peptide or protein is formed (and optionally posttranslationally modified) to yield the peptide or protein. In alternative (ii), after administration of the transfected cells to the patient, the transfected cells preferably express the peptide or protein.

The term "genome engineering" relates to the process in which DNA is inserted, deleted or replaced in the genome of a subject, preferably by using genomic engineering proteins. Particular examples of genomic engineering proteins include meganucleases, zinc finger nucleases (ZFNs), transcription activator-like effector nucleases (TALENs), and clustered regularly spaced short palindromic repeat-CRISPR-associated protein 9 (CRISPR-Cas9).

The term "genetic reprogramming" refers to the resetting of the genetic program of a cell. A reprogrammed cell preferably exhibits pluripotency.

In one embodiment, the pharmaceutically active peptide or protein is a disease-associated peptide or protein, i.e., it is causatively linked with a disease or disorder.

For example, a disease or disorder may be caused by a decreased activity of a peptide or protein. The decreased activity may be the result of (i) a decreased expression of the peptide or protein (i.e., the peptide or protein is fully functional but the amount thereof is decreased) or (ii) the presence of one or mutations in the amino acid sequence of the expressed peptide or protein (i.e., the peptide or protein is not fully functional). For example, this decreased activity of the peptide or protein may be the result of a gene encoding the peptide or protein but containing one or mutations in such a manner that (i) the expression of said gene is decreased or silenced thereby resulting in a decreased amount of the peptide or protein (which may still be fully functional) and/or (ii) the amino acid sequence of the peptide or protein encoded by said gene contains one or more mutations thereby resulting in a non-fully functional (or non-functional) peptide or protein. Such diseases or disorders caused by a decreased activity of a peptide or protein in a patient may be treated by replacing or supplementing the peptide or protein (protein replacement therapy), e.g., by administering to a patient having such a disease or disorder an RNA (in particular an RNA of the present invention) comprising a nucleotide sequence encoding the peptide or protein. The nucleotide sequence encoding the peptide or protein may be autologous or heterologous to the patient. However, if the decreased activity of the peptide or protein in a patient is due to one or more mutations (i.e., resulting in a non-fully functional (or non-functional) peptide or protein), it is preferred that the nucleotide sequence encoding the peptide or protein is heterologous, in particular obtained from a healthy subject (of the same species) expressing the peptide or protein in its native (i.e., unmutated) form. For example, such protein replacement therapy may comprise the step of administering to the patient (i) an RNA (in particular an RNA of the present invention) comprising a nucleotide sequence encoding said peptide or protein (wherein said nucleotide sequence preferably is heterologous and may be obtained from a healthy subject) or (ii) a composition, e.g., a pharmaceutical composition, comprising such RNA, or alternatively, the steps of (a) transferring an RNA (in particular an RNA of the present invention) comprising a nucleotide sequence encoding said peptide or protein (wherein said nucleotide sequence preferably is heterologous and may be obtained from a healthy subject) into a cell (wherein said cell may be autologous to the patient) and (b) administering said transfected cell to the patient. In alternative (i), the RNA is preferably taken up into cells (e.g., antigen-presenting cells, such as monocytes, macrophages, or dendritic cells, or other cells), and a translation product of the nucleotide sequence encoding a peptide or protein is formed (and optionally posttranslationally modified) to yield the peptide or protein. In alternative (ii), after administration of the transfected cells to the patient, the transfected cells preferably express the peptide or protein.

Alternatively, such diseases or disorders caused by a decreased activity of a peptide or protein in a patient may be treated by using genome engineering, e.g., by replacing the DNA sequence encoding the peptide or protein (i.e., resulting in a non-fully functional (or non-functional) peptide or protein) in a patient having such a disease or disorder with a DNA sequence encoding the peptide or protein in its native (i.e., unmutated) form. For example, such genome engineering therapy may comprise the step of administering to a patient (i) an RNA (in particular an RNA of the present invention) comprising a nucleotide sequence encoding a genomic engineering protein and (ii) a DNA comprising a nucleotide sequence encoding the peptide or protein in its native (i.e., unmutated) form. Upon administration, preferably, the RNA comprising a nucleotide sequence encoding a genomic engineering protein and the DNA comprising a nucleotide sequence encoding the peptide or protein in its native (i.e., unmutated) form are taken up into cells (in particular diseased cells), a translation product of the nucleotide sequence encoding a genomic engineering protein is formed (and optionally posttranslationally modified) to yield the genomic engineering protein, and the genomic engineering protein together with the DNA sequence encoding the peptide or protein in its native (i.e., unmutated) form act to replace the mutated DNA sequence in the genome of the cells with the DNA sequence encoding the peptide or protein in its native (i.e., unmutated) form.

In a further alternative, such diseases or disorders caused by a decreased activity of a peptide or protein in a patient may be treated by using genetic reprogramming, e.g., by reprogramming somatic cells (in particular autologous somatic cells) of a patient having such as disease or disorder and administering said reprogrammed cells to the patient. This therapeutic approach may be particularly beneficial in patients having a disease or disorder which causes a depletion or extinction of cells producing the desired peptide or protein (e.g., a hormone such as insulin). For example, such genetic reprogramming therapy may comprise the steps of (a) introducing an RNA (in particular an RNA of the present invention) comprising a nucleotide sequence encoding one or more reprogramming factors into somatic cells; (b) allowing the development of cells having stem cell characteristics; and (c) administering the cells having stem cell characteristics to a patient. In a preferred embodiment, the somatic cells are autologous to the patient. Upon administration, the cells having stem cell characteristics preferably differentiate into cells expressing the desired peptide or protein.

In one embodiment, the pharmaceutically active peptide or protein, such as the disease-associated peptide or protein, is a cytokine, preferably selected from the group consisting of erythropoietin (EPO), interleukin 4 (IL-2), and interleukin 10 (IL-11), more preferably EPO. A disease or disorder caused by a decreased activity of a cytokine or a disease or disorder, wherein increasing the amount of a cytokine (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the cytokine), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is an adhesion molecule, in particular an integrin. A disease or disorder caused by a decreased activity of an adhesion molecule or a disease or disorder, wherein increasing the amount of an adhesion molecule (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the adhesion molecule), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a hormone, in particular vasopressin, insulin or growth hormone. A disease or disorder caused by a decreased activity of a hormone or a disease or disorder, wherein increasing the amount of a hormone (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the hormone), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a growth factor, in particular VEGFA. A disease or disorder caused by a decreased activity of a growth factor or a disease or disorder, wherein increasing the amount of a growth factor (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the growth factor), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is an enzyme, preferably selected from the group consisting of herpes simplex virus type 1 thymidine kinase (HSV1-TK), hexosaminidase, phenylalanine hydroxylase, pseudocholinesterase, pancreatic enzymes, and lactase. A disease or disorder caused by a decreased activity of an enzyme or a disease or disorder, wherein increasing the amount of an enzyme (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the enzyme), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a receptor, in particular growth factor receptors. A disease or disorder caused by a decreased activity of a receptor or a disease or disorder, wherein increasing the amount of a receptor (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the receptor), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is an apoptosis regulator, in particular BAX. A disease or disorder caused by a decreased activity of an apoptosis regulator or a disease or disorder, wherein increasing the amount of an apoptosis regulator (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the apoptosis regulator), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a tumor suppressor protein, in particular p53. A disease or disorder caused by a decreased activity of a tumor suppressor protein or a disease or disorder, wherein increasing the amount of a tumor suppressor protein (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the tumor suppressor protein), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a structural protein, in particular surfactant protein B. A disease or disorder caused by a decreased activity of a structural protein or a disease or disorder, wherein increasing the amount of a structural protein (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the structural protein), a corresponding genome engineering therapy as described herein, and/or a genetic reprogramming therapy as described herein.

A patient having such a disease or disorder or being at risk of developing such a disease or disorder can be treated accordingly.

In one embodiment, the pharmaceutically active peptide or protein, such as the disease-associated peptide or protein, is a transcription factor, in particular FOXP3. A disease or disorder caused by a decreased activity of a transcription factor or a disease or disorder, wherein increasing the amount of a transcription factor (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the transcription factor), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a reprogramming factor, e.g., OCT4, SOX2, c-MYC, KLF4, LIN28 and NANOG. A disease or disorder caused by a decreased activity of a reprogramming factor or a disease or disorder, wherein increasing the amount of a reprogramming factor (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the reprogramming factor), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a genomic engineering protein, in particular clustered regularly spaced short palindromic repeat-CRISPR-associated protein 9 (CRISPR-Cas9). A disease or disorder caused by a decreased activity of a genomic engineering protein or a disease or disorder, wherein increasing the amount of a genomic engineering protein (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the genomic engineering protein), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein, such as the disease-associated peptide or protein, is a blood protein, in particular fibrinogen or alpha 1-antitrypsin. A disease or disorder caused by a decreased activity of a blood protein or a disease or disorder, wherein increasing the amount of a blood protein (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the blood protein), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein is an immunoglobulin, in particular an antibody. A disease or disorder caused by a decreased activity of an immunoglobulin or a disease or disorder, wherein increasing the amount of an immunoglobulin (i) ameliorates, relieves, alleviates, or reverses one or more symptoms of the disease or disorder are and/or (ii) delays the onset of the disease or disorder and/or (iii) lessens the severity of the disease or disorder, may be treated by a corresponding protein replacement therapy as described herein (e.g., by replacing or supplementing the immunoglobulin), a corresponding genome engineering therapy as described herein, and/or a genetic reprogramming therapy as described herein. A patient having such a disease or disorder or being at risk of developing such a disease or disorder can be treated accordingly.

In one embodiment, the pharmaceutically active peptide or protein is an immunologically active compound, in particular an antigen, such as a disease-associated antigen. Thus, another example of disease-associated peptides or proteins is a disease-associated antigen, i.e., an antigen which is characteristic for a disorder or disease and which is under normal conditions, i.e., in a healthy individual, specifically expressed in a limited number of organs and/or tissues or in specific developmental stages (for example, the disease-associated antigen may be under normal conditions specifically expressed in non-vital tissue, in reproductive organs, e.g., in testis, in trophoblastic tissue, e.g., in placenta, or in germ line cells) and is expressed or aberrantly expressed in one or more diseased tissues. In this context, "a limited number" preferably means not more than 3, more preferably not more than 2 or 1. Particular examples of a disease-associated antigen are tumor-associated antigens, pathogen-associated antigens (e.g., antigens of a virus (such as influenza virus (A, B, or C), CMV or RSV)) and allergens. A disease or disorder which is characterized by a disease-associated antigen may be treated by eliciting an immune response against said disease-associated antigen in a patient having, or being at risk of developing, said disease or disorder. E.g., in case the disease-associated antigen is a tumor-associated antigen, the immunotherapy may be considered as cancer immunotherapy; in case the disease-associated antigen is a pathogen-associated antigen (e.g., an antigen of a virus (such as influenza virus (A, B, or C), CMV or RSV)), the immunotherapy can be considered as pathogen immunotherapy; and in case the disease-associated antigen is an allergen, the immunotherapy can be considered allergy tolerization therapy, respectively. Thus, the RNA of the present invention may be used to produce a disease-associated antigen which vaccinates an individual against a malignant disease or an infectious disease or may be used to produce an allergen which leads to allergy tolerization.

The term "immunotherapy" relates to a treatment preferably involving a specific immune reaction and/or immune effector function(s).

As used herein, "de-differentiation" refers to loss of specialization in form or function. In cells, de-differentiation leads to a less committed cell. The term "committed" refers to cells which are considered to be permanently committed to a specific function. Committed cells are also referred to as "terminally differentiated cells".

As used herein, "differentiation" refers to the adaptation of cells for a particular form or function. In cells, differentiation leads to a more committed cell.

A "differentiated cell" is a mature cell that has undergone progressive developmental changes to a more specialized form or function. Cell differentiation is the process a cell undergoes as it matures to an overtly specialized cell type. Differentiated cells have distinct characteristics, perform specific functions, and are less likely to divide than their less differentiated counterparts.

An "undifferentiated" cell, for example, an immature, embryonic, or primitive cell, typically has a nonspecific appearance, may perform multiple, non-specific activities, and may perform poorly, if at all, in functions typically performed by differentiated cells.

"Somatic cell" refers to any and all differentiated cells and does not include stem cells, germ cells, or gametes. Preferably, "somatic cell" as used herein refers to a terminally differentiated cell.

A "stem cell" is a cell with the ability to self-renew, to remain undifferentiated, and to become differentiated. A stem cell can divide without limit, for at least the lifetime of the animal in which it naturally resides. A stem cell is not terminally differentiated; it is not at the end stage of a differentiation pathway. When a stem cell divides, each daughter cell can either remain a stem cell or embark on a course that leads toward terminal differentiation.

The term "cells having stem cell characteristics" is used herein to designate cells which, although they are derived from differentiated somatic non-stem cells, exhibit one or more features typical for stem cells, in particular embryonic stem cells. Such features include an embryonic stem cell morphology such as compact colonies, high nucleus to cytoplasm ratio and prominent nucleoli, normal karyotypes, expression of telomerase activity, expression of cell surface markers that are characteristic for embryonic stem cells, and/or expression of genes that are characteristic for embryonic stem cells. The cell surface markers that are characteristic for embryonic stem cells are, for example, selected from the group consisting of stage-specific embryonic antigen-3 (SSEA-3), SSEA-4, tumor-related antigen-1-60 (TRA-1-60), TRA-1-81, and TRA-2-49/6E. The genes that are characteristic for embryonic stem cells are selected, for example, from the group consisting of endogenous OCT4, endogenous NANOG, growth and differentiation factor 3 (GDF3), reduced expression 1 (REX1), fibroblast growth factor 4 (FGF4), embryonic cell-specific gene 1 (ESG1), developmental pluripotency-associated 2 (DPPA2), DPPA4, and telomerase reverse transcriptase (TERT). In one embodiment, the one or more features typical for stem cells include pluripotency. In one embodiment, the cells having stem cell characteristics exhibit a pluripotent state. In one embodiment, the cells having stem cell characteristics have the developmental potential to differentiate into advanced derivatives of all three primary germ layers. In one embodiment, the primary germ layer is endoderm and the advanced derivative is gut-like epithelial tissue. In a further embodiment, the primary germ layer is mesoderm and the advanced derivative is striated muscle and/or cartilage. In an even further embodiment, the primary germ layer is ectoderm and the advanced derivative is neural tissue and/or epidermal tissue. In one preferred embodiment, the cells having stem cell characteristics have the developmental potential to differentiate into cells expressing the peptide or protein of interest. According to the invention, generally the terms "cells having stem cell characteristics", "cells having stem cell properties", "reprogrammed cells" and "de-differentiated cells" or similar terms have similar meanings and are used interchangeably herein.

In one embodiment, RNA, in particular RNA which comprises a nucleic acid sequence encoding a peptide or protein and which is to be expressed in a cell, is a single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes which in one embodiment, if the RNA is viral RNA, may partially or completely replace viral sequences such as viral sequences encoding structural proteins.

The term "nucleoside" (abbreviated herein as "N") relates to compounds which can be thought of as nucleotides without a phosphate group. While a nucleoside is a nucleobase linked to a sugar (e.g., ribose or deoxyribose), a nucleotide is composed of a nucleoside and one or more phosphate groups. Examples of nucleosides include cytidine, uridine, pseudouridine, adenosine, and guanosine.

The five standard nucleosides which usually make up naturally occurring nucleic acids are uridine, adenosine, thymidine, cytidine and guanosine. The five nucleosides are commonly abbreviated to their one letter codes U, A, T, C and G, respectively. However, thymidine is more commonly written as "dT" ("d" represents "deoxy") as it contains a 2'-deoxyribofuranose moiety rather than the ribofuranose ring found in uridine. This is because thymidine is found in deoxyribonucleic acid (DNA) and not ribonucleic acid (RNA). Conversely, uridine is found in RNA and not DNA. The remaining three nucleosides may be found in both RNA and DNA. In RNA, they would be represented as A, C and G, whereas in DNA they would be represented as dA, dC and dG.

A modified purine (A or G) or pyrimidine (C, T, or U) base moiety is preferably modified by one or more alkyl groups, more preferably one or more $C_{1-4}$ alkyl groups, even more preferably one or more methyl groups. Particular examples of modified purine or pyrimidine base moieties include $N^7$-alkyl-guanine, $N^6$-alkyl-adenine, 5-alkyl-cytosine, 5-alkyl-uracil, and N(1)-alkyl-uracil, such as $N^7$—$C_{1-4}$ alkyl-guanine, $N^6$—$C_{1-4}$ alkyl-adenine, 5-$C_{1-4}$ alkyl-cytosine, 5-$C_{1-4}$ alkyl-uracil, and N(1)-$C_{1-4}$ alkyl-uracil, preferably $N^7$-methyl-guanine, N'-methyl-adenine, 5-methyl-cytosine, 5-methyl-uracil, and N(1)-methyl-uracil.

The term "in vitro transcription" or "IVT" as used herein means that the transcription (i.e., the generation of RNA) is conducted in a cell-free manner. I.e., IVT does not use living/cultured cells but rather the transcription machinery extracted from cells (e.g., cell lysates or the isolated components thereof, including an RNA polymerase (preferably T7, T3 or SP6 polymerase)).

The term "modification" in the context of modified RNA (preferably mRNA) according to the present invention includes any modification of an RNA (preferably mRNA) which is not naturally present in said RNA. In particular, the term modification relates to providing an RNA (preferably mRNA) with a 5'-cap structure of the present invention. For example, providing an RNA (preferably mRNA) with a 5'-cap structure of the present invention may be achieved by in vitro transcription of a DNA template in presence of a 5'-cap compound of the present invention, wherein said 5'-cap structure is co-transcriptionally incorporated into the generated RNA strand, or the RNA (preferably mRNA) may be generated, for example, by in vitro transcription, and the 5'-cap structure may be attached to the RNA post-transcriptionally using capping enzymes, for example, capping enzymes of vaccinia virus.

The RNA (preferably mRNA) may comprise further modifications in order to, e.g., increase its stability and/or decrease immunogenicity and/or decrease cytotoxicity. For example, a further modification of the RNA, preferably mRNA, modified with a 5'-cap compound of the present invention may be an extension or truncation of the naturally occurring poly(A) tail, an alteration of the 5'- or 3'-untranslated regions (UTR) such as introduction of a UTR which is not related to the coding region of said RNA, the replacement of one or more naturally occurring nucleotides with synthetic nucleotides and/or codon optimization (e.g., to alter, preferably increase, the GC content of the RNA).

RNA (preferably mRNA) having an unmasked poly-A sequence is translated more efficiently than RNA (preferably mRNA) having a masked poly-A sequence. The term "poly (A) tail" or "poly-A sequence" relates to a sequence of adenosine (in particular adenylyl) (A) residues which typically is located on the 3'-end of an RNA (preferably mRNA) molecule and "unmasked poly-A sequence" means that the poly-A sequence at the 3' end of an RNA (preferably mRNA) molecule ends with an A of the poly-A sequence and is not followed by nucleotides other than A located at the 3' end, i.e., downstream, of the poly-A sequence. Furthermore, a long poly-A sequence having a length of about 120 nucleotides results in an optimal transcript stability and translation efficiency of an RNA (preferably mRNA).

Therefore, in order to increase stability and/or expression of RNA, preferably mRNA, according to the present invention, it may be modified so as to be present in conjunction with a poly-A sequence, preferably having a length of 10 to 500, more preferably 30 to 300, even more preferably 65 to 200 and especially 100 to 150 adenosine (in particular adenylyl) residues. In an especially preferred embodiment the poly-A sequence has a length of approximately 120 adenosine (in particular adenylyl) residues. To further increase stability and/or expression of RNA, preferably of the mRNA, according to the invention, the poly-A sequence can be unmasked.

In addition, incorporation of a 3'-UTR into the 3'-non translated region of an RNA (preferably mRNA) molecule can result in an enhancement in translation efficiency. A synergistic effect may be achieved by incorporating two or more of such 3'-UTRs (which are preferably arranged in a head-to-tail orientation; cf., e.g., Holtkamp et al., Blood 108, 4009-4017 (2006)). The 3'-UTRs may be autologous or heterologous to the RNA (preferably mRNA) into which they are introduced. In one particular embodiment the 3'-UTR is derived from a globin gene or mRNA, such as a gene or mRNA of alpha2-globin, alpha1-globin, or beta-globin, preferably beta-globin, more preferably human beta-globin. For example, the RNA (preferably mRNA) may be modified by the replacement of the existing 3'-UTR with or the insertion of one or more, preferably two copies of a 3'-UTR derived from a globin gene, such as alpha2-globin, alpha1-globin, beta-globin, preferably beta-globin, more preferably human beta-globin.

The RNA (preferably mRNA) according to the invention may have modified ribonucleotides in order to increase its stability and/or decrease immunogenicity and/or decrease cytotoxicity. For example, in one embodiment, in the RNA (preferably mRNA) according to the invention 5-methylcytidine is substituted partially or completely, preferably completely, for cytidine. Alternatively or additionally, in one embodiment, in the RNA (preferably mRNA) according to the invention pseudouridine or N(1)-methylpseudouridine or 5-methyluridine is substituted partially or completely, preferably completely, for uridine. An RNA (preferably mRNA) which is modified by pseudouridine (substituting partially or completely, preferably completely, for uridine) is referred to herein as "Ψ-modified", whereas the term "m1Ψ-modified" means that the RNA (preferably mRNA) contains N(1)-methylpseudouridine (substituting partially or completely, preferably completely, for uridine). Furthermore, the term "m5U-modified" means that the RNA (preferably mRNA) contains 5-methyluridine (substituting partially or completely, preferably completely, for uridine). Such Ψ- or m1Ψ- or m5U-modified RNAs of the invention usually exhibit decreased immunogenicity compared to their unmodified forms and, thus, are preferred in applications where the induction of an immune response is to be avoided or minimized (e.g., in protein replacement therapy, genome engineering therapy, and genetic reprogramming therapy, as described herein).

A combination of the above described modifications, i.e., incorporation of a poly-A sequence, unmasking of a poly-A sequence, incorporation of one or more 3'-UTRs and replacing one or more naturally occurring nucleotides with synthetic nucleotides (e.g., 5-methylcytidine for cytidine and/or pseudouridine (Ψ) or N(1)-methylpseudouridine (m1Ψ) or 5-methyluridine (m5U) for uridine), has a synergistic influence on the stability of RNA (preferably mRNA) and increase in translation efficiency. Thus in a preferred embodiment, the RNA (preferably mRNA) according to the present invention is not only modified with a 5'-cap compound of the present invention but also contains a combination of the three above-mentioned modifications, i.e., (i) incorporation of a poly-A sequence, unmasking of a poly-A sequence; (ii) incorporation of one or more 3'-UTRs; and (iii) replacing one or more naturally occurring nucleotides with synthetic nucleotides (e.g., 5-methylcytidine for cytidine and/or pseudouridine (Ψ) or N(1)-methylpseudouridine (m1Ψ) or 5-methyluridine (m5U) for uridine). Optionally, the codons of the RNA (preferably mRNA) of the present invention may further be optimized, e.g., to increase the GC content of the RNA and/or to replace codons which are rare in the cell (or subject) in which the peptide or protein of interest is to be expressed by codons which are synonymous frequent codons in said cell (or subject).

The term "RNA polymerase" as used herein refers to a DNA-dependent RNA polymerase which produces primary transcript RNA. Examples of RNA polymerases suitable for generating IVT RNA according to the present invention include T7, T3 and SP6 RNA polymerases. A preferred RNA polymerase is T7 RNA polymerase.

The term "conventional 5'-cap" refers to a cap structure found on the 5'-end of an mRNA molecule and generally consists of a guanosine 5'-triphosphate (Gppp) which is connected via its triphosphate moiety to the 5'-end of the next nucleotide of the mRNA (i.e., the guanosine is connected via a 5' to 5' triphosphate linkage to the rest of the mRNA). The guanosine may be methylated at position $N^7$ (resulting in the cap structure $m^7$Gppp).

According to the present application, the term "cap0" means the structure "$m^7$GpppN", wherein N is any nucleoside bearing an OH moiety at position 2'. According to the present application, the term "cap1" means the structure "$m^7$GpppNm", wherein Nm is any nucleoside bearing an $OCH_3$ moiety at position 2'. According to the present application, the term "cap2" means the structure "m⁷GpppNmNm", wherein each Nm is independently any nucleoside bearing an OCH$_3$ moiety at position 2'.

In the context of the present invention, the term "5'-cap structure of the present invention" is a 5'-cap analog that resembles the structure of a conventional 5'-cap but is modified to possess the ability to stabilize RNA (in particular mRNA) and/or increase RNA expression (in particular mRNA expression), if attached thereto, preferably in vivo or in a cell. The cell may be any cell which can be transfected with RNA (preferably mRNA) of the present invention and is preferably a cell obtained from a subject, e.g., a stem cell (e.g., a mesenchymal stem cell (MSC)) or an antigen presenting cell (e.g., an immature antigen presenting cell), such as a dendritic cell (e.g., an immature dendritic cell). Preferably, the 5'-cap structure of the present invention at least comprises the structure "1-(N$^7$—(R')-guanine-9-yl)-pentose-5-yl-(phosphorothioate linkage)-N(R$^{8'}$)—" of any one of formulas (I), (Ia), (Tb), (Ic), (Id), (Ie), (II), (IIa), (IIb), (IIc), (IId), (IIe), (III), and (IIIa) (i.e., wherein the first guanine of the 5'-cap structure is substituted at position N$^7$ with R$^1$ and is connected at N$^9$ to C$^{1'}$ of the pentose bearing substituents R$^2$ and R$^3$; the phosphorothioate linkage has the structure —O—P(O$^-$)(R$^4$)—O—P(O$^-$)(R$^5$)—O[—P(O$^-$)(R$^6$)—O]$_n$; and N is any nucleoside bearing base B and being substituted at position 2' with R'). Furthermore, if R$^7$ in any one of formulas (I), (Ia), (Ib), (Ic), (Id), (Ie), (II), (IIa), (IIb), (IIc), (IId), (IIe), (III), and (IIIa) is a ribooligonucleotide, in which the OH group at position 2' of at least the ribose at the 5'-end of the ribooligonucleotide is replaced with a substituent R$^{8'}$ selected from the group consisting of H, halo, and optionally substituted alkoxy, and the ribose at the 3'-end of the ribooligonucleotide has a free OH group at position 2', then the 5'-cap structure of the present invention preferably comprises in addition to the structure "1-(N$^7$—(R')-guanine-9-yl)-pentose-5-yl-(phosphorothioate linkage)-N(R$^8$)—" of any one of formulas (I), (Ia), (Ib), (Ic), (Id), (Ie), (II), (IIa), (IIb), (IIc), (IId), (IIe), (III), and (IIIa) also any nucleoside substituted at position 2' with R$^{8'}$ (together with any internucleotide linkage between the N(R$^8$) moiety and the N(R$^{8'}$) moiety as well as any internucleotide linkage between each pair of N(R$^{8'}$) moieties in case the ribooligonucleotide contains more than one N(R$^8$) moiety). For example, if for providing a 5'-cap structure of the present invention a 5'-cap compound of formula (I), wherein R$^7$ is a ribooligonucleotide of the formula [pN(R')]$_2$pN (i.e., only the nucleoside at the 3'-end of the ribooligonucleotide has a free OH group at position 2', whereas the two other nucleosides are substituted with R$^{8'}$ at position 2') is used, the 5'-cap structure of the present invention would comprises at least the structure "1-(N$^7$—(R')-guanine-9-yl)-pentose-5-yl-(phosphorothioate linkage)-N(R$^8$)-[pN(R$^8$)]$_2$".

According to the present application, the term "5'-capped RNA" means RNA which contains at its 5'-end a cap structure.

Within the context of the present application, the term "RNA which is modified with a 5'-cap compound of the present invention" means RNA which contains at its 5'-end a 5'-cap structure of the present invention. Similarly, the term "mRNA which is modified with a 5'-cap compound of the present invention" means mRNA which contains at its 5'-end a 5'-cap structure of the present invention. Thus, in a preferred embodiment, such RNA (e.g., mRNA) modified with a 5'-cap compound of the present invention at least comprises at its 5'-end the structure "1-(N$^7$—(R')-guanine-9-yl)-pentose-5-yl-(phosphorothioate linkage)-N(R')—" of any one of formulas (I), (Ia), (Ib), (Ic), (Id), (Ie), (II), (IIa), (IIb), (IIc), (IId), (IIe), (III), and (IIIa) (i.e., wherein the first guanine of the 5'-cap structure is substituted at position N$^7$ with R$^1$ and is connected at N$^9$ to C$^{1'}$ of the pentose bearing substituents R$^2$ and R$^3$; the phosphorothioate linkage has the structure —O—P(O$^-$)(R$^4$)—O—P(O$^-$)(R$^5$)—O—[—P(O$^-$)(R$^6$)—O]$_n$; and N is any nucleoside bearing base B and being substituted at position 2' with R'). Furthermore, if R$^7$ in any one of formulas (I), (Ia), (Ib), (Ic), (Id), (Ie), (II), (IIa), (IIb), (IIc), (IId), (IIe), (III), and (IIIa) is a ribooligonucleotide, in which the OH group at position 2' of at least the ribose at the 5'-end of the ribooligonucleotide is replaced with a substituent R$^{8'}$ selected from the group consisting of H, halo, and optionally substituted alkoxy, and the ribose at the 3'-end of the ribooligonucleotide has a free OH group at position 2', then the RNA (such as mRNA) which is modified with a 5'-cap compound of the present invention preferably comprises at its 5'-end in addition to the structure "1-(N$^7$—(R$^1$)-guanine-9-yl)-pentose-5-yl-(phosphorothioate linkage)-N(R$^1$)—" of any one of formulas (I), (Ia), (Ib), (Ic), (Id), (Ie), (II), (IIa), (IIb), (IIc), (IId), (IIe), (III), and (IIIa) also any nucleoside substituted at position 2' with R$^{8'}$ (together with any internucleotide linkage between the N(R') moiety and the N(R$^{8'}$) moiety as well as any internucleotide linkage between each pair of N(R$^{8'}$) moieties in case the ribooligonucleotide contains more than one N(R') moiety). For example, if an RNA is modified with a 5'-cap compound of the present invention of formula (I), wherein R$^7$ is a ribooligonucleotide of the formula [pN(R$^{8'}$)]$_2$pN (i.e., only the nucleoside at the 3'-end of the ribooligonucleotide has a free OH group at position 2', whereas the two other nucleosides are substituted with R$^{8'}$ at position 2'), the modified RNA would comprises at its 5'-end at least the structure "1-(N$^7$—(R$^1$)-guanine-9-yl)-pentose-5-yl-(phosphorothioate linkage)-N(R$^8$)-[pN(R$^8$)]$_2$".

The term "increasing RNA expression", preferably in connection with an RNA modified with a 5'-cap compound of the present invention, preferably means decreasing or even inhibiting the recognition of the RNA by proteins recognizing a cap0 structure, e.g., IFIT proteins (in particular IFIT1).

According to the invention, a part or fragment of a peptide or protein preferably has at least one functional property of the peptide or protein from which it has been derived. Such functional properties comprise a pharmacological activity, the interaction with other peptides or proteins, an enzymatic activity, the interaction with antibodies, and the selective binding of nucleic acids. E.g., a pharmacological active fragment of a peptide or protein has at least one of the pharmacological activities of the peptide or protein from which the fragment has been derived. A part or fragment of a peptide or protein preferably comprises a sequence of at least 6, in particular at least 8, at least 10, at least 12, at least 15, at least 20, at least 30 or at least 50, consecutive amino acids of the peptide or protein. A part or fragment of a peptide or protein preferably comprises a sequence of up to 8, in particular up to 10, up to 12, up to 15, up to 20, up to 30 or up to 55, consecutive amino acids of the peptide or protein.

According to the invention, an analog of a peptide or protein is a modified form of said peptide or protein from which it has been derived and has at least one functional property of said peptide or protein. E.g., a pharmacological active analog of a peptide or protein has at least one of the pharmacological activities of the peptide or protein from which the analog has been derived. Such modifications include any chemical modification and comprise single or multiple substitutions, deletions and/or additions of any molecules associated with the protein or peptide, such as carbohydrates, lipids and/or proteins or peptides. In one embodiment, "analogs" of proteins or peptides include those modified forms resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "analog" also extends to all functional chemical equivalents of said proteins and peptides.

In the context of the present invention, the term "vaccine composition" relates to an antigenic preparation which comprises RNA. The vaccine composition is administered to an individual in order to stimulate the humoral and/or cellular immune system of the individual against one or more antigens. In this context, the RNA may encode the antigen, a protein or peptide comprising said antigen or an antigen peptide. A vaccine composition in the context of the present invention may further comprise one or more adjuvants and/or excipients and is applied to an individual in any suitable route in order to elicit a protective and/or therapeutic immune reaction against the antigen.

An "antigen" according to the invention covers any substance that will elicit an immune response and/or any substance against which an immune response or an immune mechanism such as a cellular response is directed. This also includes situations wherein the antigen is processed into antigen peptides and an immune response or an immune mechanism is directed against one or more antigen peptides, in particular if presented in the context of MHC molecules. In particular, an "antigen" relates to any substance, preferably a peptide or protein, that reacts specifically with antibodies or T-lymphocytes (T-cells). According to the present invention, the term "antigen" comprises any molecule which comprises at least one epitope, such as a T cell epitope. Preferably, an antigen in the context of the present invention is a molecule which, optionally after processing, induces an immune reaction, which is preferably specific for the antigen (including cells expressing the antigen).

According to the present invention, any suitable antigen may be used, which is a candidate for an immune response, wherein the immune response may be both a humoral as well as a cellular immune response. In the context of some embodiments of the present invention, the antigen is preferably presented by a cell, preferably by an antigen presenting cell, in the context of MHC molecules, which results in an immune response against the antigen. An antigen is preferably a product which corresponds to or is derived from a naturally occurring antigen. Such naturally occurring antigens may include or may be derived from allergens, viruses (e.g., influenza virus (A, B, or C), CMV, or RSV), bacteria, fungi, parasites and other infectious agents and pathogens or an antigen may also be a tumor antigen. According to the present invention, an antigen may correspond to a naturally occurring product, for example, a viral protein (e.g., a protein of influenza virus A, influenza virus B, or influenza virus C, such as PB1, PB1-F2, PB2, PA, HA, NP, NA, M1, M2, NS1, or NEP/NS2 from influenza virus A, influenza virus B, or influenza virus C), or a part thereof.

In a preferred embodiment, the antigen is a tumor antigen, i.e., a part of a tumor cell which may be derived from the cytoplasm, the cell surface or the cell nucleus, in particular those which primarily occur intracellularly or as surface antigens of tumor cells. For example, tumor antigens include the carcinoembryonal antigen, α1-fetoprotein, isoferritin, and fetal sulphoglycoprotein, α2-H-ferroprotein and γ-fetoprotein, as well as various virus tumor antigens. According to the present invention, a tumor antigen preferably comprises any antigen which is characteristic for tumors or cancers as well as for tumor or cancer cells with respect to type and/or expression level. In another embodiment, the antigen is a pathogen-associated antigen, i.e., an antigen derived from a pathogen, e.g., from a virus (such as influenza virus (A, B, or C), CMV, or RSV), bacterium, unicellular organism, or parasite, for example a virus antigen such as viral ribonucleoprotein or coat protein. In particular, the antigen should be presented by MHC molecules which results in modulation, in particular activation of cells of the immune system, preferably $CD4^+$ and $CD8^+$ lymphocytes, in particular via the modulation of the activity of a T-cell receptor.

In some embodiments, the antigen is a tumor antigen and the present invention involves the stimulation of an antitumor CTL response against tumor cells expressing such tumor antigen and preferably presenting such tumor antigen with class I MHC.

The term "immunogenicity" relates to the relative effectivity of an antigen to induce an immune reaction.

The term "pathogen" relates to pathogenic microorganisms and comprises viruses, bacteria, fungi, unicellular organisms, and parasites. Examples for pathogenic viruses are human immunodeficiency virus (HIV), influenza virus (e.g., influenza virus A, influenza virus B, or influenza virus C), respiratory syncytial virus (RSV), cytomegalovirus (CMV), herpes virus (HSV), hepatitis A-virus (HAV), HBV, HCV, papilloma virus, and human T-lymphotrophic virus (HTLV), such as HIV, CMV, HSV, HAV, HBV, HCV, papilloma virus, and HTLV, preferably influenza virus, CMV, or RSV. Unicellular organisms comprise plasmodia trypanosomes, amoeba, etc.

Thus, in another preferred embodiment, the antigen is one or more (e.g., 1, 2, 3, 4, 5, 6, 7, 8, 9, or 10) viral antigens, i.e., one or more (e.g., 1, 2, 3, 4, 5, 6, 7, 8, 9, or 10) antigens of a virus, wherein the virus is preferably influenza virus (A, B, or C), CMV, or RSV. Hence, in this embodiment, the present invention preferably involves eliciting an immune response against said virus. The one or more viral antigens are preferably selected from the group consisting of PB1, PB1-F2, PB2, PA, HA, NP, NA, M1, M2, NS1, and NEP/NS2 from influenza A, influenza B, or influenza C.

Examples for antigens that may be used in the present invention are p53, ART-4, BAGE, ss-catenin/m, Bcr-abL CAMEL, CAP-1, CASP-8, CDC27/m, CDK4/m, CEA, CLAUDIN-12, c-MYC, CT, Cyp-B, DAM, ELF2M, ETV6-AML1, G250, GAGE, GnT-V, Gap100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, -2, -3, NA88-A, NF1, NY-ESO-1, NY-BR-1, p190 minor BCR-abL, Plac-1, Pm1/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE and WT, preferably WT-1.

"A portion or fragment of an antigen" or "an antigen peptide" according to the invention preferably is an incomplete representation of an antigen and is capable of eliciting an immune response against the antigen or cells characterized by expression of the antigen and preferably by presentation of the antigen.

In this context, the invention also makes use of peptides comprising amino acid sequences derived from antigens, also termed "antigen peptides" herein. By "antigen peptide" or "antigen peptide derived from an antigen" is meant an oligopeptide or polypeptide comprising an amino acid sequence substantially corresponding to the amino acid sequence of a fragment or peptide of an antigen. An antigen peptide may be of any length.

Preferably, the antigen peptides are capable of stimulating an immune response, preferably a cellular response against the antigen or cells characterized by expression of the antigen and preferably by presentation of the antigen. Preferably, an antigen peptide is capable of stimulating a cellular response against a cell characterized by presentation of an antigen with class I MHC and preferably is capable of stimulating an antigen-responsive CTL. Preferably, according to the invention, the antigen peptides are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the invention comprises an amino acid sequence substantially corresponding to the amino acid sequence of such fragment and is processed to produce such fragment, i.e., an MHC class I and/or class II presented peptide derived from an antigen.

If an antigen peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly is derived from the amino acid sequence of an antigen, i.e., its sequence substantially corresponds and is preferably completely identical to a fragment of an antigen.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing is derived from the amino acid sequence of an antigen, i.e., its sequence substantially corresponds and is preferably completely identical to a fragment of an antigen. Thus, an antigen peptide according to the invention in one embodiment comprises a sequence of 7-20 amino acids in length, more preferably 7-12 amino acids in length, more preferably 8-11 amino acids in length, in particular 9 or 10 amino acids in length which substantially corresponds and is preferably completely identical to a fragment of an antigen and following processing of the antigen peptide makes up the presented peptide. However, the antigen peptide may also comprise a sequence which substantially corresponds and preferably is completely identical to a fragment of an antigen which is even longer than the above stated sequence. In one embodiment, an antigen peptide may comprise the entire sequence of an antigen.

Peptides having amino acid sequences substantially corresponding to a sequence of a peptide which is presented by the class I MHC may differ at one or more residues that are not essential for TCR recognition of the peptide as presented by the class I MHC, or for peptide binding to MHC. Such substantially corresponding peptides are also capable of stimulating an antigen-responsive CTL. Peptides having amino acid sequences differing from a presented peptide at residues that do not affect TCR recognition but improve the stability of binding to MHC may improve the immunogenicity of the antigen peptide, and may be referred to herein as "optimized peptide". Using existing knowledge about which of these residues may be more likely to affect binding either to the MHC or to the TCR, a rational approach to the design of substantially corresponding peptides may be employed. Resulting peptides that are functional are contemplated as antigen peptides.

In one embodiment, an antigen peptide when presented in the context of MHC such as MHC of antigen presenting cells is recognized by a T cell receptor. The antigen peptide if recognized by a T cell receptor may be able to induce in the presence of appropriate co-stimulatory signals, clonal expansion of the T cell carrying the T cell receptor specifically recognizing the antigen peptide. Preferably, antigen peptides, in particular if presented in the context of MHC molecules, are capable of stimulating an immune response, preferably a cellular response against the antigen from which they are derived or cells characterized by expression of the antigen and preferably characterized by presentation of the antigen.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

Terms such as "epitope", "T cell epitope", "fragment of an antigen", "immunogenic peptide" and "antigen peptide" are used interchangeably herein and preferably relate to an incomplete representation of an antigen which is preferably capable of eliciting an immune response against the antigen or a cell expressing or comprising and preferably presenting the antigen. Preferably, the terms relate to an immunogenic portion of an antigen. Preferably, it is a portion of an antigen that is recognized (i.e., specifically bound) by a T cell receptor, in particular if presented in the context of MHC molecules. Certain preferred immunogenic portions bind to an MHC class I or class II molecule.

The term "target" shall mean an agent such as a cell or tissue which is a target for an immune response such as a cellular immune response. Targets include cells that present an antigen or an antigen epitope, i.e. a peptide fragment derived from an antigen. In one embodiment, the target cell is a cell expressing an antigen and preferably presenting said antigen with class I MHC.

The term "portion" refers to a fraction. With respect to a particular structure such as an amino acid sequence or protein the term "portion" thereof may designate a continuous or a discontinuous fraction of said structure.

The terms "part" and "fragment" are used interchangeably herein and refer to a continuous element. For example, a part of a structure such as an amino acid sequence or protein refers to a continuous element of said structure.

"Antigen processing" refers to the degradation of an antigen into processing products which are fragments of said antigen (e.g., the degradation of a protein into peptides) and the association of one or more of these fragments (e.g., via binding) with MHC molecules for presentation by cells, preferably antigen-presenting cells to specific T-cells.

By "antigen-responsive CTL" is meant a CD8⁺ T-cell that is responsive to an antigen or a peptide derived from said antigen, which is presented with class I MHC on the surface of antigen presenting cells.

According to the invention, CTL responsiveness may include sustained calcium flux, cell division, production of cytokines such as IFN-γ and TNF-α, up-regulation of activation markers such as CD44 and CD69, and specific cytolytic killing of tumor antigen expressing target cells. CTL responsiveness may also be determined using an artificial reporter that accurately indicates CTL responsiveness.

The terms "immune response" and "immune reaction" are used herein interchangeably in their conventional meaning and refer to an integrated bodily response to an antigen and preferably refers to a cellular immune response, a humoral immune response, or both. According to the invention, the term "immune response to" or "immune response against" with respect to an agent such as an antigen, cell or tissue, relates to an immune response such as a cellular response directed against the agent. An immune response may comprise one or more reactions selected from the group consisting of developing antibodies against one or more antigens and expansion of antigen-specific T-lymphocytes, preferably CD4⁺ and CD8⁺ T-lymphocytes, more preferably CD8⁺ T-lymphocytes, which may be detected in various proliferation or cytokine production tests in vitro.

The terms "inducing an immune response" and "eliciting an immune response" and similar terms in the context of the present invention refer to the induction of an immune response, preferably the induction of a cellular immune response, a humoral immune response, or both. The immune response may be protective/preventive/prophylactic and/or therapeutic. The immune response may be directed against any immunogen or antigen or antigen peptide, preferably against a tumor-associated antigen or a pathogen-associated antigen (e.g., an antigen of a virus (such as influenza virus (A, B, or C), CMV or RSV)). "Inducing" in this context may mean that there was no immune response against a particular antigen or pathogen before induction, but it may also mean that there was a certain level of immune response against a particular antigen or pathogen before induction and after induction said immune response is enhanced. Thus, "inducing the immune response" in this context also includes "enhancing the immune response". Preferably, after inducing an immune response in an individual, said individual is protected from developing a disease such as an infectious disease or a cancerous disease or the disease condition is ameliorated by inducing an immune response.

The terms "cellular immune response", "cellular response", "cell-mediated immunity" or similar terms are meant to include a cellular response directed to cells characterized by expression of an antigen and/or presentation of an antigen with class I or class II MHC. The cellular response relates to cells called T cells or T lymphocytes which act as either "helpers" or "killers". The helper T cells (also termed CD4⁺ T cells) play a central role by regulating the immune response and the killer cells (also termed cytotoxic T cells, cytolytic T cells, CD8⁺ T cells or CTLs) kill cells such as diseased cells.

The term "humoral immune response" refers to a process in living organisms wherein antibodies are produced in response to agents and organisms, which they ultimately neutralize and/or eliminate. The specificity of the antibody response is mediated by T and/or B cells through membrane-associated receptors that bind antigen of a single specificity. Following binding of an appropriate antigen and receipt of various other activating signals, B lymphocytes divide, which produces memory B cells as well as antibody secreting plasma cell clones, each producing antibodies that recognize the identical antigenic epitope as was recognized by its antigen receptor. Memory B lymphocytes remain dormant until they are subsequently activated by their specific antigen. These lymphocytes provide the cellular basis of memory and the resulting escalation in antibody response when re-exposed to a specific antigen.

The term "antibody" as used herein, refers to an immunoglobulin molecule, which is able to specifically bind to an epitope on an antigen. In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3, the CDRs of a VL are termed LCDR1, LCDR2 and LCDR3. The variable regions of the heavy and light chains contain a binding domain that interacts with an antigen. The constant regions of an antibody comprise the heavy chain constant region (CH) and the light chain constant region (CL), wherein CH can be further subdivided into constant domain CHi, a hinge region, and constant domains $CH_2$ and $CH_3$ (arranged from amino-terminus to carboxy-terminus in the following order: $CH_1$, $CH_2$, $CH_3$). The constant regions of the antibodies may mediate the binding of the immunoglobulin to host tissues or factors, including various cells of the immune system (e.g., effector cells) and the first component (Clq) of the classical complement system. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and F(ab)₂, as well as single chain antibodies and humanized antibodies.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, $V_H$ (variable heavy chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The terms "vaccination" and "immunization" describe the process of treating an individual for therapeutic or prophylactic reasons and relate to the procedure of administering one or more immunogen(s) or antigen(s) or derivatives thereof, in particular in the form of RNA coding therefor, as described herein to an individual and stimulating an immune response against said one or more immunogen(s) or antigen(s) or cells characterized by presentation of said one or more immunogen(s) or antigen(s).

By "cell characterized by presentation of an antigen" or "cell presenting an antigen" or "MHC molecules which present an antigen on the surface of an antigen presenting cell" or similar expressions is meant a cell such as a diseased cell, in particular a tumor cell, or an antigen presenting cell presenting the antigen or an antigen peptide, either directly or following processing, in the context of MHC molecules, preferably MHC class I and/or MHC class II molecules, most preferably MHC class I molecules.

In the context of the present invention, terms such as "protect", "prevent", "prophylactic", "preventive", or "protective" relate to the prevention or treatment or both of the occurrence and/or the propagation of a disease in an individual and, in particular, to minimizing the chance that an individual will develop a disease or to delaying the development of a disease. For example, a person at risk for a disease would be a candidate for therapy to prevent a disease. A prophylactic administration of an agent (e.g., RNA) or composition (such as a pharmaceutical composition, e.g., a vaccine composition) described herein can protect the recipient from the development of a disease, e.g., from an infection by a pathogen (e.g., a virus, such as influenza virus (A, B, or C), CMV or RSV) or from the dissemination or metastasis of existing tumors. A therapeutic administration of an agent (e.g., RNA) or composition (such as a pharmaceutical composition) described herein may lead to the inhibition of the progress/growth of the disease. This comprises the deceleration of the progress/growth of the disease, in particular a disruption of the progression of the disease, which preferably leads to elimination of the disease.

The term "adjuvant" relates to compounds which when administered in combination with an antigen, an antigen peptide, or a nucleic acid (such as RNA, preferably mRNA) encoding said antigen or antigen peptide to an individual prolongs or enhances or accelerates the immune response. In the context of the present invention, RNA (preferably mRNA) may be administered with any adjuvants. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B-cells, macrophages, dendritic cells, T-cells and unspecific activation of immune cells. For example, compounds which allow the maturation of the DCs, e.g. lipopolysaccharides or CD40 ligand, form a class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides (Krieg et al., 1995, Nature 374: 546-549) can optionally also be used in this context. Further types of adjuvants include oil emulsions (e.g., Freund's adjuvants), mineral compounds (such as alum), bacterial products (such as *Bordetella pertussis* toxin), liposomes, immune-stimulating complexes, cytokines (e.g., monokines, lymphokines, interleukins or chemokines, such as IL-1, IL-2, IL-3, IL-4, IL-5, IL-6, IL-7, IL-8, IL-9, IL-10, IL-12, IFN-α, IFN-γ, GM-CSF, LT-α, or growth factors, e.g. hGH), lipopeptides (e.g., Pam3Cys). In case the RNA (preferably mRNA) of the invention in one embodiment may encode an immunostimulating agent and said immunostimulating agent encoded by said RNA is to act as the primary immunostimulant, however, only a relatively small amount of CpG DNA is necessary (compared with immunostimulation with only CpG DNA). Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides, and various water-in-oil emulsions which are prepared from biologically degradable oils such as squalene and/or tocopherol. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFN-α, IFN-γ, GM-CSF, LT-α, growth factors, e.g. hGH or lipopeptides, such as Pam3Cys, all of which are suitable for use as adjuvants in the pharmaceutical compositions of the present invention or when RNA of the present invention is used in therapy.

Terms such as "increasing", "enhancing", or "prolonging" preferably relate to an increase, enhancement, or prolongation by about at least 10%, preferably at least 20%, preferably at least 30%, more preferably at least 40%, more preferably at least 50%, even more preferably at least 80%, and most preferably at least 100%. These terms may also relate to an increase, enhancement, or prolongation from zero or a non-measurable or non-detectable level to a level of more than zero or a level which is measurable or detectable.

Terms such as "decreasing", "reducing" or "inhibiting" relate to the ability to cause an overall decrease, preferably of 5% or greater, 10% or greater, 20% or greater, more preferably of 50% or greater, and most preferably of 75% or greater, in the level. This also includes a complete or essentially complete decrease, i.e. a decrease to zero or essentially to zero.

Terms such as "transferring", "transfecting" or "introducing into cells" are used interchangeably herein and relate to the introduction of nucleic acids, in particular exogenous or heterologous nucleic acids, preferably RNA (such as mRNA) into a cell. According to the present invention, the cell can form part of an organ, a tissue and/or an organism. The introduction of nucleic acids, in particular exogenous or heterologous nucleic acids, preferably RNA (such as mRNA) into a cell can be performed in vivo or in vitro.

"Antigen-presenting cells" (APCs) are cells which display antigen, in particular peptide fragments of protein antigens, in association with MHC molecules on their cell surface. T cells may recognize this complex using their T cell receptor (TCR). Antigen-presenting cells process antigens and present them to T cells. An antigen presenting cell includes, but is not limited to, monocytes/macrophages, B cells and dendritic cells (DCs). In a preferred embodiment, the APCs according to the present invention are mammalian, preferably human, mouse, or rat.

Non-professional antigen-presenting cells do not constitutively express the MHC class II proteins required for interaction with naive T cells; these are expressed only upon stimulation of the non-professional antigen-presenting cells by certain cytokines such as IFNγ.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells.

The main types of professional antigen-presenting cells are dendritic cells, which have the broadest range of antigen presentation, and are probably the most important antigen-presenting cells, macrophages, B-cells, and certain activated epithelial cells.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of immunity.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e. g. CD54 and CD11) and costimulatory molecules (e. g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

The term "immunoreactive cell" or "effector cell" in the context of the present invention relates to a cell which exerts effector functions during an immune reaction. An "immunoreactive cell" preferably is capable of binding an antigen or a cell characterized by expression and/or presentation of an antigen or an antigen peptide derived from an antigen and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably CD4+ and/or CD8+ T cells.

Preferably, an "immunoreactive cell" recognizes an antigen or an antigen peptide derived from an antigen with some degree of specificity, in particular if presented in the context of MHC molecules such as on the surface of antigen presenting cells or diseased cells such as tumor cells. Preferably, said recognition enables the cell that recognizes an antigen or an antigen peptide derived from said antigen to be responsive or reactive. If the cell is a helper T cell ($CD4^+$ T cell) bearing receptors that recognize an antigen or an antigen peptide derived from an antigen in the context of MHC class II molecules such responsiveness or reactivity may involve the release of cytokines and/or the activation of $CD8^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an antigen peptide derived from an antigen and are responsive or reactive are also termed "antigen-responsive CTL" herein. If the cell is a B cell such responsiveness may involve the release of immunoglobulins.

The term "T cell" or "T lymphocyte" relates to thymus-derived cells that participate in a variety of cell-mediated immune reactions and includes T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen-presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal immunoglobulin (Ig)-variable (V) domain, one Ig-constant (C) domain, a transmembrane/cell membrane-spanning region, and a short cytoplasmic tail at the C-terminal end. The variable domain of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

The term "peripheral blood mononuclear cell" or "PBMC" relates to a peripheral blood cell having a round nucleus. These cells consist of lymphocytes (T cells, B cells, NK cells) and monocytes, whereas erythrocytes and platelets have no nuclei, and granulocytes (neutrophils, basophils, and eosinophils) have multi-lobed nuclei. These cells can be extracted from whole blood using ficoll and gradient centrifugation, which will separate the blood into a top layer of plasma, followed by a layer of PBMCs and a bottom fraction of polymorphonuclear cells (such as neutrophils and eosinophils) and erythrocytes.

The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPAI, HLA-DPB1, HLA-DQA1, HLA-DQB1, HLA-DRA, and HLA-DRB1.

In one preferred embodiment of all aspects of the invention relating to immunotherapy or immune responses, an MHC molecule is an HLA molecule.

The term "immune effector functions" or "effector functions" in the context of the present invention includes any functions mediated by components of the immune system that result, for example, in the killing of cells. Preferably, the immune effector functions in the context of the present invention are T cell mediated effector functions. Such functions comprise in the case of a helper T cell (CD4+ T cell) the recognition of an antigen or an antigen peptide derived from an antigen in the context of MHC class II molecules by T cell receptors, the release of cytokines and/or the activation of CD8+ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "immune effector cells" in the context of the present invention relates to cells which exert effector functions during an immune reaction. "Immune effector cells" preferably are capable of binding an antigen or a cell characterized by presentation of an antigen and mediating an immune response. For example, such cells secrete cytokines and/or chemokines, kill microbes, secrete antibodies, recognize infected or cancerous cells, and optionally eliminate such cells. For example, immune effector cells comprise T-cells (cytotoxic T-cells, helper T-cells, tumor infiltrating T-cells), B-cells, natural killer cells, neutrophils, macrophages, and dendritic cells. Preferably, in the context of the present invention, "immune effector cells" are T-cells, preferably CD4+ and/or CD8+ cells.

Preferably, an "immune effector cell" recognizes an antigen or an antigen peptide derived from said antigen with some degree of specificity, in particular if presented in the context of MHC molecules such as on the surface of antigen presenting cells or diseased cells such as tumor cells. Preferably, said recognition enables the cell that recognizes an antigen or an antigen peptide derived from said antigen to be responsive. If the cell is a helper T-cell (CD4+ T-cell) bearing receptors that recognize an antigen or an antigen peptide derived from said antigen in the context of MHC class II molecules such responsiveness may involve the release of cytokines and/or the activation of CD8+ lymphocytes (CTLs) and/or B-cells. If the cell is a CTL such responsiveness may involve the elimination of cells presented in the context of MHC class I molecules, i.e., cells characterized by presentation of an antigen with class I MHC, for example, via apoptosis or perforin-mediated cell lysis. Such CTL that recognizes an antigen or an antigen peptide derived from said antigen and are responsive are also termed "antigen-responsive CTL" herein. If the cell is a B-cell such responsiveness may involve the release of immunoglobulins.

The term "half-life" relates to the period of time which is needed to eliminate half of the activity, amount, or number of molecules. In the context of the present invention, the half-life of an RNA (preferably mRNA) is indicative for the stability of said RNA. The half-life of RNA may influence the "duration of expression" of the RNA. It can be expected that RNA having a long half-life will be expressed for an extended time period.

Of course, if according to the present invention it is desired to decrease stability and/or translation efficiency of RNA, it is possible to modify RNA so as to interfere with the function of elements as described above increasing the stability and/or translation efficiency of RNA.

The terms "patient", "individual", "subject", or "animal" are used interchangeably and relate to vertebrates. For example, vertebrates in the context of the present invention are mammals, birds (e.g., poultry), reptiles, amphibians, bony fishes, and cartilaginous fishes, in particular domesticated animals of any of the foregoing as well as animals in captivity such as animals of zoos, and are preferably mammals. Mammals in the context of the present invention include, but are not limited to, humans, non-human primates, domesticated mammals, such as dogs, cats, sheep, cattle, goats, pigs, horses etc., laboratory mammals such as mice, rats, rabbits, guinea pigs, etc. as well as mammals in captivity such as mammals of zoos. The term "animal" as used herein also includes humans. The term "subject" may also include a patient, i.e., an animal, preferably a human having a disease, preferably a disease as described herein.

According to the invention, the term "chronic patient" or "long-term patient" refers to a patient having a chronic disease or disorder. A "chronic disease or disorder" is a disease or disorder which is persistent and/or whose effects (e.g., symptoms) are persistent for at least 3 weeks, such as at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the patient.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant, or malignant.

Preferably, a tumor disease according to the invention is a cancer disease, i.e., a malignant disease, and a tumor cell is a cancer cell. Preferably, a tumor disease is characterized by cells in which an antigen, i.e., a tumor antigen, is expressed or abnormally expressed. Preferably, a tumor disease or a tumor cell is characterized by presentation of a tumor antigen with class I MHC.

"Abnormal expression" means according to the invention that expression is altered, preferably increased, compared to the state in a healthy individual. An increase in expression refers to an increase by at least 10%, in particular at least 20%, at least 50% or at least 100%. In one embodiment, expression is only found in a diseases tissue, while expression in a healthy tissue is repressed.

Preferably, a tumor disease according to the invention is cancer, wherein the term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term "cancer" according to the invention also comprises cancer metastases.

In one embodiment, the RNA according to the invention is (modified) RNA, in particular (modified) mRNA, encoding a peptide or protein. According to the invention, the term "RNA encoding a peptide or protein" means that the RNA, if present in the appropriate environment, preferably within a cell, can direct the assembly of amino acids to produce, i.e., express, the peptide or protein during the process of translation. Preferably, RNA (such as mRNA) according to the invention is able to interact with the cellular translation machinery allowing translation of the peptide or protein.

"Encoding" refers to the inherent property of specific sequences of nucleotides in a nucleic acid to serve as templates for synthesis of other polymers and macromolecules in biological processes having either a defined sequence of nucleotides or a defined sequence of amino acids. Thus, a nucleic acid encodes a protein if expression (translation and optionally transcription) of the nucleic acid produces the protein in a cell or other biological system.

The term "expression" is used according to the invention in its most general meaning and comprises the production of RNA and/or peptides or proteins, e.g., by transcription and/or translation. With respect to RNA, the term "expression" or "translation" relates in particular to the production of peptides or proteins. It also comprises partial expression of nucleic acids. Moreover, expression can be transient or stable.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector". According to the present invention, the RNA used in the present invention may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the invention is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The cDNA containing vector template may comprise vectors carrying different cDNA inserts which following transcription results in a population of different RNA molecules optionally capable of expressing different peptides or proteins or may comprise vectors carrying only one species of cDNA insert which following transcription only results in a population of one RNA species capable of expressing only one peptide or protein. Thus, it is possible to produce RNA capable of expressing a single peptide or protein only or to produce compositions of different RNAs such as RNA libraries and whole-cell RNA capable of expressing more than one peptide or protein, e.g., a composition of peptides or proteins. The present invention envisions the introduction of all such RNA into cells.

The term "vector" as used herein includes any vectors known to the skilled person including plasmid vectors, cosmid vectors, phage vectors such as lambda phage, viral vectors such as adenoviral or baculoviral vectors, retro- or lentiviral vectors, transposons or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

The nucleic acid encoding a peptide or protein can be cloned into a number of types of vectors. However, the present invention should not be construed to be limited to any particular vector. Instead, the present invention should be construed to encompass a wide plethora of vectors which are readily available and well-known in the art. In specific embodiments, the vector is selected from the group consisting of a viral vector, a bacterial vector, and a mammalian cell vector. Many such systems are commercially and widely available.

The vector may be provided to a cell in the form of a viral vector. Viral vector technology is well known in the art. Viruses, which are useful as vectors include, but are not limited to, retroviruses, adenoviruses, adeno-associated viruses, herpes viruses, and lentiviruses. Preferably, the virus is helper-dependent adenovirus (HD-Ad). In general, a suitable vector contains an origin of replication functional in at least one organism, a promoter sequence, convenient restriction endonuclease sites, and one or more selectable markers.

Those of skill in the art of molecular biology generally know how to use promoters, enhancers, and cell type combinations for protein expression. The promoters employed may be constitutive, tissue-specific, inducible, and/or useful under the appropriate conditions to direct high level expression of the introduced nucleic acid segment encoding a peptide or protein. The promoter may be heterologous or endogenous. Constitutive promoter sequences which may be used according to the invention, include, but are not limited to the immediate early cytomegalovirus (CMV) promoter sequence, the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In order to assess the expression of a peptide or protein, the expression vector to be introduced into a cell can also contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the cells. Useful selectable markers are known in the art and include, for example, antibiotic-resistance genes, such as neo and the like. Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the nucleic acid has been introduced into the recipient cells. Suitable reporter genes may include genes encoding luciferase, beta-galactosidase, chloramphenicol acetyl transferase, secreted alkaline phosphatase, or the green fluorescent protein gene.

The vector can be readily introduced into a cell by any method in the art. For example, the expression vector can be transferred into a cell by physical, chemical or biological means. Physical methods for introducing a nucleic acid into a cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York), and Ausubel et al. (1997, Current Protocols in Molecular Biology, John Wiley & Sons, New York).

Biological methods for introducing a nucleic acid of interest into a cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like.

Chemical means for introducing a nucleic acid into a cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a cell or otherwise increase the cellular level of a peptide or protein in a cell, in order to confirm the presence and/or amount of the peptide or protein or its encoding nucleic acid in the cell, a variety of assays may be performed. Such assays include, for example, Southern and Northern blotting, RT-PCR and PCR and assays for detecting the presence or absence of a particular peptide, e.g., by immunological means (ELISAs and Western blots).

The term "cell" means any cell that can be transfected with RNA (preferably mRNA), wherein the RNA to be transfected is preferably exogenous or heterologous RNA. A cell may be obtained from any subject and in one embodiment may be obtained from a patient having a disorder or disease. If the cell is obtained from a patient having a disorder or disease, the cell may contain genetic material which is homologous to the RNA to be introduced but which results in a peptide or protein having decreased activity. The decreased activity may be the result of (i) a decreased expression of the peptide or protein (i.e., the peptide or protein is fully functional but the amount thereof is decreased) or (ii) the presence of one or more mutations in the amino acid sequence of the expressed peptide or protein (i.e., the peptide or protein is not fully functional). For example, such homologous genetic material which results in a peptide or protein having decreased activity may be a gene containing one or more mutations in such a manner that (i) the expression of said gene containing one or more mutations is decreased or silenced thereby resulting in a decreased amount of the fully functional peptide or protein and/or (ii) the amino acid sequence of the peptide or protein encoded by said gene contains one or more mutations thereby resulting in a not fully functional (or non-functional) peptide or protein.

In case the fully functional peptide or protein is expressed in the cell or patient but in an amount too low to maintain the functions of the cell or patient (e.g., leading to the development of a disease or disorder in the patient in which the cell is contained), a therapy to replace or supplement said peptide or protein (protein replacement therapy) would be beneficial. Such protein replacement therapy may comprise the step of administering an RNA comprising a nucleotide sequence encoding said peptide or protein (or a composition, such as a pharmaceutical composition, comprising such RNA) to the patient, or alternatively, the steps of (a) transferring an RNA comprising a nucleotide sequence encoding said peptide or protein into a cell (which may be obtained from the patient) and (b) administering said transfected cell to the patient.

In case the decreased activity of a peptide or protein in a patient (and thus, the development of a disease or disorder) is due to the presence of one or more mutations in the amino acid sequence of said peptide or protein (i.e., the peptide or protein is not fully functional), a genome engineering therapy would be beneficial. Such genome engineering therapy may comprise the step of administering to the patient (i) an RNA (in particular an RNA of the present invention) comprising a nucleotide sequence encoding a genomic engineering protein and (ii) a DNA comprising a nucleotide sequence encoding the peptide or protein in its native (i.e., unmutated) form.

Alternatively, a genetic reprogramming therapy would be beneficial, in particular with patients having a disease or disorder which causes a depletion or extinction of cells producing the desired peptide or protein (e.g., a hormone such as insulin). For example, such genetic reprogramming therapy may comprise the steps of (a) introducing an RNA (in particular an RNA of the present invention) comprising a nucleotide sequence encoding one or more reprogramming factors into somatic cells; (b) allowing the development of cells having stem cell characteristics; and (c) administering the cells having stem cell characteristics to a patient. In a preferred embodiment, the somatic cells are autologous to the patient.

The term "translation" according to the invention relates to the process in the ribosomes of a cell by which a strand of mRNA directs the assembly of a sequence of amino acids to make a peptide or protein. The translation may be performed in vivo (e.g., in a cell, tissue, or organism) or in vitro (e.g., using a cell-free system).

Expression control sequences or regulatory sequences, which according to the invention may be linked functionally with a nucleic acid, can be homologous or heterologous with respect to the nucleic acid. A coding sequence and a regulatory sequence are linked together "functionally" if they are bound together covalently, so that the transcription or translation of the coding sequence is under the control or under the influence of the regulatory sequence. If the coding sequence is to be translated into a functional protein, with functional linkage of a regulatory sequence with the coding sequence, induction of the regulatory sequence leads to a transcription of the coding sequence, without causing a reading frame shift in the coding sequence or inability of the coding sequence to be translated into the desired protein or peptide.

The term "expression control sequence" or "regulatory sequence" comprises, according to the invention, promoters, ribosome-binding sequences and other control elements, which control the transcription of a nucleic acid or the translation of the derived RNA. In certain embodiments of the invention, the regulatory sequences can be controlled. The precise structure of regulatory sequences can vary depending on the species or depending on the cell type, but generally comprises 5'-untranscribed and 5'- and 3'-untranslated sequences, which are involved in the initiation of transcription or translation, such as TATA-box, capping-sequence, CAAT-sequence and the like. In particular, 5'-untranscribed regulatory sequences comprise a promoter region that includes a promoter sequence for transcriptional control of the functionally bound gene. Regulatory sequences can also comprise enhancer sequences or upstream activator sequences.

According to the invention it is preferred that a nucleic acid such as RNA (preferably mRNA) encoding a peptide or protein once taken up by or introduced, i.e. transfected or transduced, into a cell which cell may be present in vitro or in a subject results in expression of said peptide or protein. The cell may express the encoded peptide or protein intracellularly (e.g. in the cytoplasm and/or in the nucleus), may secrete the encoded peptide or protein, or may express it on the surface.

According to the invention, terms such as "nucleic acid expressing" and "nucleic acid encoding" or similar terms are used interchangeably herein and with respect to a particular peptide or polypeptide mean that the nucleic acid, if present in the appropriate environment, preferably within a cell, can be expressed to produce said peptide or polypeptide.

According to the invention, RNA is to be transferred into cells either in vitro or in vivo, e.g., by administration of RNA intraperitoneally, intramuscularly, or intradermally or, in case the cells are immature antigen presenting cells, into the lymphatic system (such as into the lymph nodes). According to the present invention, any technique which is suitable to transfer RNA into cells may be used to introduce RNA into cells. Preferably, the RNA is transfected into cells by standard techniques. Such techniques comprise transfection of nucleic acid calcium phosphate precipitates, transfection of nucleic acids which are associated with DEAE, the transfection or infection with viruses which carry the nucleic acids of interest, electroporation, lipofection, and microinjection. According to the present invention, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. In a particularly preferred embodiment, the RNA and/or the compositions of the present invention are administered as naked RNA preferably intraperitoneally, intramuscularly, by intranodal injection or transdermal administration. In case of antigen-presenting cells (such as immature antigen-presenting cells), preferably dendritic cells (such as immature dendritic cells), a conventional transfection technique is not absolutely necessary to introduce naked RNA into said cells, since in particular immature antigen-presenting cells such as immature dendritic cells are capable of taking up naked RNA by macropinocytosis. Preferably, the introduction of RNA which encodes a peptide or protein of interest into a cell results in expression of said peptide or protein of interest in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

The term "peptide" as used herein comprises oligo- and polypeptides and refers to substances comprising two or more, preferably 3 or more, preferably 4 or more, preferably 6 or more, preferably 8 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" preferentially refers to large peptides, preferably to peptides with more than 100 amino acid residues, but in general the terms "peptide" and "protein" are synonyms and are used interchangeably herein.

The term "immunologically active compound" relates to any compound altering an immune response, preferably by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

In one embodiment, RNA (such as mRNA) that codes for an antigen such a disease-associated antigen is administered to a mammal, in particular if treating a mammal having a disease involving or expressing the antigen (disease-associated antigen) is desired. The RNA is preferably taken up into the mammal's antigen-presenting cells (monocytes, macrophages, dendritic cells or other cells). An antigenic translation product of the RNA is formed and the product is displayed on the surface of the cells for recognition by T cells. In one embodiment, the antigen or a product produced by optional procession thereof is displayed on the cell surface in the context of MHC molecules for recognition by T cells through their T cell receptor leading to their activation.

The term "portion of MHC molecules which present an antigen of interest" refers to the fraction of MHC molecules on the surface of an antigen presenting cell which are loaded with, i.e., are bound to, a particular antigen or an antigen peptide derived from said antigen relative to the total amount of MHC molecules on the surface of the cell. In a preferred embodiment, the RNA modified with a 5'-cap compound of the present invention is capable of increasing the portion of MHC molecules which present an antigen of interest on the surface of an antigen presenting cell into which the RNA was transferred.

This is in comparison to an RNA which does not carry the 5'-cap structure of the 5'-cap compound of the present invention, in particular, an RNA which carries a conventional RNA cap.

According to the invention, the terms "disease", "disorder", and "condition" are used herein interchangeably and refer to any pathological state, including infectious diseases (i.e., diseases caused by a pathogen), tumor diseases, and undesirable inflammation.

By "being at risk" is meant an individual, i.e., a patient, that is identified as having a higher than normal chance of developing a disease compared to the general population. In addition, an individual who has had, or who currently has, a disease is a subject who has an increased risk for developing a disease, as such a subject may continue to develop a disease.

The term "in vivo" relates to the situation in a subject.

The term "autologous" is used to describe anything that is derived from the same subject. For example, "autologous cell" refers to a cell derived from the same subject. Such procedures are advantageous because they overcome the immunological barrier which otherwise results in rejection.

The term "heterologous" is used to describe something consisting of multiple different elements. As an example, the transfer of one individual's bone marrow into a different individual constitutes a heterologous transplant. A heterologous gene is a gene derived from a source other than the subject.

The term "non-nucleotidic linker" as used herein means any linker of two nucleosides which is not phosphate or a phosphate derivate (such as phosphorothioate, boranophosphate, imidophosphate, alkylene phosphate, phosphorodithioate, alkylphosphonate, phosphotriester, or phosphoroamidite).

Preferably, a non-nucleotide linker is a peptide, an amine, an aliphatic hydrocarbon (e.g. alkyl), or an aromatic hydrocarbon, wherein the hydrocarbons optionally can include one or more functional groups including, but not limited to, hydroxy, amino, thiol, thioether, ether, amide, thioamide, ester, urea, or thiourea. A particular example of such non-nucleotidic linkers includes, but is not limited to, an alkyl linker. The alkyl linker may be branched or unbranched, cyclic or acyclic, substituted or unsubstituted, saturated or unsaturated, chiral, achiral or racemic mixture. The alkyl linkers can have from 2 to 18 carbon atoms, such as from 3 to 9 carbon atoms. Some alkyl linkers include one or more functional groups including, but not limited to, hydroxy, amino, thiol, thioether, ether, amide, thioamide, ester, urea, and thioether. Such alkyl linkers can include, but are not limited to, 1-propanol, 1,2-propanediol, 1,3-propanediol, 1,2,3-propanetriol, triethylene glycol, hexaethylene glycol, polyethylene glycol linkers (e.g. [—O—$CH_2CH_2$-]$_c$, (c=1, 2, 3, 4, 5, 6, 7, 8, or 9)), methyl linkers, ethyl linkers, propyl linkers, butyl linkers, or hexyl linkers. In some embodiments, the non-nucleotidic linker is glycerol or a glycerol homolog of the formula HO—$(CH_2)_o$—CH(OH)—$(CH_2)_p$—OH, wherein o and p independently are integers from 1 to 6, e.g., from 1 to 4, or from 1 to 3. In some other embodiments, the non-nucleotidic linker is a derivative of 1,3-diamino-2-hydroxypropane, such as those having the formula HO—$(CH_2)_m$—C(O)NH—$CH_2$—CH(OH)—$CH_2$—NHC(O$MCH_2)_m$—OH, wherein each m is independently an integer from 0 to 10, e.g., from 0 to 6, from 2 to 6, or from 2 to 4.

The term "alkyl" refers to a monoradical of a saturated straight or branched hydrocarbon. Preferably, the alkyl group comprises from 1 to 20 carbon atoms, such as from 1 to 12 or from 1 to 10 carbon atoms, i.e., 1, 2, 3, 4, 5, 6, 7, 8, 9, or 10 carbon atoms, more preferably 1 to 8 carbon atoms, such as 1 to 6 or 1 to 4 carbon atoms. Exemplary alkyl groups include methyl, ethyl, propyl, iso-propyl, butyl (e.g., n-butyl, iso-butyl, tert-butyl), pentyl (e.g., n-pentyl, iso-pentyl, sec-pentyl, neo-pentyl), 1,2-dimethyl-propyl, iso-amyl, n-hexyl, iso-hexyl, sec-hexyl, 2,2-dimethylbutyl, n-heptyl, iso-heptyl, n-octyl, 2-ethyl-hexyl, n-nonyl, n-decyl, and the like. A "substituted alkyl" means that one or more (such as 1 to the maximum number of hydrogen atoms bound to an alkyl group, e.g., 1, 2, 3, 4, 5, 6, 7, 8, 9, or up to 10, such as between 1 to 5, 1 to 4, or 1 to 3, or 1 or 2) hydrogen atoms of the alkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. Examples of a substituted alkyl include trifluoromethyl, 2,2,2-trichloroethyl, arylalkyl (also called "aralkyl", e.g., benzyl, chloro(phenyl)methyl, 4-methylphenylmethyl, (2,4-dimethylphenyl)methyl, o-fluorophenylmethyl, 2-phenylpropyl, 2-, 3-, or 4-carboxyphenylalkyl), or heteroarylalkyl (also called "heteroaralkyl").

The term "alkenyl" refers to a monoradical of an unsaturated straight or branched hydrocarbon having at least one carbon-carbon double bond. Generally, the maximum number of carbon-carbon double bonds in the alkenyl group can be equal to the integer which is calculated by dividing the number of carbon atoms in the alkenyl group by 2 and, if the number of carbon atoms in the alkenyl group is uneven, rounding the result of the division down to the next integer. For example, for an alkenyl group having 9 carbon atoms, the maximum number of carbon-carbon double bonds is 4. Preferably, the alkenyl group has 1 to 4, i.e., 1, 2, 3, or 4, carbon-carbon double bonds. Preferably, the alkenyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkenyl group comprises from 2 to 10 carbon atoms and 1, 2, 3, 4, or 5 carbon-carbon double bonds, more preferably it comprises 2 to 8 carbon atoms and 1, 2, 3, or 4 carbon-carbon double bonds, such as 2 to 6 carbon atoms and 1, 2, or 3 carbon-carbon double bonds or 2 to 4 carbon atoms and 1 or 2 carbon-carbon double bonds. The carbon-carbon double bond(s) may be in cis (Z) or trans (E) configuration. Exemplary alkenyl groups include ethenyl (i.e., vinyl), 1-propenyl, 2-propenyl (i.e., allyl), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2'-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl, and the like. If an alkenyl group is attached to a nitrogen atom, the double bond cannot be alpha to the nitrogen atom. A "substituted alkenyl" means that one or more (such as 1 to the maximum number of hydrogen atoms bound to an alkenyl group, e.g., 1, 2, 3, 4, 5, 6, 7, 8, 9, or up to 10, such as between 1 to 5, 1 to 4, or 1 to 3, or 1 or 2) hydrogen atoms of the alkenyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl. An example of a substituted alkenyl is styryl (i.e., 2-phenylvinyl).

The term "alkynyl" refers to a monoradical of an unsaturated straight or branched hydrocarbon having at least one carbon-carbon triple bond. Generally, the maximum number of carbon-carbon triple bonds in the alkynyl group can be equal to the integer which is calculated by dividing the number of carbon atoms in the alkynyl group by 2 and, if the number of carbon atoms in the alkynyl group is uneven, rounding the result of the division down to the next integer. For example, for an alkynyl group having 9 carbon atoms, the maximum number of carbon-carbon triple bonds is 4. Preferably, the alkynyl group has 1 to 4, i.e., 1, 2, 3, or 4, more preferably 1 or 2 carbon-carbon triple bonds. Preferably, the alkynyl group comprises from 2 to 20 carbon atoms, such as from 2 to 12 or from 2 to 10 carbon atoms, i.e., 2, 3, 4, 5, 6, 7, 8, 9, or 10 carbon atoms, more preferably 2 to 8 carbon atoms, such as 2 to 6 carbon atoms or 2 to 4 carbon atoms. Thus, in a preferred embodiment, the alkynyl group comprises from 2 to 10 carbon atoms and 1, 2, 3, 4, or 5 (preferably 1, 2, or 3) carbon-carbon triple bonds, more preferably it comprises 2 to 8 carbon atoms and 1, 2, 3, or 4 (preferably 1 or 2) carbon-carbon triple bonds, such as 2 to 6 carbon atoms and 1, 2 or 3 carbon-carbon triple bonds or 2 to 4 carbon atoms and 1 or 2 carbon-carbon triple bonds. Exemplary alkynyl groups include ethynyl, 1-propynyl (i.e., —C≡CCH₃), 2-propynyl (i.e., —CH₂C≡CH or propargyl), 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, 1-heptynyl, 2-heptynyl, 3-heptynyl, 4-heptynyl, 5-heptynyl, 6-heptynyl, 1-octynyl, 2'-octynyl, 3-octynyl, 4-octynyl, 5-octynyl, 6-octynyl, 7-octynyl, 1-nonylyl, 2-nonynyl, 3-nonynyl, 4-nonynyl, 5-nonynyl, 6-nonynyl, 7-nonynyl, 8-nonynyl, 1-decynyl, 2-decynyl, 3-decynyl, 4-decynyl, 5-decynyl, 6-decynyl, 7-decynyl, 8-decynyl, 9-decynyl, and the like. If an alkynyl group is attached to a nitrogen atom, the triple bond cannot be alpha to the nitrogen atom. A "substituted alkynyl" means that one or more (such as 1 to the maximum number of hydrogen atoms bound to an alkynyl group, e.g., 1, 2, 3, 4, 5, 6, 7, 8, 9, or up to 10, such as between 1 to 5, 1 to 4, or 1 to 3, or 1 or 2) hydrogen atoms of the alkynyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen or optionally substituted aryl.

The term "aryl" or "aromatic ring" refers to a monoradical of an aromatic cyclic hydrocarbon. Preferably, the aryl group contains 3 to 14 (e.g., 5 to 10, such as 5, 6, or 10) carbon atoms which can be arranged in one ring (e.g., phenyl) or two or more condensed rings (e.g., naphthyl). Exemplary aryl groups include cyclopropenylium, cyclopentadienyl, phenyl, indenyl, naphthyl, azulenyl, fluorenyl, anthryl, and phenanthryl. Preferably, "aryl" refers to a monocyclic ring containing 6 carbon atoms or an aromatic bicyclic ring system containing 10 carbon atoms. Preferred examples are phenyl and naphthyl. A "substituted aryl" means that one or more (such as 1 to the maximum number of hydrogen atoms bound to an aryl group, e.g., 1, 2, 3, 4, 5, 6, 7, 8, 9, or up to 10, such as between 1 to 5, 1 to 4, or 1 to 3, or 1 or 2) hydrogen atoms of the aryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR¹¹ (e.g., —OH), —SR¹¹ (e.g., —SH), —N(R¹²)(R¹³) (e.g., —NH₂), =Z (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted aryl include biphenyl, 2-fluorophenyl, anilinyl, 3-nitrophenyl, 4-hydroxyphenyl, methoxyphenyl (i.e., 2-, 3-, or 4-methoxyphenyl), and 4-ethoxyphenyl.

The term "heteroaryl" or "heteroaromatic ring" means an aryl group as defined above in which one or more carbon atoms in the aryl group are replaced by heteroatoms of O, S, or N. Preferably, heteroaryl refers to a five or six-membered aromatic monocyclic ring wherein 1, 2, or 3 carbon atoms are replaced by the same or different heteroatoms of O, N, or S. Alternatively, it means an aromatic bicyclic or tricyclic ring system wherein 1, 2, 3, 4, or 5 carbon atoms are replaced with the same or different heteroatoms of O, N, or S. Preferably, in each ring of the heteroaryl group the maximum number of O atoms is 1, the maximum number of S atoms is 1, and the maximum total number of O and S atoms is 2. Exemplary heteroaryl groups include furanyl, thienyl, oxazolyl, isoxazolyl, oxadiazolyl, pyrrolyl, imidazolyl, pyrazolyl, triazolyl, tetrazolyl, thiazolyl, isothiazolyl, thiadiazolyl, pyridyl, pyrimidinyl, pyrazinyl, triazinyl, benzofuranyl, indolyl, isoindolyl, benzothienyl, 1H-indazolyl, benzimidazolyl, benzoxazolyl, indoxazinyl, benzisoxazolyl, benzothiazolyl, benzisothiazolyl, benzotriazolyl, quinolinyl, isoquinolinyl, benzodiazinyl, quinoxalinyl, quinazolinyl, benzotriazinyl, pyridazinyl, phenoxazinyl, thiazolopyridinyl, pyrrolothiazolyl, phenothiazinyl, isobenzofuranyl, chromenyl, xanthenyl, pyrrolizinyl, indolizinyl, indazolyl, purinyl, quinolizinyl, phthalazinyl, naphthyridinyl, cinnolinyl, pteridinyl, carbazolyl, phenanthridinyl, acridinyl, perimidinyl, phenanthrolinyl, and phenazinyl. Exemplary 5- or 6-memered heteroaryl groups include furanyl, thienyl, oxazolyl, isoxazolyl, oxadiazolyl, pyrrolyl, imidazolyl (e.g., 2-imidazolyl), pyrazolyl, triazolyl, tetrazolyl, thiazolyl, isothiazolyl, thiadiazolyl, pyridyl (e.g., 4-pyridyl), pyrimidinyl, pyrazinyl, triazinyl, and pyridazinyl. A "substituted heteroaryl" means that one or more (such as 1 to the maximum number of hydrogen atoms bound to a heteroaryl group, e.g., 1, 2, 3, 4, 5, 6, 7, 8, 9, or up to 10, such as between 1 to 5, 1 to 4, or 1 to 3, or 1 or 2) hydrogen atoms of the heteroaryl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —OR¹¹ (e.g., —OH), —SR¹¹ (e.g., —SH), —N(R¹²)(R¹³) (e.g., —NH₂), =Z (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted heteroaryl include 3-phenylpyrrolyl, 2,3'-bifuryl, 4-methylpyridyl, 2-, or 3-ethylindolyl.

The term "cycloalkyl" or "cycloaliphatic" represents cyclic non-aromatic versions of "alkyl" and "alkenyl" with preferably 3 to 14 carbon atoms, such as 3 to 10 carbon atoms, i.e., 3, 4, 5, 6, 7, 8, 9, or 10 carbon atoms, more preferably 3 to 7 carbon atoms. In one embodiment, the cycloalkyl group has 1, 2, or more (preferably 1 or 2) double bonds. Exemplary cycloalkyl groups include cyclopropyl, cyclopropenyl, cyclobutyl, cyclobutenyl, cyclopentyl, cyclopentenyl, cyclohexyl, cyclohexenyl, cycloheptyl, cycloheptenyl, cyclooctyl, cyclooctenyl, cyclononyl, cyclononenyl, cylcodecyl, cylcodecenyl, and adamantyl. The term "cycloalkyl" is also meant to include bicyclic and tricyclic versions thereof. If bicyclic rings are formed it is preferred that the respective rings are connected to each other at two adjacent carbon atoms, however, alternatively the two rings are connected via the same carbon atom, i.e., they form a spiro ring system or they form "bridged" ring systems. Preferred examples of cycloalkyl include $C_3$-$C_8$-cycloalkyl, in particular cyclopropyl, cyclobutyl, cyclopentyl, cyclopentenyl, cyclohexyl, cyclohexenyl, cyclohexadienyl, cycloheptyl, cyclooctyl, spiro[3,3]heptyl, spiro[3,4]octyl, spiro[4,3]octyl, spiro[4,5]decanyl, bicyclo[4.1.0]heptyl, bicyclo[3.2.0]heptyl, bicyclo[2.2.1]heptyl (i.e., norbornyl), bicyclo[2.2.2]octyl, bicyclo[5.1.0]octyl, bicyclo[4.2.0]octyl, bicyclo[4.3.0]nonyl, 1,2,3,4-tetrahydronaphthyl (i.e., tetralinyl), and bicyclo[4.4.0]decanyl (i.e., decalinyl). A "substituted cycloalkyl" means that one or more (such as 1 to the maximum number of hydrogen atoms bound to a cycloalkyl group, e.g., 1, 2, 3, 4, 5, 6, 7, 8, 9, or up to 10, such as between 1 to 5, 1 to 4, or 1 to 3, or 1 or 2) hydrogen atoms of the cycloalkyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —OR¹¹ (e.g., —OH), —SR¹¹ (e.g., —SH), —N(R¹²)(R¹³) (e.g., —NH₂), =Z (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl). Examples of a substituted cycloalkyl include oxocyclohexyl, oxocyclopentyl, fluorocyclohexyl, and oxocyclohexenyl.

The term "heterocyclyl" or "heterocyclic ring" means a cycloalkyl group as defined above in which from 1, 2, 3, or 4 carbon atoms in the cycloalkyl group are replaced by heteroatoms of oxygen, nitrogen, silicon, selenium, phosphorous, or sulfur, preferably O, S, or N. A heterocyclyl group has preferably 1 or 2 rings containing from 3 to 10, such as 3, 4, 5, 6, or 7, ring atoms. Preferably, in each ring of the heterocyclyl group the maximum number of O atoms is 1, the maximum number of S atoms is 1, and the maximum total number of O and S atoms is 2. The term "heterocyclyl" is also meant to encompass partially or completely hydrogenated forms (such as dihydro, tetrahydro or perhydro forms) of the above-mentioned heteroaryl groups. Exemplary heterocyclyl groups include morpholinyl, pyrrolidinyl, imidazolidinyl, pyrazolidinyl, piperidinyl (also called piperidyl), piperazinyl, di- and tetrahydrofuranyl, di- and tetrahydrothienyl, di- and tetrahydropyranyl, urotropinyl, lactones, lactams, cyclic imides, and cyclic anhydrides. A "substituted heterocyclyl" means that one or more (such as 1 to the maximum number of hydrogen atoms bound to a heterocyclyl group, e.g., 1, 2, 3, 4, 5, 6, 7, 8, 9, or up to 10, such as between 1 to 5, 1 to 4, or 1 to 3, or 1 or 2) hydrogen atoms of the heterocyclyl group are replaced with a substituent other than hydrogen (when more than one hydrogen atom is replaced the substituents may be the same or different). Preferably, the substituent other than hydrogen is a $1^{st}$ level substituent, a $2^{nd}$ level substituent, or a $3^{rd}$ level substituent as specified herein, such as halogen, —CN, nitro, —$OR^{11}$ (e.g., —OH), —$SR^{11}$ (e.g., —SH), —$N(R^{12})(R^{13})$ (e.g., —$NH_2$), =Z (e.g., =O, =S, or =NH), alkyl (e.g., $C_{1-6}$ alkyl), alkenyl (e.g., $C_{2-6}$ alkenyl), and alkynyl (e.g., $C_{2-6}$ alkynyl).

The term "aromatic" as used in the context of hydrocarbons means that the whole molecule has to be aromatic. For example, if a monocyclic aryl is hydrogenated (either partially or completely) the resulting hydrogenated cyclic structure is classified as cycloalkyl for the purposes of the present invention. Likewise, if a bi- or polycyclic aryl (such as naphthyl) is hydrogenated the resulting hydrogenated bi- or polycyclic structure (such as 1,2-dihydronaphthyl) is classified as cycloalkyl for the purposes of the present invention (even if one ring, such as in 1,2-dihydronaphthyl, is still aromatic). A similar distinction is made within the present application between heteroaryl and heterocyclyl. For example, indolinyl, i.e., a dihydro variant of indolyl, is classified as heterocyclyl for the purposes of the present invention, since only one ring of the bicyclic structure is aromatic and one of the ring atoms is a heteroatom.

The term "halogen" or "halo" means fluoro, chloro, bromo, or iodo, preferably fluoro. The term "hydroxy" means OH. The term "alkoxy" means O-alkyl, wherein alkyl is as defined above, and includes methoxy, ethoxy, propoxy, butoxy, iso-butoxy, sec-butoxy, pentoxy, hexyloxy, heptyloxy, octyloxy, nonyloxy, and decyloxy. The term "substituted alkoxy" means O-(substituted alkyl), wherein substituted alkyl is as defined above, and includes 2-methoxyethoxy. The term "nitro" means $NO_2$. The term "cyano" means the group —CN. The term "isocyano" means the group —NC. The term "cyanato" means the group —OCN. The term "isocyanato" means the group —NCO. The term "thiocyanato" means the group —SCN. The term "isothiocyanato" means the group —NCS. The term "azido" means $N_3$.

The term "amino" includes unsubstituted amino (i.e., the group —$NH_2$) and substituted amino (i.e., mono- or disubstituted amino, wherein one or two of the hydrogen atoms have been replaced with a group other than hydrogen). Thus, the term "amino" means the group —$N(R^{12})(R^{13})$, wherein $R^{12}$ and $R^{13}$ are, in each case, independently selected from the group consisting of —H, alkyl, alkenyl, alkynyl, cycloalkyl, aryl, heteroaryl, and heterocyclyl, or $R^{12}$ and $R^{13}$ may join together with the nitrogen atom to which they are attached to form the group —N=$CR^{15}R^{16}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; $R^{15}$ and $R^{16}$ are independently selected from the group consisting of —H, alkyl, alkenyl, alkynyl, cycloalkyl, aryl, heteroaryl, heterocyclyl, and —$NH_yR^{20}_{2-y}$, or $R^{15}$ and $R^{16}$ may join together with the atom to which they are attached to form a ring which is optionally substituted with one or more (such as 1 to the maximum number of hydrogen atoms bound to the ring, e.g., 1, 2, 3, 4, 5, 6, 7, 8, 9, or up to 10, such as between 1 to 5, 1 to 4, or 1 to 3, or 1 or 2) independently selected $R^{30}$, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; y is an integer from 0 to 2; $R^{20}$ is selected from the group consisting of alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ (or $2^{nd}$ or $3^{rd}$) level substituent.

The term "imino" means the group —$N(R^{14})$—, wherein both free valences of the nitrogen atom may bind to one other atom (e.g., C) resulting in a double bond (e.g., C=N($R^{14}$)) or to different atoms (e.g., two C atoms) resulting two single bonds (e.g., C—$N(R^{14})$—C). In each case, $R^{14}$ is selected from the group consisting of —H, alkyl, alkenyl, alkynyl, cycloalkyl, aryl, heteroaryl, and heterocyclyl, wherein each of the alkyl, alkenyl, alkynyl, cycloalkyl, aryl, heteroaryl, and heterocyclyl groups is optionally substituted with one or more (such as 1 to the maximum number of hydrogen atoms bound to the alkyl, alkenyl, alkynyl, cycloalkyl, aryl, heteroaryl, or heterocyclyl group, e.g., 1, 2, 3, 4, 5, 6, 7, 8, 9, or up to 10, such as between 1 to 5, 1 to 4, or 1 to 3, or 1 or 2) independently selected $R^{30}$; and $R^{30}$ is a $1^{st}$ (or $2^{nd}$ or $3^{rd}$) level substituent.

The term "optionally substituted" indicates that one or more (such as 1 to the maximum number of hydrogen atoms bound to a moiety, e.g., 1, 2, 3, 4, 5, 6, 7, 8, 9, or up to 10, such as between 1 to 5, 1 to 4, or 1 to 3, or 1 or 2) hydrogen atom(s) may be replaced with a group/substituent (i.e., a $1^{st}$ level substituent) different from hydrogen such as alkyl (preferably, $C_{1-6}$ alkyl), alkenyl (preferably, $C_{2-6}$ alkenyl), alkynyl (preferably, $C_{2-6}$ alkynyl), aryl (preferably, 3- to 14-membered aryl), heteroaryl (preferably, 3- to 14-membered heteroaryl), cycloalkyl (preferably, 3- to 14-membered cycloalkyl), heterocyclyl (preferably, 3- to 14-membered heterocyclyl), halogen, —CN, —NC, —NCO, —CNO, —SCN, —NCS, —N$_3$, —NO$_2$, —OR$^{71}$, —N(R$^{72}$)(R$^{73}$), —ON(R$^{72}$)(R$^{73}$), —N$^+$(—O$^-$)(R$^{72}$)(R$^{73}$), —S(O)$_{0-2}$R$^{71}$ (i.e., —SR$^{71}$, —S(O)R$^{71}$, or —S(O)$_2$R$^{71}$), —S(O)$_{0-2}$OR$^7$ (e.g., —S(O)$_{1-2}$OR$^{71}$), —OS(O)$_{0-2}$OR$^{71}$ (e.g., —OS(O)$_{1-2}$OR$^{71}$), —S(O)$_{0-2}$N(R$^{72}$)(R$^{73}$) (e.g., —S(O)$_{1-2}$N(R$^{72}$)(R$^{73}$)), —OS(O)$_{0-2}$N(R$^{72}$)(R$^{73}$) (e.g., —OS(O)$_{1-2}$N(R$^{72}$)(R$^{73}$)), —N(R$^{71}$)S(O)$_{0-2}$R$^{71}$ (e.g., —N(R$^{71}$)S(O)$_{1-2}$R$^{71}$), —NR$^{71}$S(O)$_{0-2}$OR$^{71}$ (e.g., —NR$^{71}$S(O)$_{1-2}$OR$^{71}$), —NR$^{71}$S(O)$_{0-2}$N(R$^{72}$)(R$^{73}$) (e.g., —NR$^{71}$S(O)$_{1-2}$N(R$^{72}$)(R$^{73}$)), —C(=Z$^1$)R$^{71}$, —C(=Z$^1$)Z$^1$R$^{71}$, —Z$^1$C(=Z$^1$)R$^7$, and —Z$^1$C(=Z$^1$)Z$^1$R$^{71}$, and/or any two 1$^{st}$ level substituents which are bound to the same carbon atom of a cycloalkyl or heterocyclyl group may join together to form =Z$^1$, wherein each of the alkyl, alkenyl, alkynyl, aryl, heteroaryl, cycloalkyl, and heterocyclyl groups of the 1$^{st}$ level substituent may themselves be substituted by one or more (e.g., one, two or three) substituents (i.e., 2$^{nd}$ level substituents) selected from the group consisting of C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl, halogen, —CF$_3$, —CN, —NC, —NCO, —CNO, —SCN, —NCS, —N$_3$, —NO$_2$, —OR$^{81}$, —N(R$^{82}$)(R$^{83}$), —ON(R$^{82}$)(R$^{83}$), —N$^+$(—O$^-$)(R$^{82}$)(R$^{83}$), —S(O)$_{0-2}$R$^{81}$ (i.e., —SR$^{81}$, —S(O)R$^{81}$, or —S(O)$_2$R$^{81}$), —S(O)$_{0-2}$OR$^{81}$ (e.g., —S(O)$_{1-2}$OR$^{81}$), —OS(O)$_{0-2}$R$^{81}$ (e.g., —OS(O)$_{1-2}$R$^{81}$), —OS(O)$_{0-2}$OR$^{81}$ (e.g., —OS(O)$_{1-2}$OR$^{81}$), —S(O)$_{0-2}$N(R$^{82}$)(R$^{83}$) (e.g., —S(O)$_{1-2}$N(R$^{82}$)(R$^{83}$)), —OS(O)$_{0-2}$N(R$^{82}$)(R$^{83}$) (e.g., —OS(O)$_{1-2}$N(R$^{82}$)(R$^{83}$)), —N(R$^{81}$)S(O)$_{0-2}$R$^{81}$ (e.g., —N(R$^{81}$)S(O)$_{1-2}$R$^{81}$), —NR$^{81}$S(O)$_{0-2}$OR$^{81}$ (e.g., —NR$^{81}$S(O)$_{1-2}$OR$^{81}$), —NR$^{81}$S(O)$_{0-2}$N(R$^{82}$)(R$^{83}$) (e.g., —NR$^{81}$S(O)$_{1-2}$N(R$^{82}$)(R$^{83}$)), —C(=Z$^2$)R$^{81}$, —C(=Z$^2$)Z$^2$R$^{81}$, —Z$^2$C(=Z$^2$)R$^{81}$, and —Z$^2$C(=Z$^2$)Z$^2$R$^{81}$, and/or any two 2$^{nd}$ level substituents which are bound to the same carbon atom of a cycloalkyl or heterocyclyl group may join together to form =Z$^2$, wherein each of the C$_{1-6}$ alkyl, C$_{2-6}$ alkenyl, C$_{2-6}$ alkynyl, 3- to 14-membered aryl, 3- to 14-membered heteroaryl, 3- to 14-membered cycloalkyl, 3- to 14-membered heterocyclyl groups of the 2$^{nd}$ level substituent is optionally substituted with one or more (e.g., one, two or three) substituents (i.e., 3$^{rd}$ level substituents) independently selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —OC(=O)(C$_{1-3}$ alkyl), —OC(=O)O(C$_{1-3}$ alkyl), —OC(=O)NH$_{2-z}$(C$_{1-3}$ alkyl)$_z$, —NHC(=O)(C$_{1-3}$ alkyl), —NHC(=O)NH$_{z-2}$(C$_{1-3}$ alkyl)$_z$, —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, and/or any two 3' level substituents which are bound to the same carbon atom of a cycloalkyl or heterocyclyl group may join together to form =O, =S, =NH, or =N(C$_{1-3}$ alkyl);

wherein

R$^{71}$, R$^{72}$, and R$^{73}$ are independently selected from the group consisting of —H, C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl, wherein each of the C$_{1-6}$ alkyl, C$_{2-6}$ alkenyl, C$_{2-6}$ alkynyl, 3- to 7-membered cycloalkyl, 5- or 6-membered aryl, 5- or 6-membered heteroaryl, and 3- to 7-membered heterocyclyl groups is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$ (C$_{1-3}$ alkyl)$_z$, —OC(=O)(C$_{1-3}$ alkyl), —OC(=O)O(C$_{1-3}$ alkyl), —OC(=O)NH$_{2-z}$(C$_{1-3}$ alkyl)$_z$, —NHC(=O)(C$_{1-3}$ alkyl), —NHC(=O)NH$_{z-2}$(C$_{1-3}$ alkyl)$_z$, —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl;

or R$^{72}$ and R$^{73}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —OC(=O)(C$_{1-3}$ alkyl), —OC(=O)O(C$_{1-3}$ alkyl), —OC(=O)NH$_{2-z}$(C$_{1-3}$ alkyl)$_z$, —NHC(=O)(C$_{1-3}$ alkyl), —NHC(=O)NH$_{z-2}$(C$_{1-3}$ alkyl)$_z$, —NHC(=NH)NH$_{z-2}$(C$_{1-3}$ alkyl)$_z$, and —N(C$_{1-3}$ alkyl)C(=NH)NH$_{z-2}$(C$_{1-3}$ alkyl)$_z$, wherein z is 0, 1, or 2 and C$_{1-3}$ alkyl is methyl, ethyl, propyl or isopropyl;

R$^{81}$, R$^{82}$, and R$^{83}$ are independently selected from the group consisting of —H, C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl, wherein each of the C$_{1-4}$ alkyl, C$_{2-4}$ alkenyl, C$_{2-4}$ alkynyl, 3- to 6-membered cycloalkyl, 5- or 6-membered aryl, 5- or 6-membered heteroaryl, and 3- to 6-membered heterocyclyl groups is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_2$—Z(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$ (C$_{1-3}$ alkyl)$_z$, —OC(=O)(C$_{1-3}$ alkyl), —OC(=O)O(C$_{1-3}$ alkyl), —OC(=O)NH$_{2-z}$(C$_{1-3}$ alkyl)$_z$, —NHC(=O)(C$_{1-3}$ alkyl), —NHC(=O)NH$_{z-2}$(C$_{1-3}$ alkyl)$_z$, —NHC(=NH)NH$_{z-2}$(C$_{1-3}$ alkyl)$_z$, and —N(C$_{1-3}$ alkyl)C(=NH)NH$_{2-z}$(C$_{1-3}$ alkyl)$_z$, wherein z is 0, 1, or 2 and C$_{1-3}$ alkyl is methyl, ethyl, propyl or isopropyl, or R$^{82}$ and R$^{83}$ may join together with the nitrogen atom to which they are attached to form a 5- or 6-membered ring, which is optionally substituted with one, two or three substituents selected from the group consisting of C$_{1-3}$ alkyl, halogen, —CF$_3$, —CN, —NC, —NCO, —CNO, —SCN, —NCS, —N$_3$, —NO$_2$, —OH, —O(C$_{1-3}$ alkyl), —OCF$_3$, —S(C$_{1-3}$ alkyl), —NH$_2$, —NH(C$_{1-3}$ alkyl), —N(C$_{1-3}$ alkyl)$_2$, —NHS(O)$_2$(C$_{1-3}$ alkyl), —S(O)$_2$NH$_{2-z}$(C$_{1-3}$ alkyl)$_z$, —C(=O)(C$_{1-3}$ alkyl), —C(=O)OH, —C(=O)O(C$_{1-3}$ alkyl), —C(=O)NH$_{2-z}$(C$_{1-3}$ alkyl)$_z$, —OC(=O)(C$_{1-3}$ alkyl), —OC(=O)O(C$_{1-3}$ alkyl), —OC(=O)NH$_{2-z}$(C$_{1-3}$ alkyl)$_z$, —NHC(=O)(C$_{1-3}$ alkyl), —NHC(=O)NH$_{z-2}$(C$_{1-3}$ alkyl)$_z$, —NHC(=NH)NH$_{z-2}$(C$_{1-3}$ alkyl)$_z$, and —N($C_{1-3}$ alkyl)C(=NH)NH$_{2-z}$($C_{1-3}$alkyl)$_z$, wherein z is 0, 1, or 2 and $C_{1-3}$ alkyl is methyl, ethyl, propyl or isopropyl;

$Z^1$ and $Z^2$ are independently selected from O, S, and N($R^{84}$), wherein $R^{84}$ is —H or $C_{1-3}$ alkyl.

Typical 1$^{st}$ level substituents are preferably selected from the group consisting of $C_{1-6}$ alkyl, $C_{2-6}$ alkenyl, $C_{2-6}$ alkynyl, 3- to 14-membered (such as 5- or 6-membered) aryl, 3- to 14-membered (such as 5- or 6-membered) heteroaryl, 3- to 14-membered (such as 3- to 7-membered) cycloalkyl, 3- to 14-membered (such as 3- to 7-membered) heterocyclyl, halogen, —CN, —NC, —NCO, —CNO, —SCN, —NCS, —N$_3$, —NO$_2$, —O$R^{71}$, —N($R^{72}$)($R^{73}$), —S(O)$_{0-2}R^{71}$, —S(O)$_{0-2}OR^{71}$, —OS(O)$_{0-2}R^{71}$, —OS(O)$_{0-2}OR^{71}$, —S(O)$_{0-2}$N($R^{72}$)($R^{73}$), —OS(O)$_{0-2}$N($R^{72}$)($R^{73}$), —N($R^{71}$)S(O)$_{0-2}R^{71}$, —N$R^{71}$S(O)$_{0-2}OR^{71}$, —C(=$Z^1$)$R^{71}$, —C(=$Z^1$)$Z^1R^{71}$, —$Z^1$C(=$Z^1$)$R^{71}$, and —$Z^1$C(=$Z^1$)$Z^1R^{71}$, such as $C_{1-4}$ alkyl, $C_{2-4}$ alkenyl, $C_{2-4}$ alkynyl, 5- or 6-membered aryl, 5- or 6-membered heteroaryl, 3- to 7-membered cycloalkyl, 3- to 7-membered heterocyclyl, halogen, —CF$_3$, —CN, —NC, —NCO, —CNO, —SCN, —NCS, —N$_3$, —NO$_2$, —OH, —O($C_{1-3}$ alkyl), —S($C_{1-3}$alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; $Z^1$ is independently selected from O, S, NH and N(CH$_3$); and $R^{71}$, $R^{72}$, and $R^{73}$ are as defined above or, preferably, are independently selected from the group consisting of —H, $C_{1-4}$ alkyl, $C_{2-4}$ alkenyl, $C_{2-4}$ alkynyl, 5- or 6-membered cycloalkyl, 5- or 6-membered aryl, 5- or 6-membered heteroaryl, and 5- or 6-membered heterocyclyl, wherein each of the alkyl, alkenyl, alkynyl, cycloalkyl, aryl, heteroaryl, and heterocyclyl groups is optionally substituted with one, two or three substituents selected from the group consisting of $C_{1-3}$ alkyl, halogen, —CF$_3$, —CN, —NC, —NCO, —CNO, —SCN, —NCS, —N$_3$, —NO$_2$, —OH, —O($C_{1-3}$ alkyl), —OCF$_3$, —S($C_{1-3}$alkyl), —NH$_2$, —NH($C_{1-3}$ alkyl), —N($C_{1-3}$ alkyl)$_2$, —NHS(O)$_2$($C_{1-3}$ alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$($C_{1-3}$ alkyl)$_z$, —NHC(=O)($C_{1-3}$ alkyl), —NHC(=NH)NH$_{z-2}$ ($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl; or $R^{72}$ and $R^{73}$ may join together with the nitrogen atom to which they are attached to form a 5- or 6-membered ring, which is optionally substituted with one, two or three substituents selected from the group consisting of $C_{1-3}$ alkyl, halogen, —CF$_3$, —CN, —NC, —NCO, —CNO, —SCN, —NCS, —N$_3$, —NO$_2$, —OH, —O($C_{1-3}$ alkyl), —OCF$_3$, —S($C_{1-3}$ alkyl)$_z$, —C(=O)OH, —C(=O)O($C_{1-3}$ alkyl), —NHC(=O) ($C_{1-3}$ alkyl), —C(=O)NH$_{2-z}$($C_{1-3}$ alkyl)$_z$, —NHC(=O) ($C_{1-3}$ alkyl), —NHC(=NH)NH$_{z-2}$($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl.

Typical 2$^{nd}$ level substituents are preferably selected from the group consisting of $C_{1-4}$ alkyl, $C_{2-4}$ alkenyl, $C_{2-4}$ alkynyl, 5- or 6-membered aryl, 5- or 6-membered heteroaryl, 5- or 6-membered cycloalkyl, 5- or 6-membered heterocyclyl, halogen, —CF$_3$, —CN, —NC, —NCO, —CNO, —SCN, —NCS, —N$_3$, —NO$_2$, —OH, —O($C_{1-3}$ alkyl), —OCF$_3$, —S($C_{1-3}$ alkyl), —NH$_2$, —NH($C_{1-3}$ alkyl), —N($C_{1-3}$ alkyl)$_2$, —NHS(O)$_2$($C_{1-3}$alkyl), —S(O)$_2$NH$_{2-z}$($C_{1-3}$ alkyl)$_z$, —C(=O)OH, —C(=O)O($C_{1-3}$ alkyl), —C(=O)NH$_{2-z}$ ($C_{1-3}$ alkyl)$_z$, —NHC(=O)($C_{1-3}$ alkyl), —NHC(=NH)NH$_{z-2}$ ($C_{1-3}$ alkyl)$_z$, and —N($C_{1-3}$ alkyl)C(=NH)NH$_{2-z}$($C_{1-3}$ alkyl)$_z$, wherein z is 0, 1, or 2 and $C_{1-3}$ alkyl is methyl, ethyl, propyl or isopropyl. Particularly preferred 2$^{nd}$ level substituents include 4-morpholinyl, homomorpholinyl, 4-piperidinyl, homopiperidinyl (i.e., azepanyl, in particular 4-azepanyl), 4-piperazinyl, homopiperazinyl (i.e., diazepanyl, in particular 2,4-diazepanyl), N-methyl-piperazin-4-yl, N-methyl-homopiperazinyl, —CH$_2$CH$_2$OCH$_3$, —OCH$_2$CH$_2$OCH$_3$, —CH$_2$CH$_2$NH$_{2-z}$(CH$_3$)$_z$, —OCH$_2$CH$_2$NH$_{2-z}$(CH$_3$)$_z$, —CF$_3$, and —OCF$_3$.

Typical 3$^{rd}$ level substituents are preferably selected from the group consisting of phenyl, furanyl, pyrrolyl, thienyl, imidazolyl, oxazolyl, isoxazolyl, thiazolyl, pyridyl, pyrazinyl, pyrimidinyl, pyridazinyl, partially and completely hydrogenated forms of the forgoing groups, morpholino, $C_{1-3}$ alkyl, halogen, —NC, —NCO, —CNO, —SCN, —NCS, —N$_3$, —CF$_3$, —OH, —OCH$_3$, —OCF$_3$, —SCH$_3$, —NH$_{2-z}$(CH$_3$)$_z$, —C(=O)OH, and —C(=O)OCH$_3$, wherein z is 0, 1, or 2.

The term "optional" or "optionally" as used herein means that the subsequently described event, circumstance or condition may or may not occur, and that the description includes instances where said event, circumstance, or condition occurs and instances in which it does not occur.

"Isomers" are compounds having the same molecular formula but differ in structure ("structural isomers") or in the geometrical positioning of the functional groups and/or atoms ("stereoisomers"). "Enantiomers" are a pair of stereoisomers which are non-superimposable mirror-images of each other. A "racemic mixture" or "racemate" contains a pair of enantiomers in equal amounts and is denoted by the prefix (±). "Diastereomers" are stereoisomers which are not enantiomers. "Tautomers" are structural isomers of the same chemical substance that spontaneously interconvert with each other, even when pure.

The 5'-cap compound of the present invention or an RNA modified with a 5'-cap compound of the present invention may be isotopically labeled, i.e., one or more atoms are replaced by a corresponding atom having the same number of protons but differing in the number of neutrons. For example, a hydrogen atom may be replaced by a deuterium atom. Exemplary isotopes which can be used in the 5'-cap compound of the present invention or an RNA modified with a 5'-cap compound of the present invention include deuterium, $^{11}$C, $^{13}$C, $^{14}$C, $^{15}$N, $^{18}$F, $^{32}$S, $^{36}$Cl, and $^{121}$I. The term "isotopically enriched" means that the occurrence of the isotope is beyond the natural abundance. A 5'-cap compound of the present invention which is isotopically labeled or RNAs modified with such an isotopically labeled 5'-cap compound of the present application can be produced by using correspondingly isotopically labeled nucleotides during the in vitro transcription or by adding such correspondingly isotopically labeled nucleotides after transcription.

The phrase "the stereochemical configuration at the P atom comprising the substituent $R^5$ corresponds to that at the P$_\beta$ atom of the D1 diastereomer of beta-S-ARCA" means that a phosphorous atom comprising the substituent $R^5$ and having a chiral center, and therefore capable of existing in either of two stereochemical configurations, is present in predominately one desired stereochemical configuration, i.e., that at the P$_\beta$ atom of the D1 diastereomer of beta-S-ARCA. As the case may be for the P$_\beta$ atom of the D1 diastereomer of beta-S-ARCA this could either be the (R) configuration or the (S) configuration. Preferably, greater than 50% of the group of interest has the desired stereochemical configuration, preferably at least 75% of the group of interest has the desired stereochemical configuration, more preferably at least 90% of the group of interest has the desired stereochemical configuration, even more preferably at least 95% of the group of interest has the desired stereochemical configuration, and most preferably at least 99% of the group of interest has the desired stereochemical configuration.

The D1 diastereomer of beta-S-ARCA (β-S-ARCA) has the following structure:

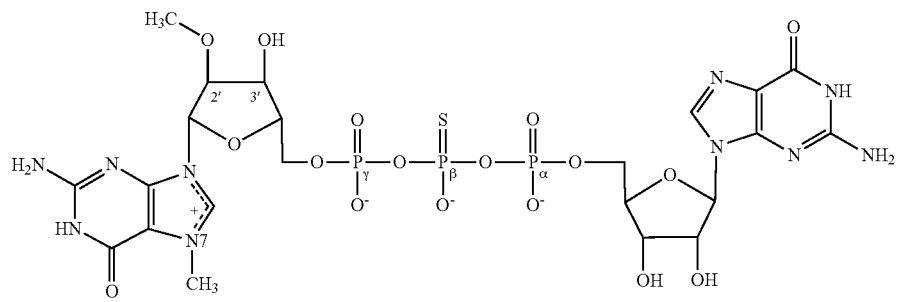

The "D1 diastereomer of beta-S-ARCA" or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time. The HPLC preferably is an analytical HPLC. In one embodiment, a Supelcosil LC-18-T RP column, preferably of the format: 5 μm, 4.6×250 mm is used for separation, whereby a flow rate of 1.3 ml/min can be applied. In one embodiment, a gradient of methanol in ammonium acetate, for example, a 0-25% linear gradient of methanol in 0.05 M ammonium acetate, pH=5.9, within 15 min is used. UV-detection (VWD) can be performed at 260 nm and fluorescence detection (FLD) can be performed with excitation at 280 nm and detection at 337 nm.

The term "naturally occurring", as used herein in context with an object, refers to the fact that an object can be found in nature. For example, a protein, amino acid or nucleic acid that is present in an organism (including viruses), that can be isolated from a source in nature and that has not been intentionally modified by man in the laboratory is naturally occurring.

The present invention relates to modification of RNA, preferably mRNA, to increase the stability and/or expression of said RNA, preferably in immune cells, more preferably in immature immune cells, even more preferably in immature antigen presenting cells, and most preferably in immature dendritic cells. The modified RNA described in the present invention is particularly useful for RNA vaccination.

5'-Cap Compound

In a first aspect, the present application provides a 5'-cap compound having the 5'-cap structure according to formula (I):

formula (I)

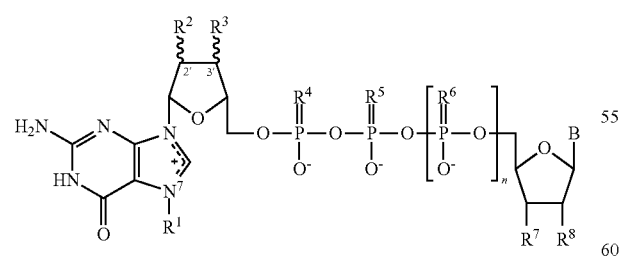

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl;

$R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, optionally substituted $CH_2CH_2$, optionally substituted $CH_2CH_2CH_2$, optionally substituted $CH_2CH(CH_3)$, and optionally substituted C$(CH_3)_2$, or $R^2$ is combined with the hydrogen atom at position 4' of the ring to which $R^2$ is attached to form —O—$CH_2$— or —$CH_2$—O—;

$R^4$ and $R^6$ are independently selected from the group consisting of O, S, Se, and $BH_3$;

$R^5$ is selected from the group consisting of S, Se, and $BH_3$;

$R^7$ is a mononucleotide or an oligonucleotide having 2, 3, 4, 5, 6, 7, 8, or 9 (such as 2, 3, 4, 5, or 6) bases;

$R^8$ is H, halo, or optionally substituted alkoxy;

n is 1, 2, or 3; and

B is a purine or pyrimidine base moiety.

In one embodiment, the 5'-cap compound has the formula (Ia)

formula (Ia)

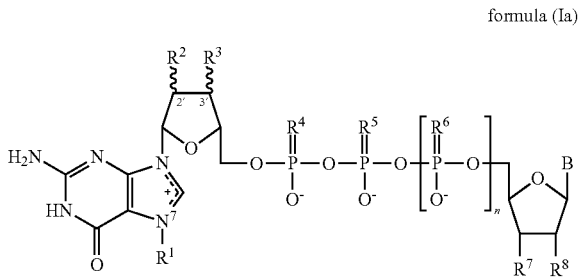

wherein $R^2$, $R^3$, $R^4$, $R^5$, $R^6$, $R^7$, $R^8$, n, and B are as defined above or below and $R^1$ is selected such that the 5'-cap compound does not inhibit translation of the RNA comprising said 5'-cap compound. In one embodiment of the 5'-cap compound of formula (Ia), $R^1$ is selected such that the capped RNA, in particular the 5'-cap structure of the capped RNA is recognized by the translation initiation machinery, preferably in vivo and in vitro, preferably the capped RNA, in particular the 5'-cap structure of the capped RNA is recognized by the eukaryotic translation initiation machinery. For example, the skilled person may determine whether a capped RNA or the 5'-cap structure of the capped RNA is recognized by the eukaryotic translation initiation machinery by determining the affinity of the eukaryotic translation initiation factor eIF4E for said capped RNA or said 5'-cap structure.

In one embodiment of the 5'-cap compound of formula (Ia), $R^1$ is selected from the group consisting of optionally substituted $C_1$-$C_4$ alkyl (e.g., methyl, ethyl, propyl, butyl, benzyl, phenylethyl, and naphthylmethyl, any of which may be optionally substituted); optionally substituted $C_2$-$C_4$ alkenyl (e.g., ethenyl, propenyl, or butenyl, any of which may be optionally substituted), and optionally substituted aryl. In a preferred embodiment of the 5'-cap compound of formula (Ia), $R^1$ is selected from the group consisting of $C_1$-$C_4$ alkyl and optionally substituted aryl. In a preferred embodiment of the 5'-cap compound of formula (Ia), $R^1$ is selected from the group consisting of methyl, ethyl, optionally substituted benzyl, optionally substituted phenylethyl, and optionally substituted naphthylmethyl. In a preferred embodiment of the 5'-cap compound of formula (Ia), $R^1$ is methyl or ethyl, more preferably methyl.

In one embodiment, the 5'-cap compound has the formula (Ib)

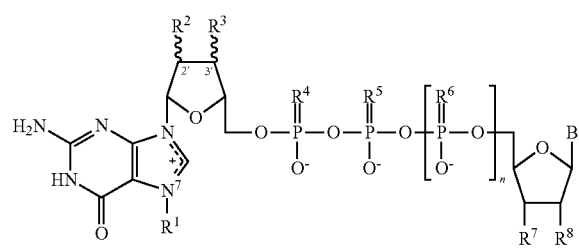

formula (Ib)

wherein $R^1$, $R^4$, $R^5$, $R^6$, $R^7$, $R^8$, n, and B are as defined above (in particular with respect to one or more of formulas (I) and (Ia)) or below and the configuration of $R^2$ and $R^3$ is such that the 5'-cap compound can only be incorporated into an RNA chain in one orientation. Pasquinelli et al. (1995, RNA J. 1: 957-967) have demonstrated that during in vitro transcription bacteriophage RNA polymerases use the 7-methylguanosine unit for initiation of transcription whereby around 40-50% of the transcripts with cap possess the cap-dinucleotide in a reverse orientation (i.e., the initial reaction product is Gpppm$^7$GpN). Compared to the RNAs containing a cap structure in the correct orientation RNAs containing a cap structure in reverse orientation (also called RNAs with a reverse cap) are not functional with respect to translation of the encoded proteins. Thus, it is desirable to incorporate the cap in the correct orientation, i.e., resulting in an RNA with a cap structure essentially corresponding to m$^7$GpppGpN etc. It has been shown that the reverse integration of the cap-dinucleotide is inhibited by the substitution of either the 2'- or the 3'—OH group of the methylated guanosine unit (Stepinski et al., 2001; RNA J. 7:1486-1495; Peng et al., 2002; Org. Lett. 24:161-164). RNAs which are synthesized in presence of such "anti reverse cap analogs", i.e., ARCAs, are translated more efficiently than RNAs which have been in vitro transcribed in presence of the conventional 5'-cap m$^7$GpppG. Furthermore, Kore et al. (J. Am. Chem. Soc. 2009, 131: 6364-6365) found that locked nucleic acid (LNA)-modified dinucleotide mRNA cap analogues are also not incorporated in the reverse orientation into an RNA strand.

Consequently, in a preferred embodiment of the 5'-cap compound of formula (Ib), $R^1$ is selected such that the eukaryotic translation initiation machinery is capable of recognizing the RNA capped with the 5'-cap compound of the present invention and at least one (or both of) $R^2$ and $R^3$ is (are) selected such that the 5'-cap compound cannot be incorporated in reverse orientation into an RNA strand.

In one embodiment of the 5'-cap compound of formula (Ib), $R^2$ and $R^3$ are independently selected from the group consisting of H, F, OH, methoxy, ethoxy, propoxy, and 2-methoxyethoxy. In a preferred embodiment of the 5'-cap compound of formula (Ib), one of $R^2$ and $R^3$ is OH, and the other is not OH. In another preferred embodiment of the 5'-cap compound of formula (Ib), at least one of $R^2$ and $R^3$ is not OH. For example, in one embodiment of the 5'-cap compound of formula (Tb), $R^2$ is selected from the group consisting of H, F, methoxy, ethoxy, propoxy and 2-methoxyethoxy, preferably from the group consisting of H, F, methoxy, ethoxy, and propoxy.

In any one of the embodiments of the 5'-cap compound of formula (Ib) described above, the ring structure comprising the substituents $R^2$ and $R^3$ may have the stereochemical configuration of ribose. In this embodiment, it is preferred that at least one of $R^2$ and $R^3$ is not OH.

In those of the above embodiments, where $R^2$ (or $R^3$) is not OH it is preferably selected from the group consisting of H, halo, and optionally substituted $C_1$-$C_{10}$ alkoxy, more preferably from the group consisting of H, F, methoxy, ethoxy, propoxy, and 2-methoxyethoxy, more preferably from the group consisting of H, F, methoxy, ethoxy, and propoxy. More preferably, it is methoxy.

In a preferred embodiment of the 5'-cap compound of formula (Ib), in particular when the ring structure comprising the substituents $R^2$ and $R^3$ has the stereochemical configuration of ribose, $R^2$ is OH and $R^3$ is methoxy or $R^2$ is methoxy and $R^3$ is OH.

In one embodiment of the 5'-cap compound of formula (Ib), $R^2$ and $R^3$ together form O—X—O, wherein X is selected from the group consisting of $CH_2$ and $C(CH_3)_2$, both of which may be optionally substituted.

In one embodiment of the 5'-cap compound of formula (Ib), the stereochemical configuration of the ring structure comprising the substituents $R^2$ and $R^3$ does not correspond to the stereochemical configuration of ribose. For example, the stereochemical configuration of the ring structure comprising the substituents $R^2$ and $R^3$ may correspond to the stereochemical configuration of arabinose, xylose, or lyxose, in particular when the stereochemical configuration of said ring structure corresponds to that of arabinose. In these embodiments, it is preferred that $R^2$ and $R^3$ are both OH. However, in these embodiments, it is also possible that $R^2$ and $R^3$ are selected as specified above.

In one embodiment, the 5'-cap compound has the formula (Ic)

formula (Ic)

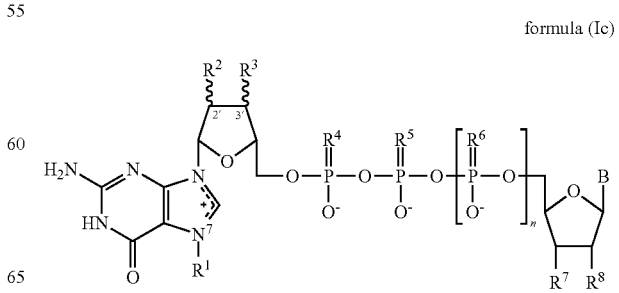

wherein $R^1$, $R^2$, $R^3$, $R^4$, $R^6$, $R^7$, $R^8$, n, and B are as defined above (in particular with respect to one or more of formulas (I), (Ia), and (Ib)) or below and $R^5$ is S or Se, preferably S. In one embodiment of the 5'-cap compound of formula (Ic), $R^5$ is S or Se, preferably S, and n is 1 or 2. In one embodiment of the 5'-cap compound of formula (Ic), $R^5$ is S and n is 1 or 2, preferably 1. In any of the above embodiments of the 5'-cap compound of formula (Ic), it is preferred that $R^4$ and $R^6$ are independently selected from the group consisting of O, Se, and S, more preferably from the group consisting of O and S. In any of the above embodiments, wherein n is 2 or 3, it is to be understood that $R^6$ may independently be selected for each [$R^6PO_2$] moiety. For example, if n is 2, the 5'-cap compound contains two [$R^6PO_2$] moieties, wherein the two $R^6$ residues may be the same (e.g., $R^6$ in both [$R^6PO_2$] moieties is O) or different (e.g., $R^6$ in one [$R^6PO_2$] moiety is O, whereas $R^6$ in the other [$R^6PO_2$] moiety is S). In one embodiment of the 5'-cap compound of formula (Ic), $R^5$ is S or Se, preferably S, n is 1 or 2, preferably 1, and $R^4$ and $R^6$ are independently selected from the group consisting of O and S, more preferably $R^4$ and $R^6$ are O. In one embodiment of the 5'-cap compound of formula (Ic), $R^5$ is S, n is 1 or 2, preferably 1, and $R^4$ and $R^6$ are O.

In one embodiment of the 5'-cap compound of formula (Ic), the stereochemical configuration at the P atom comprising the substituent $R^5$ corresponds to that at the $P_\beta$ atom of the D1 diastereomer of beta-S-ARCA.

In one embodiment, the 5'-cap compound has the formula (Id)

formula (Id)

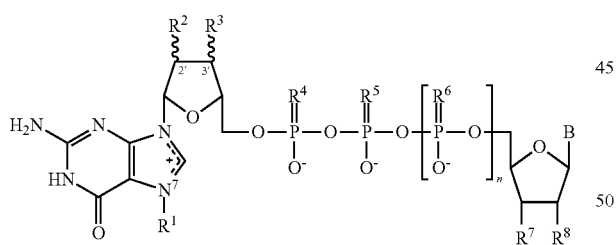

wherein $R^1$, $R^2$, $R^3$, $R^4$, $R^5$, $R^6$, $R^8$, n, and B are as defined above (in particular with respect to one or more of formulas (I), (Ia), (Ib), and (Ic)) or below and $R^7$ is bonded via its 5'-end to the ring to which $R^8$ is attached. In one embodiment of the 5'-cap compound of formula (Id), $R^7$ is a ribomononucleotide or ribooligonucleotide. In one preferred embodiment of the 5'-cap compound of formula (Id), $R^7$ is a ribonucleotide having a free OH group at position 2'. In another preferred embodiment of the 5'-cap compound of formula (Id), $R^7$ is a ribooligonucleotide, wherein both the ribose moiety at the 3'-end of the ribooligonucleotide and the ribose moiety at the 5'-end of the ribooligonucleotide have a free OH group at position 2'. In another preferred embodiment of the 5'-cap compound of formula (Id), $R^7$ is a ribooligonucleotide, wherein the OH group at position 2' of at least the ribose at the 5'-end of the ribooligonucleotide is replaced with a substituent selected from the group consisting of H, halo, and optionally substituted alkoxy (such as H, F, methoxy, ethoxy, propoxy, or 2-methoxyethoxy, preferably H, F, methoxy, ethoxy, or propoxy, most preferably methoxy), and the ribose at the 3'-end of the ribooligonucleotide has a free OH group at position 2'. In any of the above embodiments of formula (Id), it is preferred that the internucleotide linkage between the mononucleotide or oligonucleotide and the ring to which $R^7$ is attached is selected from the group consisting of phosphate, phosphorothioate, boranophosphate, imidophosphate, alkylene phosphate, phosphorodithioate, alkylphosphonate, phosphotriester, phosphoroamidite, and non-nucleotide linker, preferably from the group consisting of phosphate, phosphorothioate, and phosphorodithioate (in one embodiment the internucleotide linkage between the mononucleotide or oligonucleotide and the ring to which $R^7$ is attached is phosphate). In any of the above embodiments of formula (Id), where $R^7$ is an oligonucleotide, in particular a ribooligonucleotide, it is preferred that the internucleotide linkage(s) between the nucleotides in the oligonucleotide is(are) selected from the group consisting of phosphate, phosphorothioate, boranophosphate, imidophosphate, alkylene phosphate, phosphorodithioate, alkylphosphonate, phosphotriester, phosphoroamidite, and non-nucleotide linker, preferably from the group consisting of phosphate, phosphorothioate, and phosphorodithioate (in one embodiment the internucleotide linkage(s) between the nucleotides in the oligonucleotide is(are) phosphate). In one embodiment of the 5'-cap compound of formula (Id), $R^7$ is *[pN($R^{8'}$)]$_a$[pN]$_b$, wherein * indicates the attachment point of $R^7$ to the ring to which $R^7$ is attached; each N($R^{8'}$) is a nucleoside (preferably adenosine, guanosine, uridine, 5-methyluridine, or cytidine) which is substituted with $R^{8'}$ (being selected from the group consisting of H, halo, and optionally substituted alkoxy, preferably from the group consisting of H, F, methoxy, ethoxy, propoxy and 2-methoxyethoxy, more preferably from the group consisting of H, F, methoxy, ethoxy, and propoxy, most preferably methoxy) at position 2'; each N is a ribonucleoside (preferably adenosine, guanosine, uridine, 5-methyluridine, or cytidine) having a free OH group at position 2'; each p is a phosphate moiety; a is 0, 1, 2, 3, 4, 5, 6, 7, or 8; b is 1, 2, 3, 4, 5, 6, 7, 8, or 9; and a+b is 1, 2, 3, 4, 5, 6, 7, 8, or 9 (preferably a is 0, 1, or 2; b is 1, 2, 3, 4, 5, or 6; and a+b is 1, 2, 3, 4, 5, or 6). In one embodiment of the 5'-cap compound of formula (Id), $R^7$ is *pGpN or *pG, wherein N is adenosine, guanosine, uridine, 5-methyluridine, or cytidine and wherein * indicates the attachment point of $R^7$ to the ring to which $R^7$ is attached. In one embodiment of the 5'-cap compound of formula (Id), $R^7$ is *pm$^{2'-O}$GpN, wherein N is adenosine, guanosine, uridine, 5-methyluridine, or cytidine and wherein * indicates the attachment point of $R^7$ to the ring to which $R^7$ is attached.

In one embodiment, the 5'-cap compound has the formula (Ie)

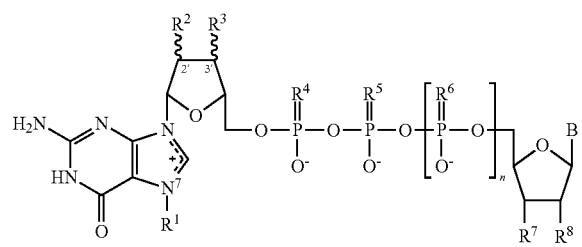

formula (Ie)

wherein $R^1$, $R^2$, $R^3$, $R^4$, $R^5$, $R^6$, $R^7$, $R^8$, and n are as defined above (in particular with respect to one or more of formulas (I), (Ia), (Ib), (Ic), and (Id)) or below and B is a naturally occurring purine or pyrimidine base moiety or a modified form thereof. In one embodiment of the 5'-cap compound of formula (Ie), B is selected from the group consisting of guanine, adenine, cytosine, thymine, uracil, and modified forms thereof, preferably from the group consisting of guanine, adenine, cytosine, uracil, and modified forms thereof, more preferably from the group consisting of guanine, adenine, cytosine, and modified forms thereof, more preferably from the group consisting of guanine, adenine, and modified forms thereof. In one embodiment of the 5'-cap compound of formula (Ie), the modified purine or pyrimidine base moiety is modified by one or more alkyl groups, preferably one or more $C_{1-4}$alkyl groups, more preferably one or more methyl groups. In a preferred embodiment of the 5'-cap compound of formula (Ie), the modified purine or pyrimidine base moiety is selected from the group consisting of $N^7$-alkyl-guanine, $N^6$-alkyl-adenine, 5-alkyl-cytosine, 5-alkyl-uracil, and N(1)-alkyl-uracil, preferably from the group consisting of $N^7$—$C_{1-4}$alkyl-guanine, $N^6$—$C_{1-4}$alkyl-adenine, 5-$C_{1-4}$alkyl-cytosine, 5-$C_{1-4}$alkyl-uracil, and N(1)-$C_{1-4}$alkyl-uracil, more preferably from the group consisting of N'-methyl-guanine, $N^6$-methyl-adenine, 5-methyl-cytosine, 5-methyl-uracil, and N(1)-methyl-uracil. In a preferred embodiment of the 5'-cap compound of formula (Ie), the naturally occurring purine or pyrimidine base moiety is G or A, preferably G. In a more preferred embodiment of the 5'-cap compound of formula (Ie), B is G or A, preferably G.

In any of the above embodiments of the 5'-cap compound of any one of formulas (I), (Ia), (Ib), (Ic), (Id), and (Ie), it is preferred that $R^8$ is selected from the group consisting of H, F, methoxy, ethoxy, propoxy, and 2-methoxyethoxy, more preferably from the group consisting of H, F, methoxy, ethoxy, and propoxy. Most preferably, in any of the above embodiments of the 5'-cap compound any one of formulas (I), (Ia), (Ib), (Ic), (Id), and (Ie), $R^8$ is methoxy.

In one embodiment, the 5'-cap compound has the formula (II)

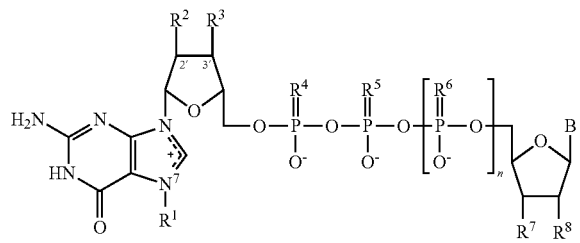

formula (II)

wherein $R^1$ is selected from the group consisting of optionally substituted $C_1$-$C_4$ alkyl and optionally substituted aryl;

$R^2$ and $R^3$ are independently selected from the group consisting of H, F, OH, methoxy, ethoxy, propoxy, and 2-methoxyethoxy;

$R^4$ and $R^6$ are independently selected from the group consisting of O and S;

$R^5$ is S or Se;

$R^7$ is a ribomononucleotide or a ribooligonucleotide having 2, 3, 4, 5, or 6 (such as 2 or 3) bases;

$R^8$ is selected from the group consisting of H, F, methoxy, ethoxy, propoxy, and 2-methoxyethoxy;

n is 1, 2, or 3; and

B is a purine or pyrimidine base moiety.

In one embodiment, the 5'-cap compound has the formula (IIa)

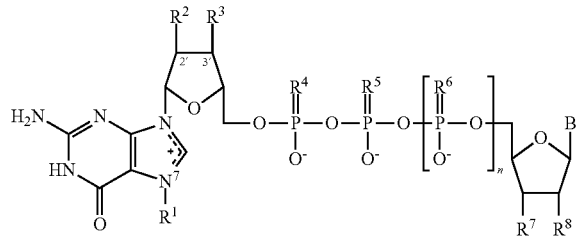

formula (IIa)

wherein $R^2$, $R^3$, $R^4$, $R^1$, $R^6$, $R^7$, $R^8$, n, and B are as defined above (in particular with respect to one or more of formulas (I), (Ia), (Ib), (Ic), (Id), (Ie), and (II)) or below and $R^1$ is selected from the group consisting of methyl, ethyl, benzyl, phenylethyl, and naphthylmethyl, more preferably from the group consisting of methyl and ethyl. In a preferred embodiment of the 5'-cap compound of formula (IIa), $R^1$ is methyl or ethyl, more preferably methyl.

In one embodiment, the 5'-cap compound has the formula (IIb)

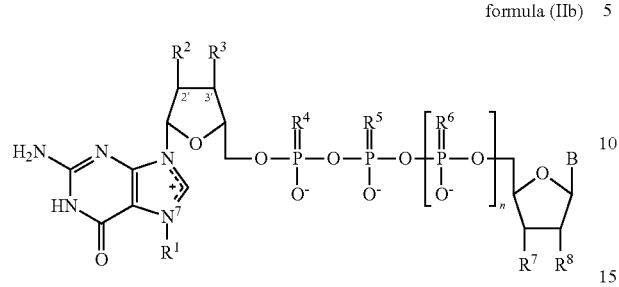

formula (IIb)

wherein $R^1$, $R^4$, $R^5$, $R^6$, $R^7$, $R^8$, n, and B are as defined above (in particular with respect to one or more of formulas (I), (Ia), (Ib), (Ic), (Id), (Ie), (II), and (IIa)) or below and at least one of $R^2$ and $R^3$ is not OH. In one embodiment of the 5'-cap compound of formula (IIb), one of $R^2$ and $R^3$ is OH, and the other is not OH. In one embodiment of the 5'-cap compound of formula (IIb), the ring structure comprising the substituents $R^2$ and $R^3$ has the stereochemical configuration of ribose. In this embodiment, it is preferred that at least one of $R^2$ and $R^3$ is not OH. In those of the above embodiments, where $R^2$ (or $R^3$) is not OH it is preferably selected from the group consisting of H, F, methoxy, ethoxy, and propoxy. More preferably, it is methoxy.

In a preferred embodiment of the 5'-cap compound of formula (IIb), in particular when the ring structure comprising the substituents $R^2$ and $R^3$ has the stereochemical configuration of ribose, Rz is OH and $R^3$ is methoxy or $R^2$ is methoxy and $R^3$ is OH.

In one embodiment of the 5'-cap compound of formula (IIb), the stereochemical configuration of the ring structure comprising the substituents $R^2$ and $R^3$ does not correspond to the stereochemical configuration of ribose. For example, the stereochemical configuration of the ring structure comprising the substituents $R^2$ and $R^3$ may correspond to the stereochemical configuration of arabinose, xylose, or lyxose, in particular when the stereochemical configuration of said ring structure corresponds to that of arabinose. In these embodiments, it is preferred that $R^2$ and $R^3$ are both OH. However, in these embodiments, it is also possible that $R^2$ and $R^3$ are selected as specified above.

In one embodiment, the 5'-cap compound has the formula (IIc)

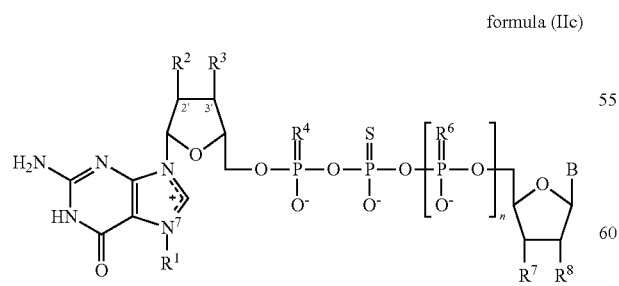

formula (IIc)

wherein $R^1$, $R^2$, $R^3$, $R^4$, $R^6$, $R^7$, $R^8$, n, and B are as defined above (in particular with respect to one or more of formulas (I), (Ia), (Ib), (Ic), (Id), (Ie), (II), (IIa), and (IIb)) or below. In one embodiment of the 5'-cap compound of formula (IIc), n is 1 or 2. In any of the above embodiments, wherein n is 2 or 3, it is to be understood that $R^6$ may independently selected for each $[R^6PO_2]$ moiety. For example, if n is 2, the 5'-cap compound contains two $[R^6PO_2]$ moieties, wherein the two $R^6$ residues may be the same (e.g., $R^6$ in both $[R^6PO_2]$ moieties is O) or different (e.g., $R^6$ in one $[R^6PO_2]$ moiety is O, whereas $R^6$ in the other $[R^6PO_2]$ moiety is S). In one embodiment of the 5'-cap compound of formula (IIc), $R^4$ and $R^6$ are O. In one embodiment of the 5'-cap compound of formula (IIc), n is 1 or 2, preferably 1, and $R^4$ and $R^6$ are O.

In one embodiment, the 5'-cap compound has the formula (IId)

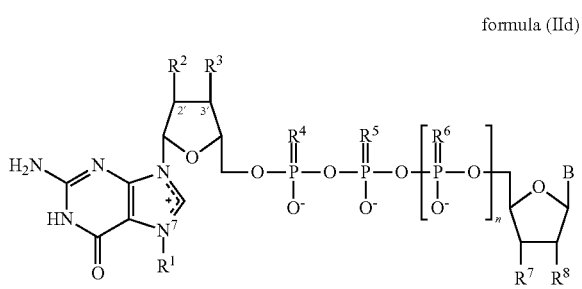

formula (IId)

wherein $R^1$, $R^2$, $R^3$, $R^4$, $R^1$, $R^6$, $R^8$, n, and B are as defined above (in particular with respect to one or more of formulas (I), (Ia), (Ib), (Ic), (Id), (Ie), (II), (IIa), (IIb), and (IIc)) or below and $R^7$ is bonded via its 5'-end to the ring to which $R^8$ is attached. In one preferred embodiment of the 5'-cap compound of formula (IId), $R^7$ is a ribonucleotide having a free OH group at position 2'. In another preferred embodiment of the 5'-cap compound of formula (IId), $R^7$ is a ribooligonucleotide, wherein both the ribose moiety at the 3'-end of the ribooligonucleotide and the ribose moiety at the 5'-end of the ribooligonucleotide have a free OH group at position 2'. In another preferred embodiment of the 5'-cap compound of formula (IId), $R^7$ is a ribooligonucleotide, wherein the OH group at position 2' of at least the ribose at the 5'-end of the ribooligonucleotide is replaced with a substituent selected from the group consisting of H, halo, and optionally substituted alkoxy (such as H, F, methoxy, ethoxy, propoxy, or 2-methoxyethoxy, preferably H, F, methoxy, ethoxy, or propoxy, most preferably methoxy), and the ribose at the 3'-end of the ribooligonucleotide has a free OH group at position 2'. In any of the above embodiments of formula (IId), it is preferred that the internucleotide linkage between the mononucleotide or oligonucleotide and the ring to which $R^7$ is attached is selected from the group consisting of phosphate, phosphorothioate, boranophosphate, imidophosphate, alkylene phosphate, phosphorodithioate, alkylphosphonate, phosphotriester, phosphoroamidite, and non-nucleotide linker, more preferably the internucleotide linkage between the mononucleotide or oligonucleotide and the ring to which $R^7$ is attached is phosphate. In any of the above embodiments of formula (IId), where $R^7$ is an oligonucleotide, in particular a ribooligonucleotide, it is preferred that the internucleotide linkage(s) between the nucleotides in the oligonucleotide is(are) selected from the group consisting of phosphate, phosphorothioate, boranophosphate, imidophosphate, alkylene phosphate, phosphorodithioate, alkylphosphonate, phosphotriester, phosphoroamidite, and non-nucleotide linker, more preferably the internucleotide linkage(s) between the nucleotides in the oligonucleotide is(are) phosphate. In one embodiment of the 5'-cap compound of formula (IId), $R^7$ is *$[pN(R^{8'})]_a[pN]_b$, wherein * indicates the attachment point of $R^7$ to the ring to which $R^7$ is attached; each $N(R^{8'})$ is a nucleoside (preferably adenosine, guanosine, uridine, 5-methyluridine, or cytidine) which is substituted with $R^{8'}$ (being selected from the group consisting of H, halo, and optionally substituted alkoxy, preferably from the group consisting of H, F, methoxy, ethoxy, propoxy and 2-methoxyethoxy, more preferably from the group consisting of H, F, methoxy, ethoxy, and propoxy, most preferably methoxy) at position 2'; each N is a ribonucleoside (preferably adenosine, guanosine, uridine, 5-methyluridine, or cytidine) having a free OH group at position 2'; each p is a phosphate moiety; a is 0, 1, 2, 3, 4, 5, 6, 7, or 8; b is 1, 2, 3, 4, 5, 6, 7, 8, or 9; and a+b is 1, 2, 3, 4, 5, 6, 7, 8, or 9 (preferably a is 0, 1, or 2; b is 1, 2, 3, 4, 5, or 6; and a+b is 1, 2, 3, 4, 5, or 6). In one embodiment of the 5'-cap compound of formula (IId), $R^7$ is *pGpN or *pG, wherein N is adenosine, guanosine, uridine, 5-methyluridine, or cytidine and wherein * indicates the attachment point of $R^7$ to the ring to which $R^7$ is attached. In one embodiment of the 5'-cap compound of formula (IId), $R^7$ is *$pm^{2'-O}GpN$, wherein N is adenosine, guanosine, uridine, 5-methyluridine, or cytidine and wherein * indicates the attachment point of $R^7$ to the ring to which $R^7$ is attached.

In one embodiment, the 5'-cap compound has the formula (IIe)

formula (IIe)

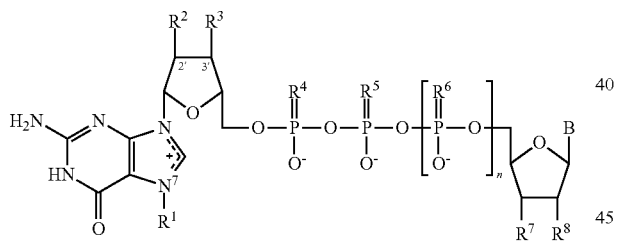

wherein $R^1$, $R^2$, $R^3$, $R^4$, $R^5$, $R^6$, $R^7$, $R^8$, and n are as defined above (in particular with respect to one or more of formulas (I), (Ia), (Ib), (Ic), (Id), (Ie), (II), (IIa), (IIb), (IIc), and (IId)) or below and B is a naturally occurring purine or pyrimidine base moiety or a modified form thereof. In one embodiment of the 5'-cap compound of formula (IIe), B is selected from the group consisting of guanine, adenine, cytosine, thymine, uracil, and modified forms thereof, preferably from the group consisting of guanine, adenine, cytosine, uracil, and modified forms thereof, more preferably from the group consisting of guanine, adenine, cytosine, and modified forms thereof, more preferably from the group consisting of guanine, adenine, and modified forms thereof. In one embodiment of the 5'-cap compound of formula (IIe), the modified purine or pyrimidine base moiety is modified by one or more alkyl groups, preferably one or more $C_{1-4}$alkyl groups, more preferably one or more methyl groups. In a preferred embodiment of the 5'-cap compound of formula (IIe), the modified purine or pyrimidine base moiety is selected from the group consisting of $N^7$-alkyl-guanine, $N^6$-alkyl-adenine, 5-alkyl-cytosine, 5-alkyl-uracil, and N(1)-alkyl-uracil, preferably from the group consisting of $N^7$—$C_{1-4}$alkyl-guanine, N'—$C_{1-4}$alkyl-adenine, 5-$C_{1-4}$alkyl-cytosine, 5-$C_{1-4}$alkyl-uracil, and N(1)-$C_{1-4}$alkyl-uracil, more preferably from the group consisting of $N^7$-methyl-guanine, N'-methyl-adenine, 5-methyl-cytosine, 5-methyl-uracil, and N(1)-methyl-uracil. In a preferred embodiment of the 5'-cap compound of formula (IIe), the naturally occurring purine or pyrimidine base moiety is G or A, preferably G. In a more preferred embodiment of the 5'-cap compound of formula (IIe), B is G or A, preferably G.

In any of the above embodiments of the 5'-cap compound of any one of formulas (II), (IIa), (IIb), (IIc), (IId), and (IIe), it is preferred that $R^8$ is selected from the group consisting of H, F, methoxy, ethoxy, and propoxy. Most preferably, in any of the above embodiments of the 5'-cap compound of any one of formulas (II), (IIa), (IIb), (IIc), (IId), and (IIe), $R^8$ is methoxy.

In one embodiment, the 5'-cap compound has the formula (III)

formula (III)

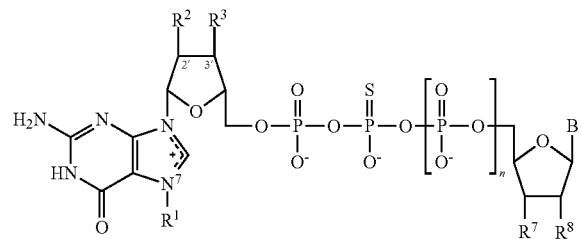

wherein $R^1$ is methyl, ethyl, benzyl, phenylethyl, or naphthylmethyl, more preferably methyl or ethyl;

$R^2$ and $R^3$ are independently selected from the group consisting of H, F, OH, and methoxy, wherein preferably at least one of $R^2$ and $R^3$ is not OH;

$R^7$ is a ribomononucleotide, ribodinucleotide or a ribotrinucleotide bonded via its 5'-end to the ring to which $R^8$ is attached, wherein the internucleotide linkage between the ribomononucleotide, ribodinucleotide or ribotrinucleotide and the ring to which $R^7$ is attached is selected from the group consisting of phosphate, phosphorothioate, and phosphorodithioate, and wherein if $R^7$ is a ribodinucleotide or a ribotrinucleotide, the internucleotide linkage(s) between the nucleotides in the ribodinucleotide or ribotrinucleotide is(are) selected from the group consisting of phosphate, phosphorothioate, and phosphorodithioate;

$R^8$ is selected from the group consisting of H, F, and methoxy;

n is 1 or 2; and

B is selected from the group consisting of guanine, adenine, cytosine, thymine, and uracil, preferably from the group consisting of guanine, adenine, cytosine, and uracil, more preferably from the group consisting of guanine, adenine, and cytosine, more preferably from the group consisting of guanine and adenine.

In one embodiment, the 5'-cap compound has the formula (IIIa)

formula (IIIa)

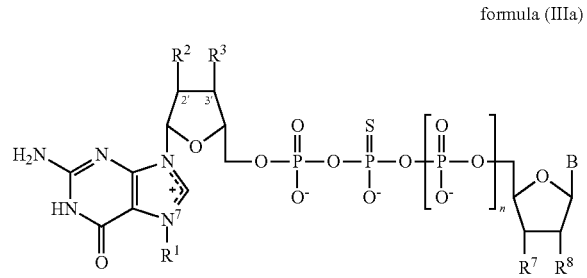

wherein R$^1$ is methyl or ethyl; one of R$^2$ and R$^3$ is OCH$_3$ and the other is OH (e.g., R$^2$ is OCH$_3$ and R$^3$ is OH or R$^2$ is OH and R$^3$ is OCH$_3$); R$^8$ methoxy; n is 1; the internucleotide linkage between the ribomononucleotide, ribodinucleotide or ribotrinucleotide and the ring to which R$^7$ is attached is phosphate or phosphorothioate, preferably phosphate, and wherein if R$^7$ is a ribodinucleotide or a ribotrinucleotide, the internucleotide linkage(s) between the nucleotides in the ribodinucleotide or ribotrinucleotide is(are) phosphate or phosphorothioate, preferably phosphate; and B is guanine or adenine, preferably guanine. In one embodiment of the 5'-cap compound of formula (IIIa), R$^7$ is a ribomononucleotide having a free OH group at position 2'. In another preferred embodiment of the 5'-cap compound of formula (IIIa), R$^7$ is a ribodi- or ribotrinucleotide, wherein both the ribose moiety at the 3'-end of the ribodi- or ribotrinucleotide and the ribose moiety at the 5'-end of the ribodi- or ribotrinucleotide have a free OH group at position 2'. In another preferred embodiment of the 5'-cap compound of formula (IIIa), R$^7$ is a ribodi- or ribotrinucleotide, wherein the OH group at position 2' of at least the ribose at the 5'-end of the ribodi- or ribotrinucleotide is replaced with a substituent selected from the group consisting of H, F, methoxy, ethoxy, propoxy, and 2-methoxyethoxy (preferably from the group consisting of H, F, methoxy, ethoxy, and propoxy, most preferably said substituent is methoxy), and the ribose at the 3'-end of the ribodi- or ribotrinucleotide has a free OH group at position 2'. In one embodiment of the 5'-cap compound of formula (IIIa), R$^7$ is *pGpN or *pG, wherein N is adenosine, guanosine, uridine, 5-methyluridine, or cytidine and wherein * indicates the attachment point of R$^7$ to the ring to which R$^7$ is attached. In one embodiment of the 5'-cap compound of formula (IIIa), R$^7$ is *pm$^{2'-OMe}$GpN, wherein N is adenosine, guanosine, uridine, 5-methyluridine, or cytidine and wherein * indicates the attachment point of R$^7$ to the ring to which R$^7$ is attached.

5'-cap compounds of the present invention can be synthesized starting from commercially available compounds (such as (pN)$_{24}$) using standard procedures. These oligonucleotides can be converted into the corresponding P-imidazolide derivatives by reacting them with imidazole in the presence of an activation system (e.g., 2,2'-dithiodipyridine/triphenylphosphine; cf. FIG. 1 and Mukaiyama and Hashimoto 1971 (Bull. Chem. Soc. Jpn. 44, 2284 (1971))). The nucleotide subunit bearing a modified phosphate bridge (e.g., m2$^{7,2'-OMe}$GDPβS) may be synthesized as described in Kowalska et al. 2008 (RNA 14, 1119-1131 (2008)). Then, the two precursors may be coupled to yield the final 5'-cap compound of the invention; cf. e.g., FIG. 2. Diastereoisomers may be separated by RP HPLC (e.g., using a Discovery Amide RP C16 column).

Preferably, when the 5'-cap compound of the present invention is used to prepare a correspondingly 5'-capped RNA, the 5'-cap structure upon transfer of the 5'-capped RNA into cells is capable of increasing the stability of the RNA, decreasing or inhibiting the recognition of the RNA by proteins recognizing the cap0 structure, e.g., IFIT proteins (in particular IFIT1), increasing translation efficiency of the RNA, prolonging translation of the RNA, increasing total protein expression of the RNA, and/or, if RNA comprises a nucleotide sequence encoding an antigen, increasing the immune response against said antigen when compared to the same RNA without the 5'-cap structure. If RNA comprises a nucleotide sequence encoding an antigen, it is preferred that the cells are immature antigen presenting cells, such as immature dendritic cells. The skilled person may readily determine whether the 5'-cap structure of the 5'-capped RNA is capable of exerting the above functions, for example, by generating two RNAs, e.g., by in vitro transcription, which only differ in the 5'-cap structure, wherein one of the RNA carries a 5'-cap structure according to any one of the formulas (I), (Ia), (Ib), (Ic), (Id), (Ie), (II), (IIa), (IIb), (IIc), (IId), (IIe), (III), and (IIIa) and the other RNA (reference RNA) (i) does not comprise a 5'-cap structure, (ii) carries a conventional mRNA 5'-cap, i.e., a methyl-7-guanosine cap, or (iii) carries any other cap with which the function of the 5'-cap structure according to any one of the formulas (I), (Ia), (Ib), (Ic), (Id), (Ie), (II), (IIa), (IIb), (IIc), (IId), (IIe), (III), and (IIIa) should be compared. For example, the reference RNA may carry a 5'-cap structure which corresponds to the D2 diastereomer of beta-S-ARCA. It is particularly preferred that the 5'-cap structure of the 5'-capped RNA upon transfer of the modified RNA into cells is capable of increasing the stability of the RNA, decreasing or inhibiting the recognition of the RNA by proteins recognizing the cap0 structure e.g., WIT proteins (in particular IFIT1), increasing translation efficiency of the RNA, prolonging translation of the RNA, increasing total protein expression of the RNA, and/or, if RNA comprises a nucleotide sequence encoding an antigen, increasing the immune response against said antigen when compared to a reference RNA, such as the same RNA having a conventional mRNA 5'-cap.

Preferably, the stability and translation efficiency of RNA modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) may be further modified as required. For example, the RNA may be stabilized and its translation increased by one or more modifications having a stabilizing and/or translation efficiency increasing effect. Such modifications are, for example, described in WO 2007/036366 incorporated herein by reference.

For example, RNA having an unmasked poly-A sequence (unmasked poly-A tail) is translated more efficiently than RNA having a masked poly-A sequence. The term "poly-A sequence" relates to a sequence of adenyl (A) residues which typically is located at the 3'-end of an RNA molecule and "unmasked poly-A sequence" means that the poly-A sequence at the 3'-end of an RNA molecule ends with an A of the poly-A sequence and is not followed by nucleotides other than A located at the 3'-end, i.e., down-stream, of the poly-A sequence. Furthermore, a long poly-A sequence of about 120 nucleotides results in optimal transcript stability and translation efficiency.

Thus, the RNA, preferably the mRNA, modified with a 5'-cap compound of the present invention (in particular a 5'-cap compound according to any one of the formulas (I), (Ia), (Ib), (Ic), (Id), (Ie), (II), (IIa), (IIb), (Ic), (IId), (IIe), (III), and (IIIa)) may preferably further comprise a poly-A tail having a length of 10 to 500, preferably having a length of 30 to 300, more preferably having a length of 65 to 200, more preferably having a length of 100 to 150 nucleotides, e.g., 100, 110, 120, 130, 140, or 150 nucleotides, preferably 120 nucleotides. Preferably, said poly-A sequence is an unmasked poly-A sequence. Thus, preferably, the RNA, preferably the mRNA, modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) comprises an unmasked poly-A tail having a length of 10 to 500, preferably having a length of 30 to 300, more preferably having a length of 65 to 200, more preferably having a length of 100 to 150 nucleotides, e.g., 100, 110, 120, 130, 140, or 150 nucleotides, preferably 120 nucleotides.

In addition, incorporation of a 3'-untranslated region (UTR) into the 3'-untranslated region of an RNA molecule can result in an enhancement in translation efficiency. A synergistic effect may be achieved by incorporating two or more of such 3'-UTRs. The 3'-UTRs may be autologous or heterologous to the RNA into which they are introduced, for example, it may be the 3'-UTR of the beta-globin mRNA. Thus, preferably, the RNA, preferably the mRNA, modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) may further comprise one or more copies, preferably two copies of the 3'-untranslated region (3'-UTR) of the beta-globin gene, preferably of the human beta-globin gene.

In addition, the replacement of uridine with pseudouridine or N(1)-methylpseudouridine or 5-methyl-uridine (m5U) resulting in Ψ- or m1Ψ- or m5U-modified RNAs can decrease the immunogenicity of the thus modified RNAs. Therefore, preferably, in the RNA, preferably mRNA, modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) pseudouridine or N(1)-methylpseudouridine or 5-methyluridine (m5U) is substituted partially or completely, preferably completely, for uridine. I.e., in one preferred embodiment, the RNA of the invention is Ψ- or m1Ψ- or m5U-modified or any combination thereof (e.g., Ψ- and m1Ψ-modified or Ψ- and m5U-modified or m1Ψ- and m5U-modified or Ψ- and m1Ψ- and m5U-modified).

In some embodiments, the modified nucleoside replacing one or more uridine in the RNA may be any one or more of 3-methyl-uridine (m3U), 5-methoxy-uridine (mo5U), 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho5U), 5-aminoallyl-uridine, 5-halo-uridine (e.g., 5-iodo-uridineor 5-bromo-uridine), uridine 5-oxyacetic acid (cmo5U), uridine 5-oxyacetic acid methyl ester (mcmo5U), 5-carboxymethyl-uridine (cm5U), 1-carboxymethyl-pseudouridine, 5-carboxyhydroxymethyl-uridine (chm5U), 5-carboxyhydroxymethyl-uridine methyl ester (mchm5U), 5-methoxycarbonylmethyl-uridine (mcm5U), 5-methoxycarbonylmethyl-2-thio-uridine (mcm5s2U), 5-aminomethyl-2-thio-uridine (nm5s2U), 5-methylaminomethyl-uridine (mnm5U), 1-ethyl-pseudouridine, 5-methylaminomethyl-2-thio-uridine (mnm5s2U), 5-methylaminomethyl-2-seleno-uridine (mnm5se2U), 5-carbamoylmethyl-uridine (ncm5U), 5-carboxymethylaminomethyl-uridine (cmnm5U), 5-carboxymethylaminomethyl-2-thio-uridine (cmnm5s2U), 5-propynyl-uridine, 1-propynyl-pseudouridine, 5-taurinomethyl-uridine (τm5U), 1-taurinomethyl-pseudouridine, 5-taurinomethyl-2-thio-uridine (τm5s2U), 1-taurinomethyl-4-thio-pseudouridine), 5-methyl-2-thio-uridine (m5s2U), 1-methyl-4-thio-pseudouridine (m1s4ψ), 4-thio-1-methyl-pseudouridine, 3-methyl-pseudouridine (m3ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m5D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl) uridine (acp3U), 1-methyl-3-(3-amino-3-carboxypropyl) pseudouridine (acp3 ψ), 5-(isopentenylaminomethyl)uridine (inm5U), 5-(isopentenylaminomethyl)-2-thio-uridine (inm5s2U), α-thio-uridine, 2'-O-methyl-uridine (Um), 5,2'-O-dimethyl-uridine (m5Um), 2'-O-methyl-pseudouridine (ψm), 2-thio-2'-O-methyl-uridine (s2Um), 5-methoxycarbonylmethyl-2'-O-methyl-uridine (mcm5Um), 5-carbamoylmethyl-2'-O-methyl-uridine (ncm5Um), 5-carboxymethylaminomethyl-2'-O-methyl-uridine (cmnm5Um), 3,2'-O-dimethyl-uridine (m3Um), 5-(isopentenylaminomethyl)-2'-O-methyl-uridine (inm5Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

It is particularly preferred that the RNA, preferably the mRNA, modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) is modified by a combination of the above described modifications, i.e., by at least two (e.g., at least 3 or by all 4) of the following modifications: incorporation of a poly-A sequence, unmasking of a poly-A sequence, incorporation of one or more 3'-UTRs, and replacement of uridine with pseudouridine or N(1)-methylpseudouridine or 5-methyluridine or a combination thereof.

In a particularly preferred embodiment, the RNA, preferably the mRNA, modified with a 5'-cap compound of the present invention (in particular a 5'-cap compound according to any one of the formulas (I), (Ia), (Ib), (Ic), (Id), (Ie), (II), (IIa), (IIb), (IIc), (IId), (IIe), (III), and (IIIa)) encodes a pharmaceutically active peptide or protein, e.g., selected from the group consisting of cytokines, such as erythropoietin; adhesion molecules, such as an integrin; immunoglobulins; immunologically active compounds, e.g., antigens, such as tumor-associated antigens, pathogen-associated antigens (e.g., one or more (e.g., 1, 2, 3, 4, 5, 6, 7, 8, 9, or 10) antigens of a virus, such as one or more (e.g., 1, 2, 3, 4, 5, 6, 7, 8, 9, or 10) antigens of influenza virus (A, B, or C), CMV, or RSV), allergens, or autoantigens; hormones, such as vasopressin, insulin or growth hormone; growth factors, such as VEGFA; enzymes, such as herpes simplex virus type 1 thymidine kinase (HSV1-TK), hexosaminidase, phenylalanine hydroxylase, pseudocholinesterase, pancreatic enzymes, or lactase; receptors, such as growth factor receptors; protease inhibitors, such as alpha 1-antitrypsin; apoptosis regulators, such as BAX; transcription factors, such as FOXP3; tumor suppressor proteins, such as p53; structural proteins, such as surfactant proteins; reprogramming factors, such as OCT4, SOX2, c-MYC, KLF4, LIN28, or NANOG; genomic engineering proteins, such as clustered regularly spaced short palindromic repeat-CRISPR-associated protein 9 (CRISPR-Cas9); and blood proteins, such as fibrinogen. For example, the pharmaceutically active peptide or protein may be a peptide or protein comprising an immunogen, antigen or antigen peptide, wherein the peptide or protein may be processed after expression to provide said immunogen, antigen or antigen peptide. Alternatively, the peptide or protein itself may be the immunogen, antigen or antigen peptide.

Compositions and Kits

In a further aspect, the present invention provides a composition or kit comprising a 5'-cap compound of the present invention. Such composition or kit may be used for providing an RNA with a 5'-cap structure of the present invention and/or for increasing the stability of an RNA, e.g., in the corresponding methods disclosed herein. In one embodiment of this aspect, the kit may further comprise reagents typically used in in vitro transcription reactions (e.g., NTPs, an RNA polymerase, one or more buffers, and/or a DNA template) and/or instructions for use.

In a further aspect, the present invention provides a composition, preferably a pharmaceutical composition, comprising an RNA (preferably mRNA) modified with a 5'-cap compound of the present invention (such composition comprising an RNA of the invention is also referred to herein as RNA composition of the invention). The composition, in particular pharmaceutical composition, of this aspect may comprise the RNA (preferably mRNA) modified with a 5'-cap compound of the present invention in combination with and one or more pharmaceutically acceptable excipients. In one embodiment, the pharmaceutical composition comprises an RNA (preferably mRNA) modified with a 5'-cap compound of the present invention, one or more pharmaceutically acceptable excipients and one or more additional/supplementary active compounds.

In a further aspect, the present application provides a pharmaceutical composition as specified herein for use in therapy.

For example, in particular in those embodiments where the RNA modified with a 5'-cap compound of the present invention comprises a nucleotide sequence encoding a peptide or protein, the pharmaceutical compositions of the present invention may be used in protein replacement therapy, genome engineering therapy, genomic reprogramming therapy, or immunotherapy.

Illustrative applications of protein replacement therapy for the RNA or pharmaceutical compositions of the present invention include the treatment (including prophylactic treatment) of a condition, disorder or disease caused by a decreased activity of a peptide or protein, e.g., anemia (replacement protein: e.g., erythropoietin), diabetes (replacement protein: e.g., vasopressin), congenital lung disease (replacement protein: e.g., surfactant protein B), asthma (replacement protein: e.g., FOXP3), myocardial infarction (replacement protein: e.g., VEGFA), melanoma (replacement protein: e.g., BAX), autoimmune diabetes (replacement protein: e.g., IL-4), autoimmune myocarditis (replacement protein: e.g., IL-10), inflammation (replacement proteins: e.g., P-selectin glycoprotein ligand-1 (PSGL-1), Sialyl-Lewisx (SLeX), and IL-10)), factor VII deficiency (replacement protein: e.g., factor VIIa), hemophilia A (replacement protein: e.g., factor VIII), hemophilia B (replacement protein: e.g., factor IX), factor X deficiency (replacement protein: e.g., factor X), factor XI deficiency (replacement protein: e.g., factor XI), factor XIII deficiency (replacement protein: e.g., factor XIII), von Willebrand disease (replacement protein: e.g., von Willebrand factor), protein C deficiency (replacement protein: e.g., protein C), antithrombin deficiency (replacement protein: e.g., antithrombin III), fibrinogen deficiency (replacement protein: e.g., fibrinogen), hereditary angioedema (replacement protein: e.g., C1-esterase inhibitor), α1-PI deficiency (replacement protein: e.g., alpha-1 proteinase inhibitor), Gaucher disease (replacement protein: e.g., glucocerebrosidase), mucopolysaccharidosis I (replacement protein: e.g., alpha-L-iduronidase), mucopolysaccharidosis II (replacement protein: e.g., iduronate sulfatase), mucopolysaccharidosis VI (replacement protein: e.g., N-acetylgalactosamine-4-sulfatase), mucopolysaccharidosis IVA (replacement protein: e.g., N-acetylgalactosamine-6-sulfatase), mucopolysaccharidosis IIIA (replacement protein: e.g., heparan sulfate sulfatase), Fabry disease (replacement protein: e.g., alpha-galactosidase A), Pompe disease (replacement protein: e.g., alpha-glucosidase), Niemann-Pick type B disease (replacement protein: e.g., acid sphingomyelinase), alpha-mannosidosis, (replacement protein: e.g., alpha-mannosidase), metachromatic leukodystrophy (replacement protein: e.g., arylsulphatase A), LAL deficiency (replacement protein: e.g., lysosomal acid lipase (LAL)), sucraseisomaltase deficiency (replacement protein: e.g., sucrose-isomaltase), ADA deficiency (replacement protein: e.g., adenosine deaminase (ADA)), primary IGF-1 deficiency (replacement protein: e.g., insulin-like growth factor 1 (IGF-1)), hypophosphatasia (replacement protein: e.g., alkaline phosphatase), and acute intermittent *porphyria* (replacement protein: e.g., porphobilinogen deaminase).

Illustrative applications of genome engineering therapy for the RNA or pharmaceutical compositions of the present invention include the treatment (including prophylactic treatment) of a condition, disorder or disease selected from the group consisting of X-linked severe combined immunodeficiency (X-SCID) (correction with DNA encoding the interleukin-2 receptor common gamma chain (IL-2Rγ)), Xeroderma pigmentosum (correction with native, i.e., unmutated DNA), and the conditions, disorders and diseases specified above with respect to illustrative applications of protein replacement therapy. A further genome engineering therapy for the RNA or pharmaceutical compositions of the present invention includes genome editing making use of, e.g., CRISPR/CAS.

Illustrative applications of genetic reprogramming therapy for the RNA or pharmaceutical compositions of the present invention include the treatment (including prophylactic treatment) of any of the conditions, disorders and diseases specified above with respect to illustrative applications of protein replacement therapy and/or illustrative applications of genome engineering therapy.

Illustrative immunotherapeutic applications for the pharmaceutical compositions of the present invention include the treatment (including prophylactic treatment) of a condition, disorder or disease selected from the group consisting of infectious diseases (e.g., those caused by a pathogen such as viruses (such as influenza virus (A, B, or C), CMV, or RSV), bacteria, fungi or other microorganisms); an undesirable inflammation (such as an immune disorder); and cancer.

Cancer (medical term: malignant neoplasm) is a class of diseases in which a group of cells display uncontrolled growth (division beyond the normal limits), invasion (intrusion on and destruction of adjacent tissues), and sometimes metastasis (spread to other locations in the body via lymph or blood). These three malignant properties of cancers differentiate them from benign tumors, which are self-limited, and do not invade or metastasize. Most cancers form a tumor, i.e., a swelling or lesion formed by an abnormal growth of cells (called neoplastic cells or tumor cells), but some, like leukemia, do not. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, stomach cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. Examples thereof are lung carcinomas, mamma carcinomas, prostate carcinomas, colon carcinomas, renal cell carcinomas, cervical carcinomas, or metastases of the cancer types or tumors described above. The term cancer according to the invention also comprises cancer metastases.

Examples of cancers treatable with the RNA and pharmaceutical compositions of the present invention include malignant melanoma, all types of carcinoma (colon, renal cell, bladder, prostate, non-small cell and small cell lung carcinoma, etc.), lymphomas, sarcomas, blastomas, gliomas, etc.

Malignant melanoma is a serious type of skin cancer. It is due to uncontrolled growth of pigment cells, called melanocytes.

According to the invention, a "carcinoma" is a malignant tumor derived from epithelial cells. This group represents the most common cancers, including the common forms of breast, prostate, lung and colon cancer.

Lymphoma and leukemia are malignancies derived from hematopoietic (blood-forming) cells.

A sarcoma is a cancer that arises from transformed cells in one of a number of tissues that develop from embryonic mesoderm. Thus, sarcomas include tumors of bone, cartilage, fat, muscle, vascular, and hematopoietic tissues.

Blastic tumor or blastoma is a tumor (usually malignant) which resembles an immature or embryonic tissue. Many of these tumors are most common in children.

A glioma is a type of tumor that starts in the brain or spine. It is called a glioma because it arises from glial cells. The most common site of gliomas is the brain.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor, i.e., a secondary tumor or metastatic tumor, at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system.

Exemplary immune disorders include, but are not limited to, autoimmune diseases (for example, diabetes mellitus, arthritis (including rheumatoid arthritis, juvenile rheumatoid arthritis, osteoarthritis and psoriatic arthritis), multiple sclerosis, encephalomyelitis, myasthenia gravis, systemic lupus erythematosus, autoimmune thyroiditis, dermatitis (including atopic dermatitis and eczematous dermatitis), psoriasis, Sjögren's Syndrome, Crohn's disease, aphthous ulcer, iritis, conjunctivitis, keratoconjunctivitis, ulcerative colitis, asthma, allergic asthma, sepsis and septic shock, inflammatory bowel disorder, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, glomerulonephritis, idiopathic sprue, lichen planus, Graves' disease, sarcoidosis, primary biliary cirrhosis, uveitis posterior, and interstitial lung fibrosis), graft-versus-host disease, cases of transplantation, and allergy such as, atopic allergy.

Exemplary viruses include, but are not limited to, are human immunodeficiency virus (HIV), Epstein-Barr virus (EBV), cytomegalovirus (CMV) (e.g., CMV5), human herpesviruses (HHV) (e.g., HHV6, 7 or 8), herpes simplex viruses (HSV), bovine herpes virus (BHV) (e.g., BHV4), equine herpes virus (EHV) (e.g., EHV2), human T-Cell leukemia viruses (HTLV)5, Varicella-Zoster virus (VZV), measles virus, papovaviruses (JC and BK), hepatitis viruses (e.g., HBV or HCV), myxoma virus, adenovirus, parvoviruses, polyoma virus, influenza viruses (e.g., influenza virus A, influenza virus B, or influenza virus C), respiratory syncytial virus (RSV), papillomaviruses and poxviruses such as vaccinia virus, and molluscum contagiosum virus (MCV), and lyssaviruses. Such virus may or may not express an apoptosis inhibitor. Exemplary diseases caused by viral infection include, but are not limited to, chicken pox, Cytomegalovirus infections, genital herpes, Hepatitis B and C, influenza, and shingles, and rabies.

Exemplary bacteria include, but are not limited to, *Campylobacter jejuni, Enterobacter species, Enterococcus faecium, Enterococcus faecalis, Escherichia coli* (e.g., *E. coli* O157:H7), Group A streptococci, *Haemophilus influenzae, Helicobacter pylori, listeria, Mycobacterium tuberculosis, Pseudomonas aeruginosa, S. pneumoniae, Salmonella, Shigella, Staphylococcus aureus,* and *Staphylococcus epidermidis,* and *Borrelia* and *Rickettsia.* Exemplary diseases caused by bacterial infection include, but are not limited to, anthrax, cholera, diphtheria, foodborne illnesses, leprosy, meningitis, peptic ulcer disease, pneumonia, sepsis, septic shock, syphilis, tetanus, tuberculosis, typhoid fever, and urinary tract infection, and Lyme disease and Rocky Mountain spotted fever.

Particular examples of infectious diseases treatable with the RNA or pharmaceutical compositions of the present invention include viral infectious diseases, such as AIDS (HIV), hepatitis A, B or C, herpes, herpes zoster (chickenpox), German measles (rubella virus), yellow fever, dengue fever; infectious diseases caused by flaviviruses; influenza; infectious diseases caused by RSV; infectious diseases caused by CMV; hemorrhagic infectious diseases (Marburg or Ebola viruses); bacterial infectious diseases (such as Legionnaire's disease (*Legionella*), gastric ulcer (*Helicobacter*), cholera (*Vibrio*), infections by *E. coli,* Staphylococci, *Salmonella* or Streptococci (tetanus); infections by protozoan pathogens such as malaria, sleeping sickness, leishmaniasis, toxoplasmosis, i.e. infections by *Plasmodium, Trypanosoma, Leishmania* and *Toxoplasma*; or fungal infections, which are caused, e.g., by *Cryptococcus neoformans, Histoplasma capsulatum, Coccidioides immitis, Blastomyces dermatitidis* or *Candida albicans.*

For administration according to the invention, in particular, in the form of a pharmaceutical composition (e.g., vaccine composition), RNA may be naked RNA or may be incorporated in a carrier, for example, liposomes or other particles for gene transfer, and is preferably in the form of naked RNA.

The RNA (preferably mRNA) modified with a 5'-cap compound of the present invention or the pharmaceutical compositions of the present invention can be used alone or in conjunction with one or more additional/supplementary active compounds which can be administered prior to, simultaneously with or after administration of the RNA or pharmaceutical composition of the present invention. Such one or more additional/supplementary active compounds include immunosuppressants (e.g., for applications where the induction of an immune response is to be avoided or minimized (e.g., in protein replacement therapies, genome engineering therapies, and genetic reprogramming therapies, as described herein)), nucleic acids (e.g., plasmids) comprising a nucleotide sequence encoding a peptide or protein (in particular in genome engineering therapies, where, for example, said nucleotide sequence is to be inserted into the genome of a patient, e.g., in order to replace the corresponding mutated nucleotide sequence in the genome of the patient), compounds for cell differentiation (e.g., compounds which induce the differentiation of cells having stem cell characteristics into cells expressing a peptide or protein (in particular a pharmaceutically active peptide or protein), in particular in genetic reprogramming therapies), chemotherapeutic drugs for cancer patients (e.g. gemcitabine, etopophos, cis-platin, carbo-platin), antiviral agents, anti-parasite agents, anti-bacterial agents, immunotherapeutic agents (e.g., antigens or fragments thereof (in particular immunogenic fragments thereof)), and adjuvants, and, if administered simultaneously with the RNA of the present invention, may be present in a pharmaceutical composition of the present invention.

In particular in case of a vaccine composition, the one or more additional/supplementary active compounds can comprise an immunotherapeutic agent, preferably an immunotherapeutic agent inducing or effecting a targeted, i.e., specific, immune reaction. Thus, in one embodiment, the RNA and pharmaceutical compositions of the present invention can be used in conjunction with an immunotherapeutic agent, preferably an immunotherapeutic agent inducing or effecting a targeted, i.e., specific, immune reaction. Such immunotherapeutic agents include agents directed against a disease-associated antigen such as therapeutic antibodies or agents inducing an immune response directed against a disease-associated antigen or cells expressing a disease-associated antigen. Useful immunotherapeutic agents include proteins or peptides inducing a B cell or T cell response against the disease-associated antigen or cells expressing the disease-associated antigen. These proteins or peptides may comprise a sequence essentially corresponding to or being identical to the sequence of the disease-associated antigen or one or more fragments thereof. In one embodiment, the protein or peptide comprises the sequence of an MHC presented peptide derived from the disease-associated antigen. Instead of administering the protein or peptide it is also possible to administer nucleic acid, preferably RNA such as mRNA, encoding the protein or peptide. The RNA encoding the protein or peptide may be the RNA (preferably mRNA) modified with a 5'-cap compound of the present invention. Alternatively or additionally, the RNA encoding the protein or peptide may be a different RNA not according to the present invention which RNA may be administered simultaneously with (in this case the RNA may form part of a pharmaceutical composition of the invention) and/or prior to and/or after administration of a pharmaceutical composition of the invention. Accordingly, the pharmaceutical composition of the present invention may be used in genetic vaccination, wherein an immune response is stimulated by introduction into an individual a suitable nucleic acid molecule (DNA or mRNA) which codes for an antigen or a fragment thereof.

In one embodiment, a disease-associated antigen is a tumor-associated antigen. In this embodiment, the RNA (preferably mRNA) modified with a 5'-cap compound of the present invention and the pharmaceutical compositions of the present invention may be useful in treating cancer or cancer metastasis. Preferably, the diseased organ or tissue is characterized by diseased cells such as cancer cells expressing a disease-associated antigen and/or being characterized by association of a disease-associated antigen with their surface. Immunization with intact or substantially intact tumor-associated antigen or fragments thereof such as MHC class I and class II peptides or nucleic acids, in particular mRNA, encoding such antigen or fragment makes it possible to elicit a MHC class I and/or a class II type response and thus, stimulate T cells such as CD8+ cytotoxic T lymphocytes which are capable of lysing cancer cells and/or CD4+ T cells. Such immunization may also elicit a humoral immune response (B cell response) resulting in the production of antibodies against the tumor-associated antigen. Furthermore, antigen presenting cells (APC) such as dendritic cells (DCs) can be loaded with MHC class I-presented peptides directly or by transfection with nucleic acids encoding tumor antigens or tumor antigen peptides in vitro and administered to a patient.

According to the present invention, a tumor-associated antigen preferably comprises any antigen which is characteristic for tumors or cancers as well as for tumor or cancer cells with respect to type and/or expression level. In one embodiment, the term "tumor-associated antigen" relates to proteins that are under normal conditions, i.e., in a healthy individual, specifically expressed in a limited number of organs and/or tissues or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2 or 1. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in an individual, e.g., a patient suffering from a cancer disease, is preferably a self-protein in said individual. In preferred embodiments, the tumor-associated antigen in the context of the present invention is expressed under normal conditions specifically in a tissue or organ that is non-essential, i.e., tissues or organs which when damaged by the immune system do not lead to death of the individual, or in organs or structures of the body which are not or only hardly accessible by the immune system. In one embodiment, the amino acid sequence of the tumor-associated antigen is identical between the tumor-associated antigen which is expressed in normal tissues and the tumor-associated antigen which is expressed in cancer tissues. Preferably, a tumor-associated antigen is presented in the context of MHC molecules by a cancer cell in which it is expressed.

Examples for differentiation antigens which ideally fulfill the criteria for tumor-associated antigens as contemplated by the present invention as target structures in tumor immunotherapy, in particular, in tumor vaccination are the cell surface proteins of the claudin family, such as CLDN6 and CLDN18.2. These differentiation antigens are expressed in tumors of various origins, and are particularly suited as target structures in connection with antibody-mediated cancer immunotherapy due to their selective expression (no expression in a toxicity relevant normal tissue) and localization to the plasma membrane.

Particular examples for antigens that may be useful in the present invention are those explicitly specified herein including p53 and WT-1.

The RNA or pharmaceutical compositions according to the present invention are generally applied in "pharmaceutically acceptable amounts" and in "pharmaceutically acceptable preparations". The term "pharmaceutically acceptable" refers to the non-toxicity of a material which does not interact with the action of the active agent(s) of the pharmaceutical composition.

A "therapeutically effective amount" relates to an amount which—alone or in combination with further dosages—results in a desired reaction or a desired effect. In the case of the therapy of a particular disease or a particular condition, the desired reaction relates to the inhibition of the progress of the disease. This comprises the deceleration of the progress of the disease, in particular a disruption of the progression of the disease. The desired reaction for a therapy of a disease or a condition may also be the retardation of the occurrence or the inhibition of the occurrence of the disease or the condition. An effective amount of the composition according to the present invention is dependent on the condition or disease, the severity of the disease, the individual parameters of the patient, including age, physiological condition, height and weight, the duration of the treatment, the type of an optionally accompanying therapy, the specific administration route, and similar factors. In case the reaction of a patient is insufficient with an initial dosage, higher dosages (or higher effective dosages which may be achieved by a more localized administration route) may be applied. In general, for a treatment or for an induction or increase of an immune reaction in a human preferably dosages of the RNA in the range of 1 ng to 700 µg, 1 ng to 500 µg, 1 ng to 300 µg, 1 ng to 200 µg, or 1 ng to 100 µg are formulated and administered.

According to the present invention, the administration of an RNA (such as mRNA) is either achieved as naked nucleic acid or in combination with one or more pharmaceutically acceptable excipients. Preferably, administration of nucleic acids is in the form of naked nucleic acids. Preferably, the RNA is administered in combination with stabilizing substances such as RNase inhibitors. The present invention also envisions the repeated introduction of nucleic acids into cells to allow sustained expression for extended time periods. However, due to the presence of the 5'-cap structure of the present invention and optionally other stabilizing modifications, the RNAs of the present invention preferably exhibit the advantage that they can be administered less frequently than RNAs not containing the 5'-cap structure of the present invention. Thus, using the RNAs of the present invention preferably provides the benefit to the patient that, for example with respect to the protein replacement therapy, less administrations (such as injections) of RNA (or pharmaceutical compositions) of the invention are required to achieve the desired effect (e.g., an expression of the desired peptide or protein in an amount sufficient to maintain the functions of the patient (e.g., to maintain the homeostasis of the patient)). Thus, in one embodiment the RNA of the invention (such as the RNA composition or pharmaceutical composition of the invention) is administered to a patient (e.g., by injection, such as intraperitoneal, intramuscular, or intradermal injection) at most once per day (i.e., the time period between two administrations is at least 24 h, such as at least 30 h, at least 36 h, or at least 42), preferably at most once per two days (i.e., the time period between two administrations is at least 48 h, such as at least 54 h, at least 60, or at least 66 h), preferably at most once per three days (i.e., the time period between two administrations is at least 72 h, such as at least 78 h, at least 84 h, or at least 90 h) or at most once per four days (i.e., the time period between two administrations is at least 96 h, such as at least 102 h, at least 108 h, or at least 114 h). Accordingly, the present invention is particularly beneficial for chronic patients and/or long-term patients, e.g., patients who are treated over an extended period of time, e.g., who receive the RNA of the invention (such as the RNA composition or pharmaceutical composition of the invention) over an extended period of time, wherein the extended period of time preferably is at least 1 week, such as at least 2 weeks, at least 3 weeks, at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 2 weeks, up to 3 weeks, up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the patient. Thus, in one embodiment the RNA of the invention (such as the RNA composition or pharmaceutical composition of the invention) is administered to a chronic patient or long-term patient (e.g., by injection, such as intraperitoneal, intramuscular, or intradermal injection) at most once per day (i.e., the time period between two administrations is at least 24 h, such as at least 30 h, at least 36 h, or at least 42), preferably at most once per two days (i.e., the time period between two administrations is at least 48 h, such as at least 54 h, at least 60, or at least 66 h), preferably at most once per three days (i.e., the time period between two administrations is at least 72 h, such as at least 78 h, at least 84 h, or at least 90 h) or at most once per four days (i.e., the time period between two administrations is at least 96 h, such as at least 102 h, at least 108 h, or at least 114 h) for an extended time period, in particular, at least 1 week, such as at least 2 weeks, at least 3 weeks, at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 2 weeks, up to 3 weeks, up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the chronic or long-term patient.

Cells can be transfected with any excipients (in particular carriers) with which RNA can be associated, e.g., by forming complexes with the RNA or forming vesicles in which the RNA is enclosed or encapsulated, resulting in increased stability of the RNA compared to naked RNA. Excipients (in particular carriers) useful according to the invention include, for example, lipid-containing carriers such as cationic lipids, liposomes, in particular cationic liposomes, and micelles, and nanoparticles. Cationic lipids may form complexes with negatively charged nucleic acids. Any cationic lipid may be used according to the invention. Furthermore, cells can be taken from an individual, the cells can be transfected with RNA or a pharmaceutical composition of the invention, and the transfected cells can be inserted into the individual.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins or fragments thereof which are specific for a particular cell type, antibodies against proteins which are internalized, proteins which target an intracellular location, etc.

In certain embodiments of the present disclosure, the capped RNA described herein may be present in RNA lipoplex particles. The RNA lipoplex particles and compositions comprising RNA lipoplex particles described herein are useful for delivery of the capped RNA described herein to a target tissue after parenteral administration, in particular after intravenous administration. The RNA lipoplex particles may be prepared using liposomes that may be obtained by injecting a solution of the lipids in ethanol into water or a suitable aqueous phase. In one embodiment, the aqueous phase has an acidic pH. In one embodiment, the aqueous phase comprises acetic acid, e.g., in an amount of about 5 mM. In one embodiment, the liposomes and RNA lipoplex particles comprise at least one cationic lipid and at least one additional lipid. In one embodiment, the at least one cationic lipid comprises 1,2-di-O-octadecenyl-3-trimethylammonium propane (DOTMA) and/or 1,2-dioleoyl-3-trimethylammonium-propane (DOTAP). In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC). In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). Liposomes may be used for preparing RNA lipoplex particles by mixing the liposomes with RNA.

Specific spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

The term "excipient" when used herein is intended to indicate all substances in a pharmaceutical composition which are not active agents (e.g., which are therapeutically inactive ingredients that do not exhibit any therapeutic effect in the amount/concentration used), such as, e.g., salts, carriers, binders, lubricants, thickeners, surface active agents, dispersing agents, preservatives, emulsifiers, buffering agents, wetting agents, flavoring agents, colorants, stabilizing agents (such as RNase inhibitors) or antioxidants all of which are preferably pharmaceutically acceptable.

"Pharmaceutically acceptable salts" comprise, for example, acid addition salts which may, for example, be formed by using a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, suitable pharmaceutically acceptable salts may include alkali metal salts (e.g., sodium or potassium salts); alkaline earth metal salts (e.g., calcium or magnesium salts); ammonium ($NH_4^+$); and salts formed with suitable organic ligands (e.g., quaternary ammonium and amine cations formed using counteranions such as halide, hydroxide, carboxylate, sulfate, phosphate, nitrate, alkyl sulfonate and aryl sulfonate). Illustrative examples of pharmaceutically acceptable salts include, but are not limited to, acetate, adipate, alginate, arginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, galactate, galacturonate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isobutyrate, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, phthalate, picrate, pivalate, polygalacturonate, propionate, salicylate, stearate, sulfate, suberate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)). Salts which are not pharmaceutically acceptable may be used for preparing pharmaceutically acceptable salts and are included in the invention.

The compositions according to the present invention may comprise a pharmaceutically acceptable carrier. As used herein, "pharmaceutically acceptable carrier" includes any and all solvents, dispersion media, coatings, isotonic and absorption delaying agents, and the like that are physiologically compatible. The "pharmaceutically acceptable carrier" may be in the form of a solid, semisolid, liquid, or combinations thereof.

Pharmaceutically acceptable carriers include sterile aqueous solutions or dispersions, sterile non-aqueous solutions or dispersions and sterile powders for the extemporaneous preparation of sterile injectable solutions or dispersions. The use of such media and agents for pharmaceutically active agents is known in the art. Except insofar as any conventional media or agent is incompatible with the active agent, use thereof in the pharmaceutical compositions of the invention is contemplated. Exemplary pharmaceutically acceptable carriers for an injectable formulation include water, an isotonic buffered saline solution (e.g., Ringer or Ringer lactate), ethanol, polyols (e.g., glycerol), polyalkylene glycols (e.g., propylene glycol and liquid polyethylene glycol), hydrogenated naphthalenes, and, in particular, biocompatible lactide polymers (e.g., lactide/glycolide copolymers or polyoxyethylene/polyoxy-propylene copolymers).

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Suitable buffering agents for use in the pharmaceutical compositions of the invention include acetic acid in a salt, citric acid in a salt, boric acid in a salt and phosphoric acid in a salt.

Suitable preservatives for use in the pharmaceutical compositions of the invention include various antibacterial and antifungal agents, such as benzalkonium chloride, chlorobutanol, paraben, sorbic acid, and thimerosal. Prevention of the presence of microorganisms may also be ensured by sterilization procedures (e.g., sterilization filtration, in particular sterilization microfiltration).

The pharmaceutical composition of the invention may be administered to an individual by any route, preferably parenterally. The expressions "parenteral administration" and "administered parenterally" as used herein mean modes of administration other than enteral administration ("enteral administration" and "administered enterally" as used herein mean that the drug administered is taken up by the stomach and/or the intestine). Parenteral administration is usually by injection and/or infusion and includes, without limitation, intravenous, intramuscular, intraarterial, intrathecal, intracapsular, intraosseous, intraorbital, intracardiac, intranodal, intradermal, intraperitoneal, transtracheal, subcutaneous, subcuticular, intraarticular, subcapsular, intracerebral, intracerebroventricular, subarachnoid, intraspinal, epidural intrasternal, and topical administration. For applications other than immunotherapy (e.g., for protein replacement therapy, genome engineering therapy, or genetic reprogramming therapy), it is preferred that the pharmaceutical composition of the invention is administered intraperitoneally, intramuscularly, or intradermally. For immunotherapeutical applications, it is preferred that the pharmaceutical composition of the invention is administered intravenously, intraperitoneally, intramuscularly, subcutaneously, intralymphaticly, intradermally or intranodally, more preferably intradermally or intranodally, e.g., by intranodal injection.

The pharmaceutical composition of the present invention can be administered by a variety of methods known in the art. As will be appreciated by the skilled artisan, the route and/or mode of administration will vary depending upon the desired results.

The active agents (i.e., the RNA of the invention and optionally one or more additional/supplementary active compounds) can be prepared with carriers that will protect the compounds against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer the active agent (i.e., the RNA of the invention and optionally one or more additional/supplementary active compounds) by certain routes of administration, it may be necessary to coat the active agent with, or co-administer the compound with, a material to prevent its inactivation and/or to increase the effectiveness of the active agent (in particular the RNA of the invention) to be translated. For example, the active agent may be administered to an individual in an appropriate carrier, for example, lipid-containing carriers (in particular cationic lipids), liposomes (such as water-in-oil-in-water CGF emulsions as well as conventional liposomes (Strejan et al., J. Neuroimmunol. 7: 27 (1984)), in particular cationic liposomes), micelles, nanoparticles in which the RNA is enclosed or encapsulated, or a diluent. Pharmaceutically acceptable diluents include saline and aqueous buffered solutions.

Pharmaceutical compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), suitable mixtures thereof, vegetable oils, such as olive oil, and injectable organic esters, such as ethyl oleate. The proper fluidity can be maintained, for example, by the use of a coating material such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the pharmaceutical composition. Prolonged absorption of the injectable compositions can be brought about by including in the composition an agent that delays absorption, for example, monostearate salts and gelatin.

Generally, dispersions are prepared by incorporating the active agent into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active agent plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate pharmaceutical compositions in unit dosage form for ease of administration and uniformity of dosage. Unit dosage form as used herein refers to physically discrete units suited as unitary dosages for the individuals to be treated; each unit contains a predetermined quantity of active agent calculated to produce the desired therapeutic effect in association with the required pharmaceutical carrier. The specification for the unit dosage forms of the invention are dictated by and directly dependent on (a) the unique characteristics of the active agent and the particular therapeutic effect to be achieved, and (b) the limitations inherent in the art of compounding such an active agent for the treatment of sensitivity in individuals. The amount of active agent (in particular, the amount of RNA) which can be combined with a carrier material to produce a pharmaceutical composition (such as a single dosage form) will vary depending upon the individual being treated, and the particular mode of administration. The amount of active agent which can be combined with a carrier material to produce a single dosage form will generally be that amount of the composition which produces a therapeutic effect.

Generally, out of 100% (for the pharmaceutical formulations/compositions), the amount of active agent (in particular, the amount of the RNA of the present invention, optionally together with one or more additional/supplementary active compounds, if present in the pharmaceutical formulations/compositions) will range from about 0.01% to about 99%, preferably from about 0.1% to about 70%, most preferably from about 1% to about 30%, wherein the reminder is preferably composed of the one or more pharmaceutically acceptable excipients.

The amount of active agent, e.g., an RNA of the invention, in a unit dosage form and/or when administered to an individual or used in therapy, may range from about 0.001 mg to about 1000 mg (for example, from about 0.01 mg to about 500 mg, from about 0.1 mg to about 100 mg such as from about 1 mg to about 50 mg) per unit, administration or therapy. In certain embodiments, a suitable amount of such active agent may be calculated using the mass or body surface area of the individual, including amounts of between about 0.1 mg/kg and 10 mg/kg (such as between about 0.2 mg/kg and 5 mg/kg), or between about 0.1 mg/m$^2$ and about 400 mg/m$^2$ (such as between about 0.3 mg/m$^2$ and about 350 mg/m$^2$ or between about 1 mg/m$^2$ and about 200 mg/m$^2$).

Regardless of the route of administration selected, the active agents (i.e., the RNA and optionally one or more additional/supplementary active compounds), which may be used in a suitable hydrated form, and/or the pharmaceutical compositions of the present invention, are formulated into pharmaceutically acceptable dosage forms by conventional methods known to those of skill in the art (cf., e.g., Remington, "The Science and Practice of Pharmacy" edited by Allen, Loyd V., Jr., 22$^{nd}$ edition, Pharmaceutical Sciences, September 2012; Ansel et al., "Pharmaceutical Dosage Forms and Drug Delivery Systems", 7$^{th}$ edition, Lippincott Williams & Wilkins Publishers, 1999.).

Actual dosage levels of the active agents in the pharmaceutical compositions of the present invention may be varied so as to obtain an amount of the active agent which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular active agent being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start with doses of the active agents employed in the pharmaceutical composition at levels lower than that required in order to achieve the desired therapeutic effect and gradually increase the dosage until the desired effect is achieved. In general, a suitable daily dose of a pharmaceutical composition of the invention will be that amount of the active agent which is the lowest dose effective to produce a therapeutic effect. Such an effective dose will generally depend upon the factors described above. It is preferred that administration be parenteral, such as intravenous, intramuscular, intraperitoneal, or subcutaneous, preferably administered proximal to the site of the target. The administration can also be intra-tumoral. If desired, the effective daily dose of a pharmaceutical composition may be administered as two, three, four, five, six or more sub-doses administered separately at appropriate intervals throughout the day, optionally, in unit dosage forms. While it is possible for an active agent (in particular RNA) of the present invention to be administered alone, it is preferable to administer the active agent as a pharmaceutical formulation/composition.

In one embodiment, the RNA or pharmaceutical compositions of the invention may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months.

The pharmaceutical composition of the invention can be formulated for parenteral administration by injection, for example, by bolus injection or continuous infusion. Formulations for injection can be presented in units dosage form (e.g., in phial, in multi-dose container), and with an added preservative. The pharmaceutical composition of the invention can take such forms as suspensions, solutions or emulsions in oily or aqueous vehicles, and can contain formulatory agents such as suspending, stabilizing, or dispersing agents. Alternatively, the agent can be in powder form for constitution with a suitable vehicle (e.g., sterile pyrogen-free water) before use. Typically, pharmaceutical compositions for intravenous administration are solutions in sterile isotonic aqueous buffer. Where necessary, the pharmaceutical composition can also include a solubilizing agent and a local anesthetic such as lignocaine to ease pain at the site of the injection. Generally, the ingredients are supplied either separately or mixed together in unit dosage form, for example, as a dry lyophilised powder or water free concentrate in a hermetically sealed container such as an ampoule or sachette indicating the quantity of active agent. Where the pharmaceutical composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

Pharmaceutical compositions can be administered with medical devices known in the art. For example, in a preferred embodiment, a pharmaceutical composition of the invention can be administered with a needleless hypodermic injection device, such as the devices disclosed in U.S. Pat. Nos. 5,399,163; 5,383,851; 5,312,335; 5,064,413; 4,941,880; 4,790,824; or U.S. Pat. No. 4,596,556. Examples of well-known implants and modules useful in the present invention include those described in: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, RNA or pharmaceutical compositions of the invention can be formulated to ensure proper distribution in vivo. For example, the blood-brain barrier (BBB) excludes many highly hydrophilic compounds. To ensure that the RNA or pharmaceutical compositions of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment of the invention, the RNA of the invention is formulated in liposomes. In a more preferred embodiment, the liposomes include a targeting moiety. In a most preferred embodiment, the RNA in the liposomes is delivered by bolus injection to a site proximal to the desired area. Such liposome-based composition should be fluid to the extent that easy syringability exists, should be stable under the conditions of manufacture and storage and should be preserved against the contaminating action of microorganisms such as bacteria and fungi.

A "therapeutically effective amount" for treatment can be measured by objective responses which can either be complete or partial. A complete response (CR) is defined as no clinical, radiological or other evidence of a condition, disorder or disease. A partial response (PR) results from a reduction in disease of greater than 50%. Median time to progression is a measure that characterizes the durability of the objective response.

A "therapeutically effective amount" for treatment can also be measured by its ability to stabilize the progression of a condition, disorder or disease, e.g., by using appropriate animal model systems and/or in vitro assays known to the skilled person. A therapeutically effective amount of an active agent (in particular RNA of the invention) refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. Thus, a therapeutically effective amount of an active agent can cure, heal, alleviate, relieve, alter, remedy, ameliorate, improve or affect the condition, disorder or disease or the symptoms of the condition, disorder or disease or the predisposition toward the condition, disorder or disease in an individual. One of ordinary skill in the art would be able to determine such amounts based on such factors as the disease, disorder or condition to be treated, the severity of the disease, disorder or condition, the parameters of the individual to be treated (including age, physiological condition, size and weight), the duration of treatment, the type of an accompanying therapy (if present), the specific route of administration and similar factors.

Accordingly, the doses administered of the active agents described herein may depend on various of such parameters. In the case that a reaction in an individual/patient is insufficient with an initial dose, higher doses (or effectively higher doses achieved by a different, more localized route of administration) may be used.

The pharmaceutical composition of the present invention may take the form of a vaccine preparation comprising the RNA of the invention encoding at least one antigen such as an antigen as discussed above or an fragment thereof (in particular an immunogenic fragment thereof).

The pharmaceutical composition of the invention can also, if desired, be presented in a pack, kit or dispenser device which can contain one or more unit dosage forms containing the active agent (i.e., the RNA and optionally one or more additional/supplementary active compounds). The pack can for example comprise metal or plastic foil, such as blister pack. The pack, kit or dispenser device can be accompanied with instruction for administration.

The one or more additional/supplementary active compounds may comprise an immunomodulating agent such as anti-CTL-A4 or anti-PD1 or anti-PDL1 or anti-regulatory T-cell reagents such as an anti-CD25 antibody or cyclophosphamide.

The pharmaceutical compositions of the invention may be administered together with supplementing immunity-enhancing substances such as one or more adjuvants and may comprise one or more immunity-enhancing substances to further increase its effectiveness, preferably to achieve a synergistic effect of immunostimulation.

The term "adjuvant" relates to compounds which when administered in combination with an antigen, an antigen peptide, or a nucleic acid (such as RNA, preferably mRNA) encoding said antigen or antigen peptide to an individual prolongs or enhances or accelerates the immune response. In the context of the present invention, RNA (preferably mRNA) may be administered with any adjuvants. It is assumed that adjuvants exert their biological activity by one or more mechanisms, including an increase of the surface of the antigen, a prolongation of the retention of the antigen in the body, a retardation of the antigen release, targeting of the antigen to macrophages, increase of the uptake of the antigen, enhancement of antigen processing, stimulation of cytokine release, stimulation and activation of immune cells such as B-cells, macrophages, dendritic cells, T-cells and unspecific activation of immune cells. For example, compounds which allow the maturation of the DCs, e.g. lipopolysaccharides or CD40 ligand, form a class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides (Krieg et al., 1995, Nature 374: 546-549) can optionally also be used in this context. Further types of adjuvants include oil emulsions (e.g., Freund's adjuvants), mineral compounds (such as alum), bacterial products (such as *Bordetella pertussis* toxin), liposomes, immune-stimulating complexes, cytokines (e.g., monokines, lymphokines, interleukins or chemokines, such as IL-1, IL-2, IL-3, IL-4, IL-5, IL-6, IL-7, IL-8, IL-9, IL-10, IL-12, IFN-α, IFN-γ, GM-CSF, LT-α, or growth factors, e.g. hGH), lipopeptides (e.g., Pam3Cys). In case the RNA (preferably mRNA) of the invention in one embodiment may encode an immunostimulating agent and said immunostimulating agent encoded by said RNA is to act as the primary immunostimulant, however, only a relatively small amount of CpG DNA is necessary (compared with immunostimulation with only CpG DNA). Examples for adjuvants are monophosphoryl-lipid-A (MPL SmithKline Beecham). Saponins such as QS21 (SmithKline Beecham), DQS21 (SmithKline Beecham; WO 96/33739), QS7, QS17, QS18, and QS-L1 (So et al., 1997, Mol. Cells 7: 178-186), incomplete Freund's adjuvants, complete Freund's adjuvants, vitamin E, montanid, alum, CpG oligonucleotides, and various water-in-oil emulsions which are prepared from biologically degradable oils such as squalene and/or tocopherol. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFN-α, IFN-γ, GM-CSF, LT-α, growth factors, e.g. hGH or lipopeptides, such as Pam3Cys, all of which are suitable for use as adjuvants in the pharmaceutical compositions of the present invention or when RNA (in particular mRNA) of the present invention is used in therapy.

Treatment may be provided at home, the doctor's office, a clinic, a hospital's outpatient department, or a hospital. Treatment generally begins under medical supervision so that medical personnel can observe the treatment's effects closely and make any adjustments that are needed. The duration of the treatment depends on the age and condition of the patient, as well as how the patient responds to the treatment.

A person having a greater risk of developing a condition, disorder or disease may receive prophylactic treatment to inhibit or delay symptoms of the condition, disorder or disease.

The term "treatment" is known to the person of ordinary skill, and includes the application or administration of an active agent (e.g., a pharmaceutical composition containing said active agent) as described herein (e.g., RNA such as mRNA or a pharmaceutical composition comprising RNA such as mRNA) or procedure to an individual/patient or application or administration of an active agent (e.g., a pharmaceutical composition containing said active agent) as described herein (e.g., RNA such as mRNA or a pharmaceutical composition comprising RNA such as mRNA) or procedure to a cell, cell culture, cell line, sample, tissue or organ isolated from an individual, who has a condition, disorder or disease, a symptom of the condition, disorder or disease or a predisposition toward a condition, disorder or disease, with the purpose to cure, heal, alleviate, relieve, alter, remedy, ameliorate, improve, affect or prevent the condition, disorder or disease, the symptoms of the condition, disorder or disease or the predisposition toward the condition, disorder or disease (e.g., to prevent or eliminate a disease, including reducing the size of a tumor or the number of tumors in an individual; arrest or slow a disease in an individual; inhibit or slow the development of a new disease in an individual; decrease the frequency or severity of symptoms and/or recurrences in an individual who currently has or who previously has had a disease; and/or prolong, i.e. increase the lifespan of the individual). In particular, the term "treatment of a disease" includes curing, shortening the duration, ameliorating, preventing, slowing down or inhibiting progression or worsening, or preventing or delaying the onset of a disease or the symptoms thereof. Hence, the term "treatment" can include prophylactic treatment of a condition, disorder or disease, or the symptom of a condition, disorder or disease. An active agent, when used in treatment, includes the RNA of the invention as well as the one or more additional/supplementary active compounds described herein and includes, but is not limited to, other therapeutically active compounds that may be small molecules, peptides, peptidomimetics, polypeptides/proteins, antibodies, other polynucleotides such as DNA or dsRNA, cells, viruses, ribozymes, and antisense oligonucleotides.

In a preferred embodiment, the pharmaceutical composition of the invention is substantially free of dsRNA, preferably substantially free of dsRNA and DNA.

The term "substantially free of dsRNA" as used herein in conjunction with an RNA preparation comprising RNA modified with a 5'-cap compound of the present application, in particular a pharmaceutical composition, especially a pharmaceutical composition comprising an RNA modified with a 5'-cap compound of the present application, means that the amount of dsRNA in the RNA preparation or pharmaceutical composition is such that said RNA preparation or pharmaceutical composition when administered to an individual does not substantially induce an undesired response (such as an undesired induction of inflammatory cytokines (e.g., IFN-α) and/or an undesired activation of effector enzyme leading to an inhibition of protein synthesis from the RNA of the invention) in said individual. Preferably, the terms "substantially free of dsRNA" and "does not substantially induce an undesired response" mean that, when administered to an individual, said RNA preparation or pharmaceutical composition results in the translation of the RNA into the peptide or protein for at least 10 h (e.g., at least 12 h, at least 14 h, at least 16 h, at least 18 h, at least 20 h, at least 22 h, at least 24 h, at least 30 h, at least 36 h, at least 42 h, at least 48 h, at least 54 h, at least 60 h, at least 66 h, at least 72 h, at least 78 h, at least 84 h, at least 90 h, or at least 96 h) after administration. For example, the content of dsRNA in the RNA preparation or pharmaceutical composition may be at most 5% by weight (preferably at most 4% by weight, at most 3% by weight, at most 2% by weight, at most 1% by weight, at most 0.5% by weight, at most 0.1% by weight, at most 0.05% by weight, at most 0.01% by weight, at most 0.005% by weight, at most 0.001% by weight), based on the total weight of said RNA preparation or pharmaceutical composition.

The term "substantially free of DNA" as used herein in conjunction with an RNA preparation comprising RNA modified with a 5'-cap compound of the present application, in particular a pharmaceutical composition, especially a pharmaceutical composition comprising an RNA modified with a 5'-cap compound of the present application, means that the amount of DNA in the RNA preparation or pharmaceutical composition may be at most 5% by weight (preferably at most 4% by weight, at most 3% by weight, at most 2% by weight, at most 1% by weight, at most 0.5% by weight, at most 0.1% by weight, at most 0.05% by weight, at most 0.01% by weight, at most 0.005% by weight, at most 0.001% by weight), based on the total weight of said RNA preparation or pharmaceutical composition.

The term "substantially free of dsRNA and DNA" as used herein in conjunction with an RNA preparation comprising RNA modified with a 5'-cap compound of the present application, in particular a pharmaceutical composition, especially a pharmaceutical composition comprising an RNA modified with a 5'-cap compound of the present application, means that said RNA preparation or pharmaceutical composition is substantially free of dsRNA as specified above (e.g., the translation lasts at least 10 h after administration and/or the dsRNA content is at most 5% by weight) and is substantially free of DNA as specified above (e.g., the DNA content is at most 5% by weight).

In one embodiment, the pharmaceutical composition of the invention is a vaccine composition.

The vaccine composition of the present invention may be regarded as a pharmaceutical composition of the present invention for a particular use (i.e., vaccination). Thus, one or more of the features and embodiments described above in connection with the pharmaceutical composition of the present invention (e.g., administration route; presence of other components (such as one or more pharmaceutically acceptable carriers, excipients, and/or diluents and/or adjuvants and/or one or more additional/supplementary active compounds); amount of active agent(s); pharmaceutically acceptable salts; etc.) may also apply to the vaccine composition of the present invention.

In a preferred embodiment, said vaccine composition further comprises one or more pharmaceutically acceptable carriers, excipients, and/or diluents. Said vaccine composition may further comprise compounds or substances which are capable of enhancing and/or supporting an immune reaction in an individual. For example, the vaccine composition of the present invention may further comprise an adjuvant as described above or cytokines, for example, interleukin-12 (IL-12), granulocyte-macrophage colony-stimulating factor (GM-CSF), or interleukin-18 (IL-18). Furthermore, the vaccine composition according to the present invention may further comprise RNA stabilizing substances such as RNase inhibitors, pharmaceutically acceptable salts or buffers, preservatives (such as benzalkonium chloride, chlorbutanol, parabene, or Thimerosal), wetting agents, emulsifying agents, and/or additional drugs or active agents.

In a particularly preferred embodiment, the RNA is present in the vaccine composition according to the present invention in the form of naked RNA.

It is particularly preferred that the vaccine composition of the present invention is formulated for parenteral administration, for example, for intravenous, intraperitoneal, intramuscular, subcutaneous, intralymphatic, intradermal or intranodal administration, more preferably for intradermal or intranodal administration, such as intranodal injection. The vaccine composition of the invention is most preferably formulated for injection into lymph nodes, preferably inguinal lymph nodes, for injection into lymphatic vessels and/or the spleen.

Preferably, the vaccine composition is in the form of an aqueous or non-aqueous solution which is isotonic with the blood of the recipient, i.e., the individual to be vaccinated. For example, Ringer solution, isotonic sodium chloride solution, or phosphate buffered saline (PBS) may be used. In particular, the vaccine composition is preferably sterile and comprises the above specified RNA in a therapeutically effective amount.

In a preferred embodiment, the vaccine composition is substantially free of dsRNA, preferably substantially free of dsRNA and DNA.

Cells

In a further aspect, the present invention provides a cell comprising an RNA which is modified with a 5'-cap compound of the present application, wherein the RNA preferably comprises a nucleotide sequence encoding a peptide or protein. In this preferred embodiment of the cell, where the RNA of the invention comprises a nucleotide sequence encoding a peptide or protein, the cell can be used for producing said peptide or protein, e.g., in the corresponding method for producing a peptide or protein described herein, or for expressing said peptide or protein in an individual by administering said cell to the individual, e.g., in the corresponding method for expressing a peptide or protein described herein.

In a preferred embodiment, the cell is an antigen presenting cell, such as an immature antigen presenting cell, and may be selected from the group consisting of macrophages, monocytes, B-cells, and dendritic cells.

In a particularly preferred embodiment, the cell according to the present invention is formulated in a pharmaceutical composition as described above, said pharmaceutical composition preferably being suitable to express a peptide or protein, such as a pharmaceutically active peptide or protein. In an alternative embodiment, the cell according to the present invention is formulated in a pharmaceutical composition as described above, said pharmaceutical composition preferably being suitable to elicit an immune response when administered to an individual, wherein the immune response is preferably directed against the protein or peptide encoded by the RNA or an antigen and/or immunogen comprised by the protein or peptide encoded by the RNA present in the immature antigen presenting cell of the present invention. Thus, the present invention provides a pharmaceutical composition comprising an immature antigen presenting cell according to the third aspect of the present invention.

Methods and Uses

In one aspect, the present invention provides a method for providing an RNA with a 5'-cap structure, said method comprising performing a transcription reaction using a template nucleic acid in the presence of a 5'-cap compound of the first aspect. In one embodiment, the template nucleic acid is DNA. The transcription reaction may be performed in vivo or in vitro, but is preferably performed in vitro. In one embodiment, the transcription reaction is performed using an RNA polymerase selected from the group consisting of T3, T7 and SP6 RNA polymerases. The RNA may comprise a nucleotide sequence encoding a peptide or protein, wherein the peptide or protein is preferably a pharmaceutically active peptide or protein as described herein. In one embodiment, the method is performed in the absence of a 2'-O-ribose methyltransferase. In an alternative embodiment, the method is performed in the presence of a 2'-O-ribose methyltransferase.

In another aspect, the present invention provides a method of increasing the stability of an RNA in cells and/or for increasing the expression of an RNA in cells, said method comprising providing said RNA with the structure according to formula (I) as defined in the first aspect; and transferring said RNA modified with the structure according to formula (I) into the cells. Preferably, said cells are antigen presenting cells, such as immature antigen presenting cells, preferably selected from the group consisting of monocytes, macrophages, glia cells, B-cells, and dendritic cells. In order to assess the stability of an RNA in an immature antigen presenting cell, the skilled person may detect the presence of the studied RNA or quantify the amount of RNA within a cell after certain time points after introduction of said RNA, for example, by using real time RT-PCR. The expression of an RNA in cells may be determined using an RNA encoding a marker protein such as luciferase or green fluorescent protein, preferably d2EGFP but may be any other marker protein known to the skilled person, and determining the expression of said marker protein at certain time points after introduction of the RNA. In one embodiment, the step of providing said RNA with the structure according to formula (I) is performed in the absence of a 2'-O-ribose methyltransferase. In an alternative embodiment, the method is performed in the presence of a 2'-O-ribose methyltransferase.

In a further aspect, the present invention provides a method for producing a peptide or protein of interest comprising the step of using the RNA, RNA composition or cell of the invention, wherein in each case the RNA comprises a nucleotide sequence encoding the peptide or protein. In one embodiment, the peptide or protein is a pharmaceutically active protein, preferably selected from the group consisting of cytokines, such as erythropoietin; adhesion molecules, such as an integrin; immunoglobulins; immunologically active compounds, e.g., antigens, such as tumor-associated antigens, pathogen-associated antigens (e.g., one or more (e.g., 1, 2, 3, 4, 5, 6, 7, 8, 9, or 10) antigens of a virus, such as one or more (e.g., 1, 2, 3, 4, 5, 6, 7, 8, 9, or 10) antigens of influenza virus (A, B, or C), CMV, or RSV), allergens, or autoantigens; hormones, such as vasopressin, insulin or growth hormone; growth factors, such as VEGFA; enzymes, such as herpes simplex virus type 1 thymidine kinase (HSV1-TK), hexosaminidase, phenylalanine hydroxylase, pseudocholinesterase, pancreatic enzymes, or lactase; receptors, such as growth factor receptors; protease inhibitors, such as alpha 1-antitrypsin; apoptosis regulators, such as BAX; transcription factors, such as FOXP3; tumor suppressor proteins, such as p53; structural proteins, such as surfactant proteins; reprogramming factors, such as OCT4, SOX2, c-MYC, KLF4, LIN28, or NANOG; genomic engineering proteins, such as clustered regularly spaced short palindromic repeat-CRISPR-associated protein 9 (CRISPR-Cas9); and blood proteins, such as fibrinogen. In the embodiment of the method using the RNA or RNA composition, the method may comprise the step of transferring said RNA or RNA composition into a cell. In this respect, any technique which is suitable to transfer RNA into cells may be used. Preferably, the RNA is transfected into cells by standard techniques as described herein, e.g., calcium phosphate precipitation, DEAE transfection, electroporation, lipofection, or microinjection. The cell may be any cell which can be transfected with RNA and is preferably an antigen presenting cell, such as an immature antigen presenting cell, more preferably selected from the group consisting of macrophages, monocytes, B-cells, and dendritic cells. The method for producing a peptide or protein of interest may be performed in vivo or in vitro, but is preferably performed in vitro.

In a further aspect, the present invention provides a method for expressing a peptide or protein in an individual comprising the step of administering to said individual the RNA, RNA composition or cell of the invention, wherein in each case the RNA comprises a nucleotide sequence encoding a peptide or protein. In one embodiment, the peptide or protein is a pharmaceutically active protein, preferably selected from the group consisting of cytokines, such as erythropoietin; adhesion molecules, such as an integrin; immunoglobulins; immunologically active compounds, e.g., antigens, such as tumor-associated antigens, pathogen-associated antigens (e.g., one or more (e.g., 1, 2, 3, 4, 5, 6, 7, 8, 9, or 10) antigens of a virus, such as one or more (e.g., 1, 2, 3, 4, 5, 6, 7, 8, 9, or 10) antigens of influenza virus (A, B, or C), CMV, or RSV), allergens, or autoantigens; hormones, such as vasopressin, insulin or growth hormone; growth factors, such as VEGFA; enzymes, such as herpes simplex virus type 1 thymidine kinase (HSV1-TK), hexosaminidase, phenylalanine hydroxylase, pseudocholinesterase, pancreatic enzymes, or lactase; receptors, such as growth factor receptors; protease inhibitors, such as alpha 1-antitrypsin; apoptosis regulators, such as BAX; transcription factors, such as FOXP3; tumor suppressor proteins, such as p53; structural proteins, such as surfactant proteins; reprogramming factors, such as OCT4, SOX2, c-MYC, KLF4, LIN28, or NANOG; genomic engineering proteins, such as clustered regularly spaced short palindromic repeat-CRISPR-associated protein 9 (CRISPR-Cas9); and blood proteins, such as fibrinogen. The RNA, RNA composition or cell of the invention may be administered by any route, e.g., those described above with respect to pharmaceutical compositions of the invention.

In further aspects, the present invention provides (i) the RNA, RNA composition, or cell of the invention for use in therapy, in particular for use in a method of treating a disease or disorder in a subject, (ii) a method of treating a disease or disorder in a subject comprising the step of administering to said subject the RNA, RNA composition, or cell of the invention; and (iii) the use of the RNA, RNA composition, or cell of the invention for the preparation of a medicament for treating a disease or disorder in a subject, wherein in each of (i) to (iii) the RNA comprises a nucleotide sequence encoding a peptide or protein which preferably is a disease-associated peptide or protein. In one embodiment of these aspects (i) to (iii), the treatment of a disease or disorder is selected from the group consisting of protein replacement therapy, genome engineering, genetic reprogramming, and immunotherapy, as described herein. Preferably, the peptide or protein is a pharmaceutically active protein, more preferably selected from the group consisting of cytokines, such as erythropoietin; adhesion molecules, such as an integrin; immunoglobulins; immunologically active compounds, e.g., antigens, such as tumor-associated antigens, pathogen-associated antigens (e.g., one or more (e.g., 1, 2, 3, 4, 5, 6, 7, 8, 9, or 10) antigens of a virus, such as one or more (e.g., 1, 2, 3, 4, 5, 6, 7, 8, 9, or 10) antigens of influenza virus (A, B, or C), CMV, or RSV), allergens, or autoantigens; hormones, such as vasopressin, insulin or growth hormone; growth factors, such as VEGFA; enzymes, such as herpes simplex virus type 1 thymidine kinase (HSV1-TK), hexosaminidase, phenylalanine hydroxylase, pseudocholinesterase, pancreatic enzymes, or lactase; receptors, such as growth factor receptors; protease inhibitors, such as alpha 1-antitrypsin; apoptosis regulators, such as BAX; transcription factors, such as FOXP3; tumor suppressor proteins, such as p53; structural proteins, such as surfactant proteins; reprogramming factors, such as OCT4, SOX2, c-MYC, KLF4, LIN28, or NANOG; genomic engineering proteins, such as clustered regularly spaced short palindromic repeat-CRISPR-associated protein 9 (CRISPR-Cas9); and blood proteins, such as fibrinogen. In one embodiment, the disease or disorder is selected from the diseases and disorders disclosed herein, e.g., the illustrative diseases and disorders described herein with respect to protein replacement therapy, genome engineering therapy, genetic reprogramming therapy, and/or immunotherapy. The RNA, RNA composition or cell of the invention may be administered by any route and/or in any regimen or amount, e.g., by those routes and/or in those regimens and/or amounts described above with respect to pharmaceutical compositions of the invention. In one embodiment, the RNA, RNA composition or cell of the invention is administered to the subject (e.g., by injection, such as intraperitoneal, intramuscular, or intradermal injection) at most once per day, preferably at most once per two days, preferably at most once per three days or at most once per four days. In one embodiment, the RNA, RNA composition or cell of the invention is administered to a chronic patient or long-term patient (e.g., by injection, such as intraperitoneal, intramuscular, or intradermal injection) for an extended period of time, in particular at least 1 week, such as at least 2 weeks, at least 3 weeks, at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 2 weeks, up to 3 weeks, up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the patient. In one embodiment, the RNA of the invention (such as the RNA composition or pharmaceutical composition of the invention) is administered to a chronic patient or long-term patient (e.g., by injection, such as intraperitoneal, intramuscular, or intradermal injection) at most once per day (i.e., the time period between two administrations is at least 24 h, such as at least 30 h, at least 36 h, or at least 42), preferably at most once per two days (i.e., the time period between two administrations is at least 48 h, such as at least 54 h, at least 60, or at least 66 h), preferably at most once per three days (i.e., the time period between two administrations is at least 72 h, such as at least 78 h, at least 84 h, or at least 90 h) or at most once per four days (i.e., the time period between two administrations is at least 96 h, such as at least 102 h, at least 108 h, or at least 114 h) for an extended time period, i.e., at least 1 week, such as at least 2 weeks, at least 3 weeks, at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 2 weeks, up to 3 weeks, up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the patient.

In further aspects, the present invention provides the following:

(I) Provided is a method for eliciting an immune response in an individual comprising the step of administering to said individual the vaccine composition of the second aspect or the immature antigen presenting cell of the third aspect. Preferably, said immune response is specifically directed against the protein or peptide encoded by the RNA comprised by the vaccine composition or the immature antigen presenting cell of the present invention or is specifically directed against an antigen comprised by said protein or peptide. Said immune response may be therapeutic and/or protective. It is particularly preferred that said vaccine composition and said immature antigen presenting cells, preferably immature dendritic cells, are administered parenterally as specified above for the second aspect of the present invention, preferably by intranodal injection, preferably by injection into inguinal lymph nodes. In one embodiment the method is for eliciting an immune response against a virus, such as against influenza virus (A, B, or C), CMV, or RSV.

(II) Provided is a method of increasing a portion of MHC molecules which present an antigen of interest (e.g., an antigen of a virus, such as influenza virus (A, B, or C), CMV, or RSV) on the surface of an antigen presenting cell, said method comprising providing an RNA comprising a nucleotide sequence encoding a peptide or protein comprising said antigen of interest (e.g., an antigen of a virus, such as influenza virus (A, B, or C), CMV, or RSV) or an antigen peptide thereof, said RNA being modified with the structure according to formula (I) as defined in the first aspect; and transferring said RNA modified with the structure according to formula (I) into an immature antigen presenting cell. In one embodiment, the step of providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I), is performed in the absence of a 2'-O-ribose methyltransferase. In an alternative embodiment, said step is performed in the presence of a 2'-O-ribose methyltransferase. Without being bound to any theory, it is assumed that modifying an RNA with a 5'-cap compound of the present invention increases the stability and/or expression of said RNA, in particular within immature antigen presenting cells, for example, immature dendritic cells. This increased stability and/or expression leads to an accumulation of the protein or peptide encoded by said RNA. Said protein or peptide may comprise an antigen or antigen peptide. Thus, after processing of said protein antigens or antigen peptides may be loaded on MHC molecules on the surface of the antigen presenting cell. Alternatively, said protein or peptide may be itself an antigen or antigen peptide and may be loaded on MHC molecules without processing. It is assumed, that an RNA encoding a particular protein or peptide comprising an antigen or antigen peptide which has been modified with a 5'-cap compound of the present invention increases the portion/fraction of MHC molecules on the cell surface of an antigen presenting cell which present a peptide derived from the protein or peptide encoded by said RNA when compared to the same RNA having a conventional 5'-cap structure, preferably when compared to a reference RNA, such as the same RNA having an ARCA 5'-cap structure. Since the density of MHC molecules presenting a particular antigen on the surface of an antigen presenting cell is decisive for the intensity of the induced immune response specific for said particular antigen, it is assumed that increasing the stability of an antigen encoding RNA which has been introduced into antigen presenting cells leads to an increased immune response against said particular antigen.

(III) Provided is a method for stimulating and/or activating immune effector cells, said method comprising providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I) as defined in the first aspect; transferring said RNA modified with the structure according to formula (I) into immature antigen presenting cells; and contacting the antigen presenting cells with the immune effector cells. Preferably, said immune effector cells are antigen-specifically activated and/or stimulated. Preferably, by this method, the amount of antigen-specific effector cells, preferably T-cells, is increased. Preferably, the immature antigen presenting cells are immature dendritic cells. In one embodiment, the step of providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I), is performed in the absence of a 2'-O-ribose methyltransferase. In an alternative embodiment, said step is performed in the presence of a 2'-O-ribose methyltransferase. In a preferred embodiment, the immune effector cells are T-cells, preferably CD4+ and/or CD8 cells. In one embodiment, the step of transferring said RNA into immature antigen presenting cells is performed in vitro by any nucleic acid transfer method, e.g., a transfection method, known to the skilled person such as lipofection, electroporation, or microinjection as described above. In another embodiment, the step of transferring said RNA into immature antigen presenting cells is performed in vivo, for example, by administering the RNA to an individual, preferably by parenteral administration, preferably by intralymphatic administration, preferably by injection into lymph node(s), i.e., by intranodal injection, by injection into lymphatic vessels, or by injection into the spleen. Preferably, said administration is by intranodal injection of the RNA which is preferably taken up by immature dendritic cells in the lymph node(s). The administered RNA is preferably in the form of naked RNA. In one embodiment, the step of contacting the antigen presenting cells with the immune effector cells is performed in vitro, for example, in a tissue culture dish. In another embodiment, the step of contacting the antigen presenting cells with the immune effector cells is performed in vivo. In this embodiment, the step of transferring the RNA into immature antigen presenting cells may be performed in vitro or in vivo as described above. For contacting the antigen presenting cells into which the RNA has been transferred in vitro with immune effector cells in vivo, the antigen presenting cells are administered to an individual, preferably by parenteral administration, for example, by intravenous, intramuscular, subcutaneous, intranodal, intralymphatic, or intraperitoneal injection, preferably by injection into the lymphatic system such as by injection into lymphatic vessel(s), the spleen, and/or lymph node(s), preferably inguinal lymph node(s). In an embodiment, the method may further comprise the step of differentiating the immature antigen presenting cells into mature antigen presenting cells after transferring the RNA into the immature antigen presenting cells and before contacting the antigen presenting cells with the immune effector cells. The differentiation step may be performed in vitro or in vivo. For example, the RNA may be transferred into the immature antigen presenting cells, preferably into immature dendritic cells, the immature antigen presenting cells are differentiated in vitro, and the differentiated mature antigen presenting cells, preferably the mature dendritic cells, are contacted with immune effector cells in vitro or in vivo as described above, preferably in vivo. The immature antigen presenting cells into which the RNA is transferred in vitro may be isolated from an individual, for example a patient to be immunized, or they may be differentiated from hematopoietic stem cells.

A stimulation and/or activation of immune effector cells, in particular of T-cells, is typically associated with expansion, cytotoxic reactivity, and/or cytokine secretion of the immune effector cells. Thus, the skilled person may determine whether immune effector cells are stimulated and/or activated by simple in vitro tests, typically performed using T cells. Such T cells may be provided by transformed T cell lines such as T cell hybridomas or T cells which have been isolated from a mammal such as from a rodent, e.g., a mouse or a rat. Suitable T cell hybridomas are commercially available or may be generated by known methods. T cells may be isolated from a mammal by known methods (cf. Shimonkevitz et al., 1983, J. Exp. Med. 158: 303-316). A suitable experimental setting to test for T cell activation and/or stimulation is described below in steps (1) to (4). T cells express a suitable marker which may be tested and which indicates T cell activation or modulation of T cell activity. The murine T cell hybridoma DO11.10 may be used for this purpose, since said hybridoma expresses interleukin-2 (IL-2) upon activation. IL-2 concentrations may be determined to verify T cell activation/stimulation or to determine whether a composition is capable of modulating the activity of said T cell hybridoma. This test is performed by the following steps: (1) providing T cells from a T cell hybridoma or by isolation from a mammal, (2) cultivating the T cells under conditions which allow for proliferation, (3) contacting the proliferating T cells with an antigen presenting cell which has been contacted with an antigen or a nucleic acid encoding therefore, and (4) testing the T cells for a marker, for example, the IL-2 production is determined. Cells which are used for the test are cultured under conditions which allow for proliferation. For example, the DO11.10 T cell hybridoma is adequately cultured at 37° C. and 5% $CO_2$ in complete medium (RPMI 1640, supplemented with 10% FBS, penicillin/streptomycin, L-glutamine and $5 \times 10^{-5}$ M 2-mercaptoethanol). T cell activation signals are provided by antigen presenting cells which have been loaded with an appropriate antigenic peptide.

Alternatively, modulation of T cell activity may be verified by determining alterations or proliferation of antigen-specific T cells, which may be measured, for example, by known radiolabeling methods. For example, a labeled nucleotide may be added to a test culture medium. The incorporation of such labeled nucleotides into the DNA may serve as indicator for T cell proliferation. This test is not applicable for T cells that do not require antigen presentation for their proliferation such as T cell hybridomas. This test is useful for determining modulation of T cell activity in the case of untransformed T-cells which have been isolated from a mammal.

(IV) Provided is a method for inducing an immune response in an individual, said method comprising providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I) as defined in the first aspect; and administering said RNA modified with the structure according to formula (I) to said individual. In one embodiment, the RNA is administered by intranodal injection or is administered intradermally. The antigen of interest may be any antigen (e.g., an antigen of a virus (A, B, or C), such as influenza virus, CMV, or RSV)

and is preferably as defined above. In a preferred embodiment, said RNA is administered in the form of naked RNA, preferably by parenteral administration, for example, by intravenous, intramuscular, subcutaneous, intranodal, intradermal, intralymphatic, or intraperitoneal injection, preferably by injection into the lymphatic system such as by injection into lymphatic vessel(s), the spleen, and/or lymph node(s), preferably inguinal lymph node(s). Preferably, the administered RNA is taken up by immature dendritic cells of the individual. Preferably, the immune response is protective and/or therapeutic, for example, is useful for treating and/or preventing diseases such as cancerous diseases or infectious diseases. In one embodiment, the step of providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I), is performed in the absence of a 2'-O-ribose methyltransferase. In an alternative embodiment, said step is performed in the presence of a 2'-O-ribose methyltransferase.

(V) Provided is a method for inducing an immune response in an individual, said method comprising providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I) as defined in the first aspect; transferring said RNA modified with the structure according to formula (I) into immature antigen presenting cells; and administering the antigen presenting cells to said individual. In one embodiment, the step of providing an RNA comprising a nucleotide sequence encoding a peptide or protein comprising an antigen of interest (e.g., an antigen of a virus, such as influenza virus (A, B, or C), CMV, or RSV) or an antigen peptide thereof, said RNA being modified with the structure according to formula (I), is performed in the absence of a 2'-O-ribose methyltransferase. In an alternative embodiment, said step is performed in the presence of a 2'-O-ribose methyltransferase. In this aspect of the present invention, the RNA is transferred into immature antigen presenting cells in vitro by any nucleic acid transfer method, e.g., transfection such as lipofection, electroporation, or microinjection, known to the skilled person as described above. Preferably, the immature antigen presenting cells are immature dendritic cells. The immature antigen presenting cells into which the RNA is transferred in vitro may be isolated from an individual, for example, a patient to be immunized, or they may be differentiated from hematopoietic stem cells, wherein the hematopoietic stem cells may be isolated from the individual. The immature antigen presenting cells or the hematopoietic stem cells may be isolated from the individual by leukapheresis. Preferably, the immature antigen presenting cells are immature dendritic cells. Preferably, the immature antigen presenting cells are isolated from the individual to be immunized, the RNA is transferred into said isolated cells, and the cells are transferred back to said individual, preferably by parenteral administration, for example, by intravenous, intramuscular, subcutaneous, intranodal, intralymphatic, or intraperitoneal injection, preferably by injection into the lymphatic system such as by injection into lymphatic vessel(s), the spleen, and/or lymph node(s), preferably inguinal lymph node(s).

The ability to induce an immune reaction, including the suitability for vaccination against a target disease, may be readily determined by in vivo tests. For example, a composition, e.g., a vaccine composition or a pharmaceutical composition, may be administered to a mammal such as a laboratory animal, e.g., a mouse, rat, rabbit, etc., and blood samples may be taken from said animal before administration of the composition and at defined time points after administration of the composition, for example, 1, 2, 3, 4, 5, 6, 7, and 8 weeks after administration. Serum may be generated from the blood samples and the development of antibodies generated upon administration/immunization may be determined. For example, the concentration of antibodies may be determined. Furthermore, T cells may be isolated from the blood and/or the lymphatic system of the mammal, which may be tested for their reactivity against the antigen used for the immunization. Any readout system which is known to the skilled person may be used, for example, proliferation assays, cytokine secretion assays, assays to test for cytotoxic activity, or tetramer analysis etc. may be used. Furthermore, the increase of immune reactivity may also be determined by determining the number of antigen-specific T-cells, their cytotoxic potential, or their cytokine secretion pattern as set forth above.

As demonstrated in the examples of the present application, the present inventors have surprisingly found that by using the 5'-cap compounds of the present invention it is possible to incorporate beta-S-ARCA cap1 structures into RNA in one step thereby combining the positive effect of the thio-substitution with the cap1-defining 2'-O-methylation.

The present invention is illustrated by the following examples which illustrate preferred embodiments of the invention and should not be interpreted to limit the scope of the present invention as defined in the claims. Those examples which are not covered by the appending claims are given for comparative purposes only.

EXAMPLES

Figure 2:
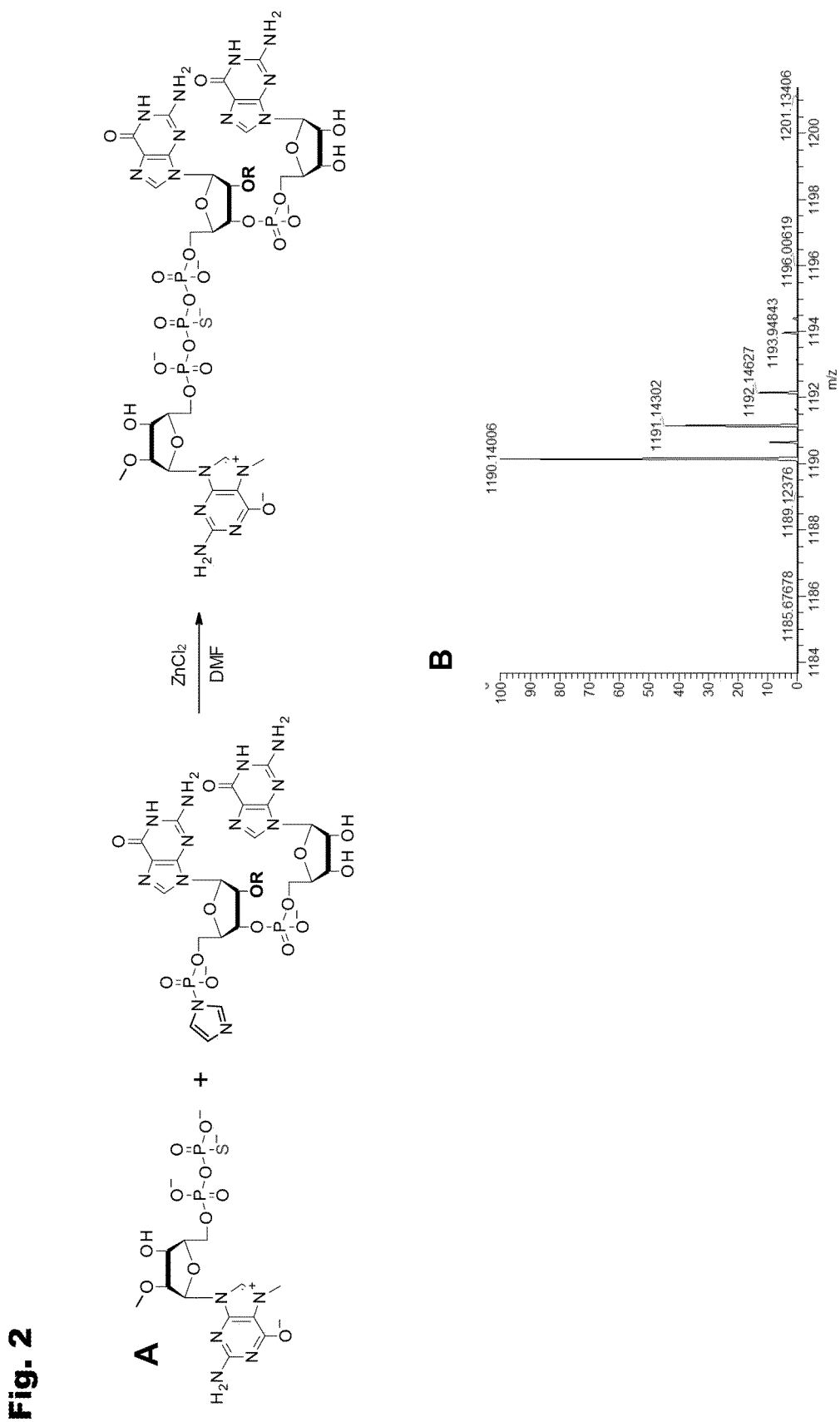
FIG. 2: Synthesis (A) and HRMS spectrum (B) of Compound 1 (m$_2^{7,2'-O}$Gpp$_S$pm$^{2'-O}$GpG; OR=OCH$_3$).

Abbreviations h: hour(s)
mM: millimolar ($10^{-3}$ mol/l)
NTP: nucleoside triphosphate Example 1—Synthesis of Cap Analogs To obtain co-transcriptionally capped in vitro transcribed mRNA, a 5'-cap compound of the invention (Compound 1, a compound of formula (I)) as shown in FIG. 2 (OR=OCH$_3$) was designed. Compound 1 contains the phosphorothioate substitution at the beta-position of the 5'-5' triphosphate bridge, a terminal 2'-O methylation to avoid incorporation in the reverse orientation, an internal 2'-O methylation reflecting the cap1 structure plus an additional guanosine moiety, which allows incorporation by the phage RNA polymerase. Synthesis and usage of the modified cap trinucleotide is described in the following.

5'-cap compounds of the present invention and other cap analogs can be synthesized starting from commercially available oligonucleotides such as $(pN)_{2-4}$ using standard procedures. For $m_2^{7,2'-O}Gpp_sum^{2'-O}GpG$ (Compound 1), 5'-phosphorylated 2'-O-methylated diguanosine 5',3'-dinucleotide ($pm^{2'-O}GpG$) was commercially obtained and used as starting material without further treatment. The dinucleotide was converted into the corresponding P-imidazolide derivative ($Im-pm^{2'-O}GpG$) by reacting with 10 equiv. of imidazole in DMF in the presence of 3 equiv. of 2,2'-dithiodipyridine/triphenylphosphine activation system (cf. FIG. 1; Mukaiyama and Hashimoto 1971). The nucleotide subunit, 2'-O-methyl guanosine 5'-O-(2-thiodiphosphate) ($m_2^{7,2'-OMe}$GDPβS), was synthesized as described earlier (Kowalska et al 2008). Then, $m_2^{7,2'-oMe}$GDPβS and the P-imidazolide Im-p$^{m2'-O}$GpG were coupled in DMF in presence of $ZnCl_2$ excess (8 equiv.) to the cap analog ($m_2^{7,2-O}$Gpp$_S$p$^{2'-O}$GpG, 38% HPLC yield; FIG. 2) as a mixture of two diastereoisomers (D1 and D2, named according to the elution order from RP HPLC column). The diastereoisomers were separated by RP HPLC (Discovery Amide RP C16 column) into pure diastereoisomers D1 and D2.

Spectroscopic Data $m_2^{7,2-O}$Gpp$_S$p$^{2'-O}$GpG (Compound 1)

(D1): $^1$H NMR (400 MHz, $D_2O$) δ 9.07 (s, 1H), 8.16 (s, 1H), 8.07 (s, 1H), 5.97 (d, J=2.24 Hz, 1H), 5.87 (d, J=5.98 Hz, 1H), 5.82 (d, J=5.48 Hz, 11H), 4.85-5.00 (m, 1H), 4.74-4.87 (m, 2H, partially overlapped with signal of HDO), 4.61 (t, J=5.35 Hz, 11H), 4.51 (t, J=4.36 Hz, 2H), 4.12-4.48 (m, 9H), 4.07 (s, 3H), 3.58 (s, 3H), 3.43 (s, 3H); $^{31}$P NMR (162 MHz, $D_2O$) δ 30.93 (t, J=26.9 Hz, 1P) −0.59 (br. s., 1P) −11.94 (d, J=26.9 Hz, 1P) −12.08 (d, J=26.9 Hz, 1P);

(D2): $^1$H NMR (400 MHz, $D_2O$) δ 9.08 (s, 1H), 8.16 (s, 1H), 8.10 (s, 1H), 5.89 (d, J=2.49 Hz, 1H), 5.87 (d, J=5.98 Hz, 11H), 5.82 (d, J=5.98 Hz, 1H), 4.97 (m, 1H), 4.58-4.55 (~t, 1H) 4.85-4.73 (m, 2H, overlap with signal of HDO), 4.54-4.47 (m, 2H), 4.13-4.46 (m, 9H), 4.07 (s, 3H), 3.57 (s, 3H), 3.44 (s, 3H); $^{31}$P NMR (162 MHz, $D_2O$) δ 30.40 (dt, J=26.9 Hz, 1P) −0.60 (br. s., 1P) −11.98 (d, J=26.9 Hz, 1P) −12.43-12.06 (d, J=26.9 Hz, 1P)

HRMS calcd. m/z for $C_{33}H_{44}N_{15}O_{24}P_4S^-$ [M-H]$^-$ 1190.1360, recorded. 1190.13936

Example 2—In Vitro Synthesis of Capped mRNA by In Vitro Transcription Using Cap Analogs For incorporation of different cap analogs during in vitro transcription the same protocol as for incorporation of regular beta-S-ARCA dinucleotide caps can be used. In the example given here, 3 mM cap analog and 7.5 mM NTPs were added to the transcription reaction. Yield (in mg RNA per ml reaction volume) and integrity of RNA produced with one of the diastereomers (D1/D2) of Compound 1 or one of the diastereomers (D1/D2) of beta-S-ARCA were comparable as given in the following table.

|  | Yield of reaction (mg RNA/ml reaction volume) | RNA integrity (BIOANALYZER) |
| --- | --- | --- |
| beta-S-ARCA (D1) | 6.54 | 82% |
| Compound 1 (D1) | 6.39 | 87% |
| beta-S-ARCA (D2) | 6.42 | 82% |
| Compound 1 (D2) | 5.81 | 80% |

Example 3—Protein Expression from Differently Capped mRNA in Cell Culture

Figure 3:
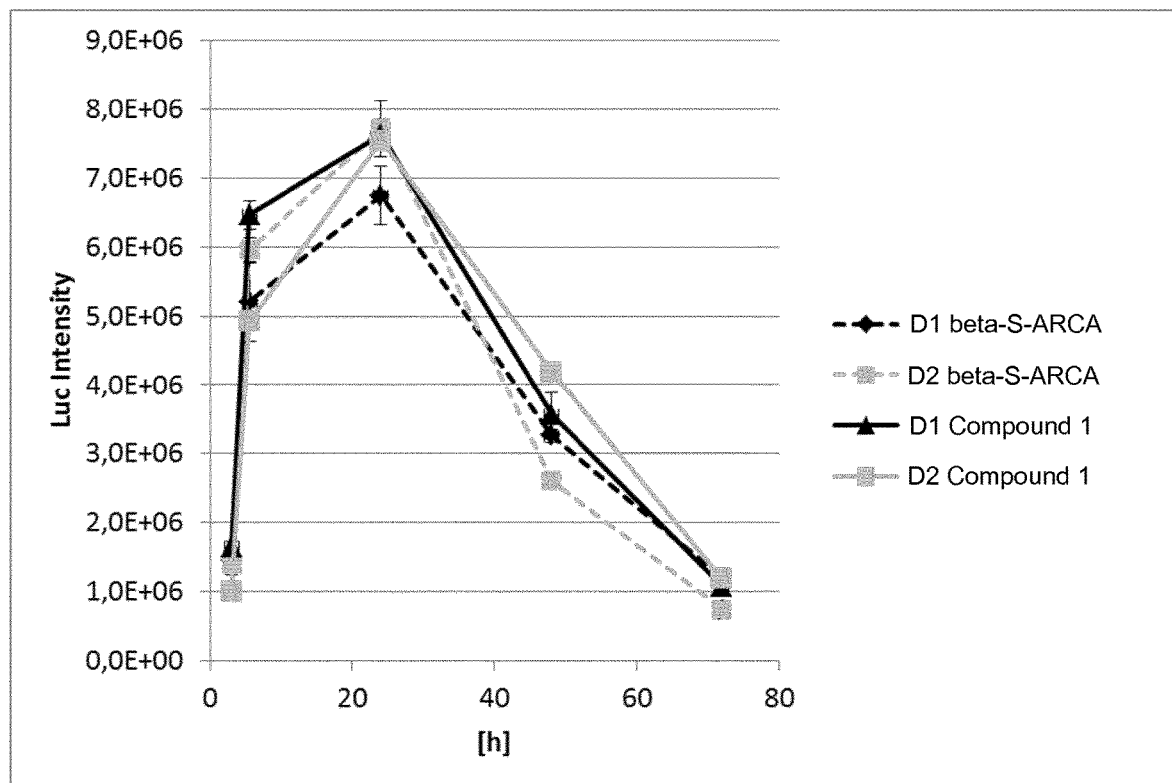
FIG. 3: Comparison of translatability of RNAs capped co-transcriptionally with different 5'-cap analogs. D1 beta-S-ARCA: D1 diastereomer of beta-S-ARCA; D2 beta-S-ARCA: D2 diastereomer of beta-S-ARCA; D1 Compound 1: D1 diastereomer of Compound 1; D2 Compound 1: D2 diastereomer of Compound 1. Luciferase RNAs containing the respective cap structures were electroporated into hiDCs. Luciferase activity was recorded over 72 h.
Figure 4:
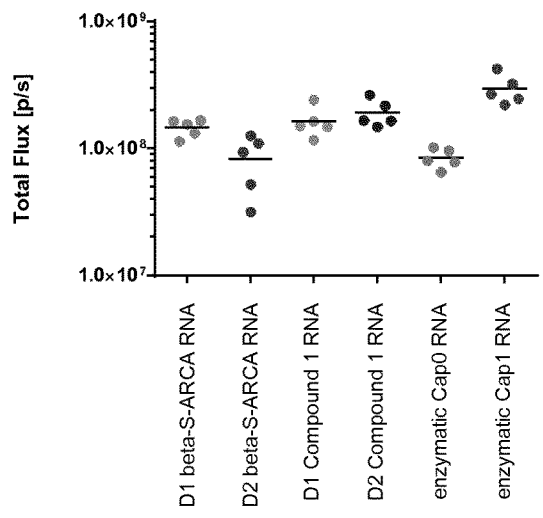
FIG. 4: in vivo translation of RNAs modified with different 5'-cap analogs. D1/D2 beta-S-ARCA RNA: RNA was prepared by IVT using either the D1 or D2 diastereomer of beta-S-ARCA; D1/D2 Compound 1 RNA: RNA was prepared by IVT using either the D1 or D2 diastereomer of Compound 1; enzymatic Cap0/Cap1 RNA: RNA was prepared by IVT in the absence of any cap analog and then, in a second step, enzymatically capped either by using vaccinia capping enzyme alone (enzymatic Cap0 RNA) or by using vaccinia capping enzyme together with methyltransferase (enzymatic Cap1 RNA).
Figure 4:
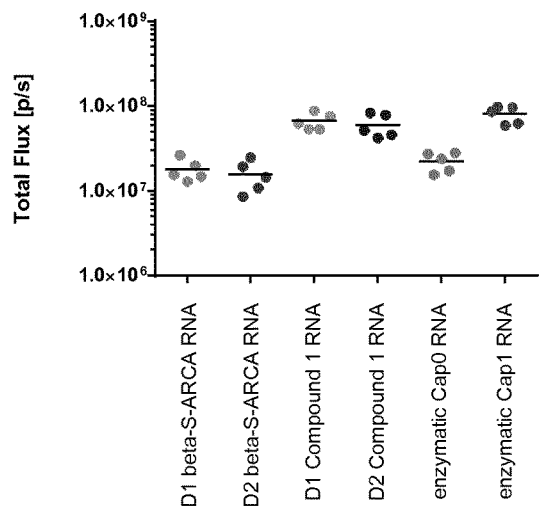
Figure 4:
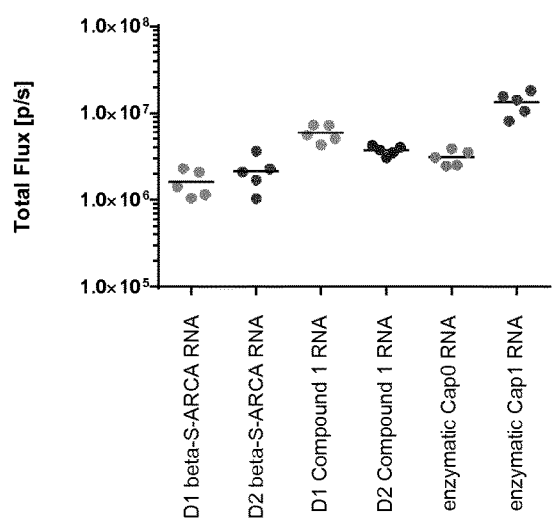

As a functional assay of cap analog incorporation, and as a test of translatability of the resulting cap structure, differently capped mRNA encoding a Luciferase reporter was transfected into human immature dendritic cells (hiDCs). For that, 700 ng capped RNA per well were formulated with liposomes as described in Kranz et al., Nature 534, 396-401 (2016), and added to a 96-well containing 5E04 hiDCs. Subsequently, reporter activity was recorded over 72 h. The results are shown in FIG. 3.

mRNAs co-transcriptionally capped with the D1 or D2 diastereomer of Compound 1 were functional and translated in hiDCs at comparable levels as mRNA capped with the corresponding D1 or D2 diastereomer of beta-S-ARCA, indicating that also with the compounds of formula (I) according to the present invention the advantages of the beta-S-ARCA modification were still active (FIG. 3).

Example 4—mRNA Modified with a 5'-Cap Compound of Formula (I) Combines Improved mRNA Stability and Translation Efficiency with Evasion of an Immune Response Via IFIT1

Luciferase mRNAs were co-transcriptionally capped with D1 or D2 diastereomer of Compound 1 or with the corresponding D1 or D2 diastereomer of beta-S-ARCA, as described above. In addition, triphosphate Luc mRNA (i.e., transcribed in the absence of any cap analog) was enzymatically capped using the NEB vaccinia capping enzyme kit (enzymatic Cap0/Cap1 RNA). To obtain enzymatic cap0 structures the vaccinia capping enzyme was used as is, for enzymatic cap1 structures the vaccinia methyltransferase was also added. Subsequently, the resulting capped mRNA preparations were purified in order to decrease or eliminate the amount of double stranded RNA. Furthermore, the small amount of uncapped RNA present in the co-transcriptionally capped mRNA preparations, which in previous experiments has been shown to interfere with the analysis, was enzymatically converted into cap0 (for mRNAs capped with dinucleotides) or cap1 structures (for mRNAs capped with trinucleotides). The resulting mRNA preparations were then formulated with F12 and given intraveneously in Balb/c mice. Per group, five mice were tested, with a dosage of 10 μg RNA per mouse. Strength and kinetics of luciferase expression was monitored by bioluminescence in vivo imaging 6 h, 24 h and 48 h after application.

While in this setting the beta-S-substitution has—if at all—only a minor effect, as observed by the similar expression profiles of enzymatically capped cap0 RNA compared to beta-S-ARCA(D1) and (D2) cap0 RNAs, the main factor driving in vivo expression is the 2'-O-methylation of the cap1 structure. Accordingly, the enzymatically capped cap1 mRNA preparations give the highest protein expression at any time point measured. However, RNAs capped with Compound 1 demonstrate similar protein levels 20 h after application, and only slightly lower levels at the other time points (and always higher levels compared to all cap0 RNAs). Thus, the 5'-cap compounds of the present invention allow incorporation of beta-S-ARCA cap1 structures into RNA that combine the positive effect of the thio-substitution with the cap1-defining 2'-O-methylation.

Example 5—Protein Expression from Differently Capped mRNA In Vivo

Murine erythropoietin (mEPO) mRNAs containing 1-methylpseudouridine ($m^1Ψ$) were co-transcriptionally capped with ARCA G or with the D1 diastereomer of beta-S-ARCA (designated as D1), as described above. In addition, triphosphate mEPO mRNA (i.e., transcribed in the absence of any cap analog) was enzymatically capped using the NEB vaccinia capping enzyme kit (enzymatic Cap0/Cap1 RNA). To obtain enzymatic cap0 structures (designated as Ecap0) the vaccinia capping enzyme with RNA triphosphatase and guanylyltransferase activities was used as is, for enzymatic cap1 structures (designated as Ecap1) the vaccinia methyltransferase with 2'-O-methyltransferase activity was also added. Subsequently, the resulting differently capped mRNA preparations were purified in order to decrease or eliminate the amount of double stranded RNA. Furthermore, the small amount of uncapped RNA present in the co-transcriptionally capped mRNA preparations, which in previous experiments has been shown to interfere with the analysis, was enzymatically converted into cap0 and then into cap1 structures. In the mRNA preparation using D1 structures the resulting product after the treatment with the enzymes was designated as D1+Ecap1, whereas in the case of ARCA G the resulting product after the treatment with the enzymes was designated as ARCA G+Ecap1. The mRNA preparations were then formulated with TransIT® and injected intraperitoneally into Balb/c mice. Per group, five mice were tested, with a dosage of 3 μg RNA per mouse. Translation of the mEPO mRNA was monitored by ELISA in the plasma collected at 6 h, 24 h, 48 h and 72 h after application.

Figure 5:
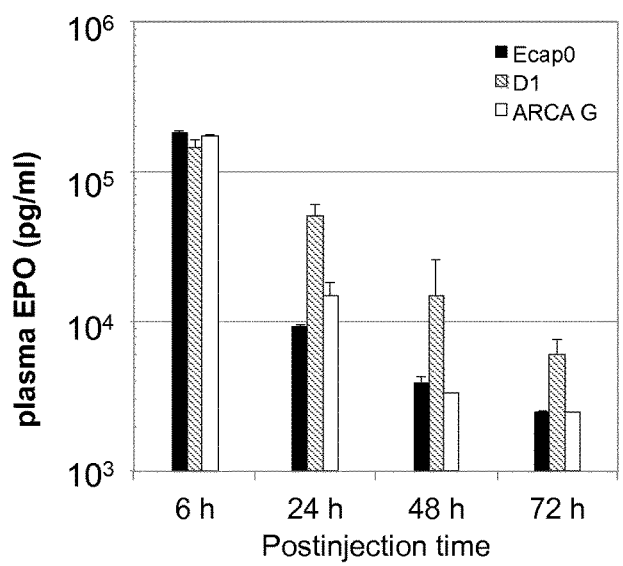
FIG. 5: in vivo translation of murine erythropoietin (mEPO) RNAs modified with different 5'-cap analogs having a cap0 structure (A) or a cap1 structure (B). ARCA G: RNA co-transcriptionally capped with ARCA G; D1: RNA co-transcriptionally capped with the D1 diastereomer of beta-S-ARCA; Ecap0: RNA enzymatically capped providing a cap0 structure; ARCA G+Ecap1: RNA co-transcriptionally capped with ARCA G, then enzymatically capped using vaccinia capping enzyme and vaccinia methyltransferase which provide a cap1 structure; D1+Ecap1: RNA co-transcriptionally capped with the D1 diastereomer of beta-S-ARCA, then enzymatically capped using vaccinia capping enzyme and vaccinia methyltransferase which provide a cap1 structure; Ecap1: RNA enzymatically capped providing a cap1 structure. mEPO mRNA (3 μg) containing 1-methylpseudouridine (m1Ψ) were formulated in TransIT® and injected i.p. into mice.
Figure 5:
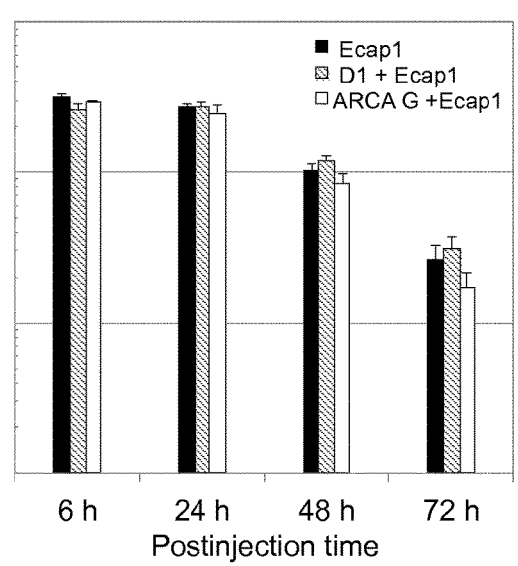

As can be seen from FIG. 5, the presence of a cap1 structure of the invention in RNA results in much higher expression levels of mEPO compared to RNA having a cap0 structure, in particular 24 hours after injection. Moreover, FIG. 5 shows that by using RNA containing a cap1 structure of the invention it is possible to maintain high mEPO plasma levels for at least 72 hours. Thus, this example demonstrates that it is not necessary to administer RNA comprising a nucleotide sequence encoding a peptide or protein at least twice per day in order to maintain high expression levels of the peptide or protein. Rather, by using the present invention it is possible to administer the RNA at most once per day, referably at most once per two days, preferably at most once per three days or at most once per four days while maintaining high expression levels of the peptide or protein. This has the advantage for the patient that the number of administrations (e.g., injections) can be significantly reduced which is particularly beneficial with patients who receive their treatment (e.g., a pharmaceutical composition) over an extended period of time, such as chronic or long-term patients.

The invention claimed is:

1. A 5'-cap compound having the 5'-cap structure according to formula (I):

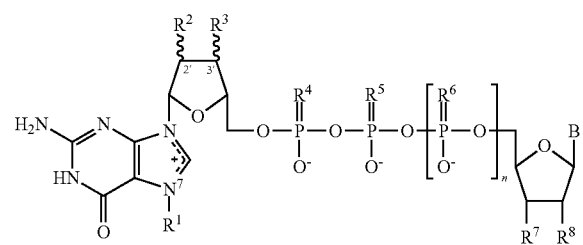

formula (I)

wherein $R^1$ is selected from the group consisting of optionally substituted alkyl, optionally substituted alkenyl, optionally substituted alkynyl, optionally substituted cycloalkyl, optionally substituted heterocyclyl, optionally substituted aryl, and optionally substituted heteroaryl;

$R^2$ and $R^3$ are independently selected from the group consisting of H, halo, OH, and optionally substituted alkoxy, or $R^2$ and $R^3$ together form O—X—O, wherein X is selected from the group consisting of optionally substituted $CH_2$, optionally substituted $CH_2CH_2$, optionally substituted $CH_2CH_2CH_2$, optionally substituted $CH_2CH(CH_3)$, and optionally substituted $C(CH_3)_2$, or $R^2$ is combined with the hydrogen atom at position 4' of the ring to which $R^2$ is attached to form —O—CH$_2$— or —CH$_2$—O—;

$R^4$ and $R^6$ are independently selected from the group consisting of O, S, Se, and $BH_3$;

$R^5$ is selected from the group consisting of S, Se, and $BH_3$;

$R^7$ is a mononucleotide or an oligonucleotide having 2 to 9 bases;

$R^8$ is H, halo, or optionally substituted alkoxy;

n is 1, 2, or 3; and

B is a purine or pyrimidine base moiety;

wherein the 5'-cap compound is capable of co-transcriptional incorporation into an RNA strand.

2. The 5'-cap compound of claim 1, wherein $R^1$ is selected from the group consisting of optionally substituted $C_{1-4}$ alkyl, optionally substituted $C_{2-4}$ alkenyl, and optionally substituted aryl.

3. The 5'-cap compound of claim 1, wherein $R^2$ and $R^3$ are independently selected from the group consisting of H, F, OH, methoxy, ethoxy, propoxy, and 2-methoxyethoxy.

4. The 5'-cap compound of claim 1, wherein $R^2$ is selected from the group consisting of H, F, methoxy, ethoxy, propoxy and 2-methoxyethoxy.

5. The 5'-cap compound of claim 1, wherein $R^8$ is selected from the group consisting of H, F, methoxy, ethoxy, propoxy, and 2-methoxyethoxy.

6. The 5'-cap compound of claim 1, wherein B is a naturally occurring purine or pyrimidine base moiety or a modified form thereof.

7. The 5'-cap compound of claim 1, wherein B is selected from the group consisting of guanine, adenine, cytosine, thymine, uracil, and modified forms thereof, wherein the modified purine or pyrimidine base moiety is modified by one or more alkyl groups.

8. The 5'-cap compound of claim 7, wherein the modified purine or pyrimidine base moiety is selected from the group consisting of $N^7$-alkyl-guanine, $N^6$-alkyl-adenine, 5-alkyl-cytosine, 5-alkyl-uracil, and N(1)-alkyl-uracil.

9. The 5'-cap compound of claim 1, wherein B is G or A.

10. The 5'-cap compound of claim 1, wherein $R^7$ is a mononucleotide or an oligonucleotide having 2, 3, 4, 5, or 6 bases.

11. The 5'-cap compound of claim 1, wherein $R^7$ is bonded via its 5'-end to the ring to which $R^8$ is attached.

12. The 5'-cap compound of claim 1, wherein $R^7$ is a ribomononucleotide or ribooligonucleotide.

13. The 5'-cap compound of claim 12, wherein $R^7$ is a ribonucleotide having a free OH group at position 2'; or $R^7$ is a ribooligonucleotide, wherein both the ribose moiety at the 3'-end of the ribooligonucleotide and the ribose moiety at the 5'-end of the ribooligonucleotide have a free OH group at position 2'; or $R^7$ is a ribooligonucleotide, wherein the OH group at position 2' of at least the ribose at the 5'-end of the ribooligonucleotide is replaced with a substituent selected from the group consisting of H, halo, and optionally substituted alkoxy, and the ribose at the 3'-end of the ribooligonucleotide has a free OH group at position 2'.

14. The 5'-cap compound of claim 1, wherein the internucleotide linkage between the mononucleotide or oligonucleotide and the ring to which $R^7$ is attached is selected from the group consisting of phosphate, phosphorothioate, boranophosphate, imidophosphate, alkylene phosphate, phosphorodithioate, alkylphosphonate, phosphotriester, phosphoroamidite, and non-nucleotide linker.

15. The 5'-cap compound of claim 1, wherein the internucleotide linkage(s) between the nucleotides in the oligonucleotide is (are) selected from the group consisting of phosphate, phosphorothioate, boranophosphate, imidophosphate, alkylene phosphate, phosphorodithioate, alkylphosphonate, phosphotriester, phosphoroamidite, and non-nucleotide linker.

16. The 5'-cap compound of claim 1, wherein the stereochemical configuration at the P atom comprising the substituent $R^5$ corresponds to that at the Pp atom of the D1 diastereomer of beta-S-ARCA.

17. A composition or kit comprising a 5'-cap compound of claim 1.

18. An RNA which is modified with a 5'-cap compound of claim 1.

19. A composition or cell comprising an RNA of claim 18.

20. The RNA of claim 18, wherein the RNA further comprises a nucleotide sequence encoding a peptide or protein of interest.

21. A method for expressing a peptide or protein of interest in an individual comprising the step of administering to said individual the RNA of claim 20.

22. A method of treating a disease or disorder in a subject comprising the step of administering to said subject the RNA of claim 20.

23. The method of claim 22, wherein the RNA is administered to the subject at most once per day, preferably at most once per two days, preferably at most once per three days or at most once per four days.

24. The method of claim 22, wherein the RNA is administered to a chronic patient or long-term patient, e.g., over an extended period of time, such as at least 1 week, at least 2 weeks, at least 3 weeks, at least 4 weeks, at least 1 month, at least 2 months, at least 3 months, at least 4 months, at least 5 months, at least 6 months, at least 12 months, at least 2 years, at least 3 years, at least 4 years, at least 5 years, or at least 10 years, e.g., up to 2 weeks, up to 3 weeks, up to 4 weeks, up to 1 month, up to 2 months, up to 3 months, up to 4 months, up to 5 months, up to 6 months, up to 12 months, up to 2 years, up to 3 years, or up to 4 years, up to 5 years, up to 10 years, or the entire life of the patient.

25. A method of increasing the stability of an RNA in cells and/or for increasing the expression of an RNA in cells, said method comprising:
 a. providing said RNA with the structure according to formula (I) as defined in claim 1; and
 b. transferring said RNA modified with the structure according to formula (I) into the cells.

26. The method of claim 25, wherein the step of providing said RNA with the structure according to formula (I) is performed in the absence of a 2'-O-ribose methyltransferase.

27. A method for providing an RNA with a 5'-cap structure, said method comprising: performing a transcription reaction using a template nucleic acid in the presence of a 5'-cap compound of claim 1, wherein the template nucleic acid is DNA.

28. The method of claim 27, wherein the transcription reaction is performed in vitro.

29. The method of claim 27, wherein the transcription reaction is performed using an RNA polymerase selected from the group consisting of T3, T7 and SP6 RNA polymerases.

30. The method of claim 27, wherein the RNA comprises a nucleotide sequence encoding a peptide or protein of interest.

31. The method of claim 27, which is performed in the absence of a 2'-O-ribose methyltransferase.

32. The RNA of claim 20, wherein the peptide or protein of adhesion molecules, interest is selected from the group consisting of cytokines, immunoglobulins, immunologically active compounds, hormones, growth factors, enzymes, receptors, protease inhibitors, apoptosis regulators, transcription factors, tumor suppressor proteins, structural proteins, reprogramming factors, genomic engineering proteins, and blood proteins.

33. The 5'-cap compound of claim 7, wherein B is selected from the group consisting of guanine, adenine, cytosine, uracil, and modified forms thereof and wherein the modified purine or pyrimidine base moiety is modified by one or more $C_{1-4}$ alkyl groups.

34. The 5'-cap compound of claim 7, wherein B is selected from the group consisting of guanine, adenine, cytosine, and modified forms thereof and wherein the modified purine or pyrimidine base moiety is modified by one or more $C_{1-4}$ alkyl groups.

35. The 5'-cap compound of claim 7, wherein B is selected from the group consisting of guanine, adenine, and modified forms thereof and wherein the modified purine or pyrimidine base moiety is modified by one or more $C_{1-4}$ alkyl groups.

36. The 5'-cap compound of claim 8, wherein the modified purine or pyrimidine base moiety is selected from the group consisting of $N^7$-$C_{1-4}$ alkyl-guanine, $N^6$-$C_{1-4}$ alkyl-adenine, 5-$C_{1-4}$ alkyl-cytosine, 5-$C_{1-4}$ alkyl-uracil, and N(1)-$C_{1-4}$ alkyl-uracil.

37. The 5'-cap compound of claim 8, wherein the modified purine or pyrimidine base moiety is selected from the group consisting of $N^7$-methyl-guanine, $N^6$-methyl-adenine, 5-methyl-cytosine, 5-methyl-uracil, and N (1)-methyl-uracil.

38. The RNA of claim 32, wherein the cytokines is erythropoietin; the adhesion molecules is an integrin; the immunologically active compounds are tumor-associated antigens, pathogen-associated antigens, allergens, or autoantigens; the hormones are vasopressin, insulin, or growth hormone; the growth factors are VEGFA; the enzymes are herpes simplex virus type 1 thymidine kinase (HSV1-TK), hexosaminidase, phenylalanine hydroxylase, pseudocholinesterase, pancreatic enzymes, or lactase; the receptors are growth factor receptors; the protease inhibitors are alpha 1 antitrypsin; the apoptosis regulators are BAX; the transcription factors are FOXP3; the tumor suppressor proteins are p53; the structural proteins are surfactant proteins; the reprogramming factors are OCT4, SOX2, c-MYC, KLF4, LIN28, or NANOG; the genomic engineering proteins are clustered regularly spaced short palindromic repeat-CRISPR-associated protein 9 (CRISPR-Cas9); or the blood proteins are fibrinogen.

39. The 5'-cap compound of claim 1, wherein $R^8$ is alkoxy.

40. The 5'-cap compound of claim 1, wherein $R^8$ is methoxy.

41. The 5'-cap compound of claim 1, wherein $R^7$ is a ribomononucleotide such that the 5'-cap compound is a trinucleotide.

42. The 5'-cap compound of claim 1, wherein $R^7$ is a ribomononucleotide such that the 5'-cap compound is a trinucleotide and the ribomononucleotide has a free OH group at position 2'.

43. The 5'-cap compound of claim 1, wherein $R^7$ is *[pN($R^{8'}$)] a [pN] b, wherein * indicates the attachment point of $R^7$ to the ring to which $R^7$ is attached; each p is a phosphate moiety; each N($R^{8'}$) is a nucleoside substituted with $R^{8'}$ at position 2' wherein $R^{8'}$ is selected from the group consisting of H, F, methoxy, ethoxy, and propoxy; a is 0, 1, or 2; and b is 1 and the N of [pN] b is a ribonucleoside having a free OH group at position 2'.

44. The 5'-cap compound of claim 43, wherein a is 0 such that the 5'-cap compound is a trinucleotide.

45. The 5'-cap compound of claim 43, wherein $R^8$ is methoxy.

46. A 5'-cap compound having a structure according to formula (III):

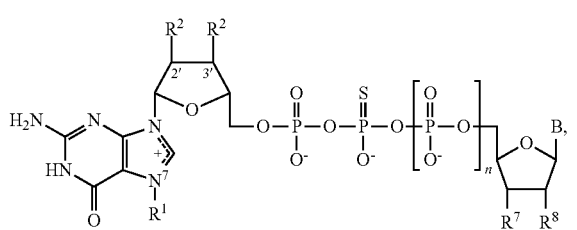

formula (III)

wherein:
$R^1$ is methyl or ethyl;
one of $R^2$ and $R^3$ is $OCH_3$ and the other is OH;
n is 1;
$R^7$ is *pGpN or *pG, where * indicates the attachment point of $R^7$ to the ring to which $R^7$ is attached and p is phosphate;
$R^8$ is methoxy; and
B is a purine or pyrimidine base moiety;
wherein the 5'-cap compound is capable of co-transcriptional incorporation into an RNA strand.

47. The 5'-cap compound of claim 46, wherein $R^1$ is methyl.

48. The 5'-cap compound of claim 46, wherein $R^2$ is OH and $R^3$ is $OCH_3$.

49. The 5'-cap compound of claim 46, wherein B is guanine or adenine.

50. An RNA which is modified with a 5'-cap compound of claim 46.

51. The RNA of claim 50, wherein the RNA further comprises a nucleotide sequence encoding a peptide or protein of interest.

52. A composition or cell comprising an RNA of claim 50.

53. The composition or cell of claim 52, wherein the RNA further comprises a nucleotide sequence encoding a peptide or protein of interest.

54. A method of treating a disease or disorder in a subject comprising the step of administering to said subject:
(i) the RNA of claim 51, or
(ii) a composition or cell comprising the RNA of claim 51.

55. The 5'-cap compound of claim 46, wherein B is adenine.

56. The 5'-cap compound of claim 46, wherein B is guanine.

57. The 5'-cap compound of claim 46, wherein $R^1$ is methyl; $R^2$ is OH; $R^3$ is $OCH_3$; $R^7$ is *pG; and B is adenine.

58. An RNA which is modified with a 5'-cap compound of claim 57.

59. The RNA of claim 58, wherein the RNA further comprises a nucleotide sequence encoding a peptide or protein of interest.

60. A composition or cell comprising an RNA of claim 58.

61. The composition or cell of claim 60, wherein the RNA further comprises a nucleotide sequence encoding a peptide or protein of interest.

62. The 5'-cap compound of claim 46, wherein $R^2$ is $OCH_3$ and $R^3$ is OH.

63. The 5'-cap compound of claim 46, wherein $R^1$ is methyl; $R^2$ is $OCH_3$; $R^3$ is OH; $R^7$ is *pG; and B is guanine.

64. An RNA which is modified with a 5'-cap compound of claim 63.

65. The RNA of claim 64, wherein the RNA further comprises a nucleotide sequence encoding a peptide or protein of interest.

66. A composition or cell comprising an RNA of claim 64.

67. The composition or cell of claim 66, wherein the RNA further comprises a nucleotide sequence encoding a peptide or protein of interest.

68. The 5'-cap compound of claim 46, wherein R' is *pG such that the 5'-cap compound is a trinucleotide.

69. The 5'-cap compound of claim 46, wherein the N of $R^7$ has a free OH group at position 2' or the G of $R^7$ has a free OH group at position 2'.

* * * * *

UNITED STATES PATENT AND TRADEMARK OFFICE
CERTIFICATE OF CORRECTION

PATENT NO. : 12,281,138 B2
APPLICATION NO. : 16/980300
DATED : April 22, 2025
INVENTOR(S) : Andreas Kuhn et al.

It is certified that error appears in the above-identified patent and that said Letters Patent is hereby corrected as shown below:

In the Claims

In Claim 32, Column 108, Line 7, after "of" delete "adhesion molecules".
In Claim 32, Column 108, Line 8, after "cytokines," insert --adhesion molecules,--.
In Claim 37, Column 108, Lines 37-38, replace "N (1)-methyl-uracil." with --N(1)-methyl-uracil.--.
In Claim 43, Column 109, Lines 1-2, replace "*[pN (R8') a [pN] b," with --*[pN(R8')a[pN]b--.
In Claim 43, Column 109, Line 7, replace "[pN] b" with --[pN]b--.
In Claim 68, Column 110, Line 40, replace "R'" and insert --R7--.

Signed and Sealed this
Seventeenth Day of June, 2025

Coke Morgan Stewart
*Acting Director of the United States Patent and Trademark Office*